United States Patent
Tomichi et al.

(10) Patent No.: US 6,764,823 B2
(45) Date of Patent: Jul. 20, 2004

(54) ANTIMICROBIAL METHODS AND MATERIALS

(75) Inventors: Che-Shen C. Tomichi, Kalamazoo, MI (US); Cheryl Quinn, Kalamazoo, MI (US); Staffan Arvidson, Åkersberga (SE)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/828,523

(22) Filed: Apr. 6, 2001

(65) Prior Publication Data

US 2002/0168697 A1 Nov. 14, 2002

Related U.S. Application Data

(60) Provisional application No. 60/266,327, filed on Apr. 6, 2000, now abandoned.

(51) Int. Cl.$^7$ .......................... C12Q 1/70; C12P 21/06; C07H 21/04

(52) U.S. Cl. .......................... 435/6; 435/7.1; 435/7.72; 435/7.9; 435/69.1; 435/252.3; 435/320.1; 530/350; 530/300; 536/23.2; 536/23.7; 536/23.4; 424/200.1

(58) Field of Search .................. 435/6, 69.1, 252.3, 435/320.1, 70.1, 7.72, 7.9; 530/300, 350; 536/23.7, 23.2, 23.4; 424/200.1

(56) References Cited

U.S. PATENT DOCUMENTS

| | | | |
|---|---|---|---|
| 4,877,612 A | 10/1989 | Berger et al. | |
| 5,284,933 A | 2/1994 | Döbeli et al. | |
| 5,310,663 A | 5/1994 | Döbeli et al. | |
| 5,585,277 A | 12/1996 | Bowie et al. | |
| 5,587,228 A | 12/1996 | Baker et al. | |
| 5,783,397 A | 7/1998 | Hughes et al. | |
| 6,111,074 A | 8/2000 | Petit | |
| 6,455,323 B1 | 9/2002 | Holden et al. | |

FOREIGN PATENT DOCUMENTS

| | | |
|---|---|---|
| EP | 109 942 B1 | 5/1984 |
| EP | 180 564 B1 | 5/1986 |
| EP | 231 039 B1 | 8/1987 |
| EP | 786 519 A2 | 7/1997 |
| EP | 0 786 519 * | 7/1997 |
| GB | 2 189 141 A | 10/1987 |
| WO | WO 96/10579 A1 | 4/1996 |
| WO | WO 97/11690 A2 | 4/1997 |
| WO | WO 97/30070 A1 | 8/1997 |
| WO | WO 99/01473 | 1/1999 |
| WO | WO 99/32657 A1 | 7/1999 |
| WO | WO 99/43692 A1 | 9/1999 |
| WO | WO 99/55729 | 11/1999 |
| WO | WO 00/12678 | 3/2000 |
| WO | WO 01/02588 | 1/2001 |
| WO | WO 01/16292 A | 3/2001 |
| WO | WO 01/34809 A | 5/2001 |
| WO | WO 01/49775 | 7/2001 |
| WO | WO 01/77365 | 10/2001 |

OTHER PUBLICATIONS

Benet et al., 1990, in The Pharmacological Basis of Therapeutics, Gilman et al., eds., Pergamon Press, New York, pp. 3–32.*

Atlas et al., *Handbook of Microbiological Media*, 2$^{nd}$ Ed., CRC Press, Boca Raton, FL (1997); title page, publisher's page, and table of contents only: 3 pages.

Berger–Bächi et al., "FemA, a host–mediated factor essential for methicillin resistance in *Staphylococcus aureus*: molecular cloning and characterization," *Mol Gen Genet.* Oct. 1989;219(1–2):263–9.

Burgess et al., "Possible dissociation of the heparin–binding and mitogenic activities of heparin–binding (acidic fibroblast) growth factor–1 from its receptor–binding activities by site–directed mutagenesis of a single lysine residue," *J Cell Biol.* Nov. 1990;111(5 Pt 1):2129–2138.

Gerhold et al., "It's the genes! EST access to human genome content," *Bioessays.* Dec. 1996;18(12):973–981.

Jawetz et al., "Review of Medical Microbiology," *The growth & death of microorganisms*, 11th Ed., pp. 83–92 (1974), Lange Medical Publications, Los Altos, CA.

Jobling et al., "Analysis of structure and function of the B subunit of cholera toxin by the use of site–directed mutagenesis," *Mol Microbiol.* Jul. 1991;5(7):1755–1767.

Kuroda et al., "Whole genome sequencing of meticillin–resistant *Staphylococcus aureus*," *Lancet* Apr. 21, 2001;357(9264):1225–1240.

Pucci et al., "Identification and characterization of cell wall–cell division gene clusters in pathogenic gram–positive cocci," *J Bacteriol.* Sep. 1997;179(17):5632–5635.

Romine et al., "Complete sequence of a 184–kilobase catabolic plasmid from *Sphingomonas aromaticivorans* F199," *J Bacteriol.* Mar. 1999;181(5):1585–1602.

Chopra, "Over–expression of target genes as a mechanism of antibiotic resistance in bacteria," *J Antimicrob Chemother.* Jun. 1998;41(6):584–8.

Fields et al., "A novel genetic system to detect protein–protein interactions," *Nature.* Jul. 20, 1989;340(6230):245–6.

Fields et al., "The two–hybrid system: an assay for protein–protein interactions," *Trends Genet.* Aug. 1994;10(8):286–92.

(List continued on next page.)

*Primary Examiner*—Mark Navarro
*Assistant Examiner*—Padmavathi Baskar
(74) *Attorney, Agent, or Firm*—Mueting, Raasch & Gebhardt, P.A.

(57) ABSTRACT

The present invention provides methods of identifying antimicrobial agents that target genes essential for the survival of Staphylococcus bacteria, including antimicrobial agents that interfere with the expression of essential coding sequence products and antimicrobial agents that interfere with the function of essential coding sequence products.

10 Claims, 25 Drawing Sheets

OTHER PUBLICATIONS

Fire et al., "Potent and specific genetic interference by double–stranded RNA in *Caenorhabditis elegans*," *Nature*. Feb. 19, 1998;391(6669):806–11.

Flock et al., "Reconsideration of the role of fibronectin binding in endocarditis caused by *Staphylococcus aureus*," *Infect Immun*. May 1996;64(5):1876–8.

Grosjean et al., "Preferential codon usage in prokaryotic genes: the optimal codon–anticodon interaction energy and the selective codon usage in efficiently expressed genes," *Gene*. Jun. 1982;18(3):199–209.

Hopp et al., "A short polypeptide marker sequence useful for recombinant protein identification and purification," *Bio/Technology*. Oct. 1988;6:1204–10 (1988).

Janzon et al., "The role of the δ–lysin gene (hld) in the regulation of virulence genes by the accessory gene regulator (agr) in *Staphylococcus aureus*," *EMBO J*. May 1990;9(5):1391–9.

Ji et al., "Identification of critical staphylococcal genes using conditional phenotypes generated by antisense RNA," *Science*, Sep. 21, 2001;293(5538):2266–9.

Jorgensen et al., eds., *Methods for Dilution Antimicrobial Susceptibility Tests for Bacteria That Grow Aerobically, 3rd ed.*, National Committee for Clinical Laboratory Standards, Wayne, PA, (1993); abstract, title page, and publisher's page, table of contents only: 9 pages.

Kernodle et al., "Expression of an antisense *hla* fragment in *Staphylococcus aureus* reduces alpha–toxin production in vitro and attenuates lethal activity in a murine model," *Infect Immun*. Jan. 1997;65(1):179–84.

Konigsberg et al., "Evidence for use of rare codons in the dnaG gene and other regulatory genes of *Escherichia coli*," *Proc Natl Acad Sci U S A*. Feb. 1983;80(3):687–91.

Kreiswirth et al., "The toxic shock syndrome exotoxin structural gene is not detectably transmitted by a prophage," *Nature*. Oct. 20–26, 1983; 305(5936):709–12.

LaVallie et al., "A thioredoxin gene fusion expression system that circumvents inclusion body formation in the *E. coli* cytoplasm," *Bio/Technology (N Y)*. Feb. 1993;11(2):187–93.

Locksley, "Staphylococcal infections," *Harrison's Principles of Internal Medicine, 13th ed.*, Isselbacher et al., eds., McGraw–Hill, New York, NY (1994), pp. 611–617.

National Institutes of Health, "BLAST 2 Sequences," [online] United States; retrieved Jan. 18, 2002 from the Internet: <URL:http://www.ncbi.nlm.nih.gov/gorf/bl2.html>, 1 pg.

Novick et al., "Small *Staphylococcus aureus* plasmids are transduced as linear multimers that are formed and resolved by replicative processes," *J Mol Biol*. Nov. 20, 1986;192(2):209–20.

Sambrook et al., *Molecular Cloning: A Laboratory Manual*, Cold Spring Harbor Laboratory Press, Cold Spring Harbor, NY; title page, publisher's page, table of contents, pp. A1–A4 and p. B20 (1989).

Schmidt et al., "The random peptide library–assisted engineering of a C–terminal affinity peptide, useful for the detection and purification of a functional Ig Fv fragment," *Protein Eng*. Jan. 1993;6(1):109–22.

Smith et al., "Single–step purification of polypeptides expressed in *Escherichia coli* as fusions with glutathione S–transferase," *Gene*. Jul. 15, 1988;67(1):31–40.

Tatusova et al., "BLAST 2 Sequences, a new tool for comparing protein and nucleotide sequences," *FEMS Microbiol Lett*. May 15, 1999;174(2):247–50.

Tegmark et al., "Identification and characterization of SarH1, a new global regulator of virulence gene expression in *Staphylococcus aureus*," *Mol. Microbiol*. Jul. 2000;37(2):398–409.

Wieboldt et al., "Immunoaffinity ultrafiltration with ion spray HPLC/MS for screening small–molecule libraries," *Anal Chem*. 1997;69(9):1683–1691.

Lazar et al., "Transforming growth factor alpha: mutation of aspartic acid 47 and leucine 48 results in different biological activities," *Mol Cell Biol*. Mar. 1988;8(3):1247–1252.

Rudinger, "Characteristics of the amino acids as components of a peptide hormone sequence," in Peptide Hormones, Parsons, Ed., pp. 1–5 (1976), University Park Press.

Russell et al., "Structural features can be unconserved in proteins with similar folds. An analysis of side–chain to side–chain contacts secondary structure and accessibility," *J Mol Biol*. Dec. 2, 1994;244(3):332–350.

Wells et al., "The chemokine information source: identification and characterization of novel chemokines using the WorldWideWeb and expressed sequence tag databases," *J Leukoc Biol*. May 1997;61(5):545–550.

* cited by examiner nucleotide sequence
Seq. ID No: 1

```
  1 ATGTATTTAC TTACCTCCAA AATATTGTTA TTATAATTGT ACCGGTTCAA TTTGTAAACG CCGATACAAT TATAATATTT TGTGCTATAA TAATTACAGA CAAAGTGAAA
101 ACGAGGACAG AATATTGTTA AAAGAACGTT ATCAAGTAAG TAAGAGTACT ATCATTAAAG GCAACTTAAT GCGTTTATAC GGGTTTATAC ATCAATCTAA TTTCAAACCC GGTGATAAAT TGCCAAGCGT
201 GACGCAATTA AAAGAACGTT ATCAAGTAAG TAAGAGTACT ATCATTAAAG TGCTGATGCC AATCGTATCA ACGTCTTTAA ATTGGAACAA GACTAATGGT TTCTCTAAAA GTTTAGGTGA TACCGTCTAC TATTAGAGC GATAAGATT
301 GGTATTTATG TGAGAAATAT TGCTGATGCC AATCGTATCA ACGTCTTTAA ATGCAGATGA CTCCAATTAA ATGCAGATGA TTTAAATGAT GATATTGCTA CTTCGACTAT
401 TACTTGTTTT TAAGGAGATT GATGTTTTAT GCAACGCCAC GTATCGAATA CTAAATCTGT ACAAGATGAG CATAAAGAAA TGTGAAATA CTCACTTCAA CTCACTTCAA GTGAAGCTTC ATTACTACAA TTGTCTACAG
501 CGTGGACGAT GATGTTTTAT GCAACGCCAC GTATCGAATA CTAAATCTGT ACAAGATGAG CATAAAGAAA TTTTCTTTAA TGTAGATCAA CCCTTTGATT CATCTGACAT CGTATTCAT TATCGTCATG CACAGTTTA
601 TTAGAATCAA ACATGAAACT TCGTATTGGT TTTCAGATA TTTTCTTTAA TGTAGATCAA CCCTTTGATT CATCTGACAT CGTATTTCAT TATCGTCATG CACAGTTTA
701 GTGAACCATG TTTACGTTAC CACCAGACTT TTTATACAAT GACTGGCAAA
801 TATTCCTAGT AAAAAGTAA
``` peptide sequence
Seq. ID No: 2

```
  1 MYLLTSNYNC TGSICKRRYN YNILCYNNYR QSENEDRILL KYEHIAKQLN AFIHQSNFKP GDKLPSVTQL KERYQVSKST IIKALGLLEQ DGLIYQAQGS
101 GIYVRNIADA NRINVFKTNG FSKSLGEHRM TSKVLVFKEI ATPPKSVQDE LQLNADDTVY YLERLRFVDD DVLCIEYSYY HKEIVKYLND DIAKGSIFDY
201 LESNMKLRIG FSDIFFNVDQ LTSSEASLLQ LSTGEPCLRY HQTFYTMTGK PFDSSDIVFH YRHAQFYIPS KK
```

CCT47 5'ATATATCTGCAGTGATAAATTGCCAAGCGTGAC Seq. ID No: 25
CCT48 5'ATATATGAGCTCTCTTGTACAGATTAGGTGGC Seq. ID No: 26

*Fig. 1a* nucleotide sequence
Seq. ID No: 3

```
  1 ATGGCACTTT ATGGATTTGC CCAAGGACTT ATTCAAGAAG CAGGAATTAG AATTAAACAA AAAATTTAAC AATTGAAACA AAGTCAAATC
101 CGAATGACCT TGTTACAAAT GTAGATAAAG GTAGATAAGA CAACAGAAGA TTTCATTTTT GATACAATTT TCCCAATCAT CAAGTATTAG GTGAAGAAGG
201 GCATGGTCAT GACATCGATA CTTCCAAAGG TACGGTATGG ATTGTTGACC CAATAGACGG TACATTGAAT TTTGTTCATC AACAAGAAAA TTTCGCAATT
301 TCAATTGGTA TTTATATCGA TGTAAACCT TGGCAGGTT TTGTATATGA TACACAATTA GATGTCTTAT ATCATGCTAA AGTAGGGGAA GGTGCATATC
401 GTGTAGCCA ACCCTTGAAA ATTCTAATCT AAGACAAAGC ATTATTGGGA TGTTATGGCT AAGCAAAGC CTGGTTAACT AAACCAATTT TAGGAGAAAT
501 CTTTAAAGAA ATTGTTAATG TCAAGGGCA TATGGTAGTG CAGCGCTTGA AATCGTTTCA GTTGCTACAG GTAATTTAGA AGCATATATG
601 ACGCCAAGAC TTCAACCATG GGATTTTGCT ATTCTAGAAG TTATTTATA TGAAGTAAAT GGACAAGCTT CCAATTTACT AGGAGGACCA TTAACAATTA
701 GTGGTCCAAA TTCAATCTTA GTTGAAAATC GGCGGATTGG TCAAGAAATT AGCAATGATT ATTTAGAGCC CCACCATGAT GCGTTAATAC AATTACATGA
801 ACAACGATTT AAAGAAAAT CAAAATAA
``` peptide sequence
Seq. ID No: 4

```
  1 MALYGFAQGL IQEAGIRIKQ LMEQNLTIET KSNPNDLVTN VDKATEDFIF DTILETYPNH QVLGEEGHGH DIDTSKGTVM IVDPIDGTLN FVHQQENFAI
101 SIGIYIDVKP YAGFVYDVMA DVLYHAKVGE GAYRGSQPLK PLNDSNLRQS IIGINPNWLT KPILGEIFKE SNDYLEPHHD IVNDSRSARA YGSAALEIVS VATGNLEAYM
201 TPRLQPWDFA GGLVILYEVN GQASNLLGGP LTISGPNSIL VGNRGLHQEI ALIQLHEQRF KRKSK*
```

CCT87 ATATATCTGCAGCAAGTATTAGTGAAGAAGGG     Seq. ID No: 27
CCT88 ATATATGAGCTCACGGATTGATCCCAATAATGC    Seq. ID No: 28

*Fig. 1b* nucleotide sequence
Seq. ID No. 5

```
  1 ATGGGATTCA AAAACAATTT AACATCAAAT TTAACAAATA AAATCGGTAA TTCAGTCTTT AAAATAGAAA ATGTTGACGG AAAAGGTGCA ATGCCAACGA
101 CGATTCAAGA ATTGAGAGAA GTGCTGAAGC AGACGACAAC AATTGTAAAG AGAAAGTCTT TAATGTCATC AACAATGAGC GTTGTTCCAA TTCCGGGTTT
201 AGATTTGGT GTTGATTTAA AATTAATGAA AGATATTATC GAAGATGTTA ATAAAATTTA TGGTTTAGAT CATAAGCAAG TTAATAGCCT TGGGGATGAT
301 GTGAAAGAAA GAATTATGTC TGCAGCAGCA ATTCAAGGTA GTCAATTTAT TGGTAAAAGA ATTTCAAATG CATTTTTAAA AATTGTAATT AGAGATGTAG
401 CTAAACGTAC TGCTGCAAAA CAAACAAAAT GGTTTCCTGT TGTAGGACAA GCTGTGTCTG CATCTATTAG TTACTATTTT ATGAATAAAA TTGAAAAGA
501 TCACATTCAA AAATGCGAAA ATGTTATTAA AAATGTCATG TAG
``` peptide sequence
Seq. ID No. 6

```
  1 MGFKNNLTSN LTNKIGNSVF KIENVDGKGA MPTTIQELRE RRQRAEAIVK RKSLMSSTMS VVPIPGLDFG VDLKLMKDII EDVNKIYGLD HKQVNSLGDD
101 VKERIMSAAA IQGSQFIGKR ISNAFLKIVI RDVAKRTAAK QTKWFPVVGQ AVSASISYYF MNKIGKDHIQ KCENVIKNVM*
```

CCT139 5'ATATATCTGCAGGGGATTCAAAAACAATTTAACATC Seq. ID No. 29
CCT140 5'ATATATGAGCTCAAGGCTATTAACTTGCTTATGATC Seq. ID No. 30

*Fig. 1c* nucleotide sequence
Seq. ID No. 7

```
   1 ATGTTCATGG GAGAATACGA TCATCAATTA GATACAAAAG GACGTATGAT TATACCGTCC AAGTTTCGTT ATGACTTAAA TGAGCGTTTT ATTATCACAA
 101 GAGGCCTTGA TAAATGTTTA TTCGGTTACA CTCTAGACGA ATGGCAACAG ATTGAAGAGA AAATGAAAAC CTTACCTATG ACAAAAAAAG ACGCACGTAA
 201 GTTTATGCGT ATGTTCTTCT CTGGTGCTGT CGTAGTAGAA CTTGATAAGC AAGGGCGTAT CAAAACTTGA GGAAATACGC TAATTAACT
 301 AAAGAATGTA CAGTAATCGG TGTTTCAAAT CGTATTGAGA TTTGGGATAG AGAAACTTGG AGAATTTCT ATGAAGAATC TGAAGAAAGT TTCGAAGATA
 401 TTGCTGAAGA TTTAATAGAT TTTSATTTTY AAAATGGAGG AATTGAAGTG TTTCATCATA GTTAAACGAA ACCATTGATT ATTTAAATGT
 501 AAAAGAAAAT GGTGTGTACA TTGACTGTAC GCTAGGTGGA GCGGGACATG CCCTTTATTT ACTAAATCAA TTAAATGACG ACGGAAGATT AATAGCAATC
 601 GATCAAGACC AAACTGCAAT TGATAATGCT AAAGGAGTAT TTGTTCATAA TGACTTTTG TTCATAGCAA CTTCCGTGAA TTAACTCAAA
 701 TATTAAAGA CTTAAACATT GAAAAAGTAG ATGGAATTA CCAAACACAA GCCCACAACT CGACATTCCA GAACGAGGAT TCAGTTATCA
 801 CCATGACGCA ACATTAGACA TGCCTATGGA ATTTCAAAA CAGATAGCTC GAAGAATCGA AGCACATCGC TGTTAACAAT AAGCGTTAGT GAAGATTTT
 901 TATCGCTATG GCGAGAGAA AGTATTCCT GCAAAAGCAA CGGACATCCT GCAAAACGAG TATTTCAAGC AACATTAGAA TTAGTTGACA
1001 TTATAAAGA GATTCAATAG AACAAGCGAT TGAATTAGTG GCAGGATTTC GCTAATCACT TTCCATTCTT TAGAAGATCG ATGAATTGTC
1101 AGCTTTTGAA AAGAAGGTCCA GAGGTACCAA GAGTATACCA GAAGCATATA CACCTAAGTT AAAGCGTGTT TTATGTAAA
1201 CAGGTGTTCC QIAATATGA CGTAGCTGA AATACTTAAA TAA
1301 CGATTACCGC TACAGAAGAA GATTAGAGAT ACAATAACAG
1401
``` peptide sequence
Seq. ID No. 8

```
   1 MFMGEYDHQL DTKGRMIIPS KFRYDLNERF IITRGLDKCL FGYTLDEWQQ IEEKMKTLPM TKKDARKFMR MFFSGAVEVE LDKQGRINIP QNLRKYANLT
 101 KECTVIGVSN RIEIWDRETW NDFYEESEES FEDIAEDLID FXFXNGGIEV FHHISVMLNE TIDYLNVKEN GVYIDCTLGG AGHALYLLNQ LNDDGRLIAI
 201 DQDQTAIDNA KEVLKDHLHK VTFVHSNFRE LTQILKDLNI EKVDGIYYDL GVSSPQLDIP ERGFSYHHDA TLDMRMDQTQ ELTAYEIVNN WSYEALVKIF
 301 YRYGEEKFSK QIARRIEAHR EQQPITTLE LVDIIKEGIP AKARRKGGHP AKRVFQALRI AVNDELSAFE DSIEQAIELV KVDGRISVIT FHSLEDRLCK
 401 QVFQEYEKGP EVPRGLPVIP EAYTPKLKRV NRKPITATEE DLDDNNRARS AKLRVAEILK
```

CCT141 5'ATAGATCTGCAGAAGTGTTTCATCATATCAGCG Seq. ID No. 31
CCT142 5'ATATATGAGCTCACCCAAGTCGTAATAAATTCC Seq. ID No. 32

*Fig. 1d* nucleotide sequence

Seq. ID No. 9

```
  1 ATGATAAATA ATCATGAATT ACTAGTATT  AAAGACAGTC AATCAAGATG CACCATGTTA CTGCAATGAC AGATGATGCA GAACGTAATT ATAAATTTTT TACAGAAGTA CTAGGCATGC
101 GTTTAGTTAA AAAGACAGTC AATCAAGATG GGCAGGCAGG AACAAATTCC ATATTTATAC GTATCATACT TTTTTTGCAG ATGATGTAGG TTCGGCAGGT ACAGACATGA CGTTCTTTGA
201 TTTTCCAAAT ATTACAAAAG GGCAGGCAGG AACAAATTCC ATTCAAGAAT TATTGGTAA  ATTACAAGAC CGTCTTTTAG ATGCCTAAC  AGTGCCTAAC AGTGACGCAT TGAACAGCGC
301 TTTGATGAGT TTGGTGTTAA ACACGAAGGT ATTCAAGAAT TATTGGTAA  AAAAGTGTTG CCATTTGAAG AAGTCGATGG GATTTATGGA CCAAGTGTAT CAATTAATTT
401 CAGATGAGTT AAATGAAGGG GTAGCACCTG GTGTACCTTG GAAGAATGGA CCGGTTCCAG TAGATAAAGC GATTTATGCG TTAGGCCCCA TTGAAATTAA
501 AGTAAGTTAT TTTGACGACT TTAAAAATAT TTTTACGGTA GTTTACGGTA GTTACGGTA TGACAACTAT TGCGCATGAA GATAATGTCG CATTACTTGA AGTTGGCGAA
601 GGAGGCAATG GTGGCCAGGT AATCTTAATA AAGATGATA  AAGGGCCAGC GGTTATGGTG AGGTACATCA TGTGTCATTT CGTGTGAAAG
701 ATCATGATGC AATAGAAGCG TGGGCAACGA AATATAAAGA GGTAGGTATT AATAACTCAG GCATCGTTAA TCGTTTCTAT TTTGAAGCAT TATATGCACG
801 TGTGGGGCAT ATTTTAATAG AAATTTCAAC AGATGGACCA GGATTTATGG AAGATGAACC TTATGAAACA TTAGGCGAAG GGTTATCCTT ACCACCATTT
901 TTAGAAAATA TATTGAATCG GAAGTTAGAC CTTTTAATAC GAAGCGTCAA CATGGTTAA
``` peptide sequence

Seq. ID No. 10

```
  1 MINNHELLGI HHVTAMTDDA ERNYKFFTEV LGMRLVKKTV NQDDIYTHT  FFADDVGSAG TDMTFFDFPN ITKGQAGTNS ITRPSFRVPN DDALTYYEQR
101 FDEFGVKHEG IQELFGKKVL PFEEVDGQVY QLISDELNEG VAPGVPMKNG PVPVDKAIYG LGPIEIKVSY FDDFKNILET VYGMTTIAHE DNVALLEVGE
201 GGNGGQVILI KDDKGPAARQ GYGEVHHVSF RVKDHDAIEA WATKYKEVGI NNSGIVNRFY FEALYARVGH ILIEISTDGP GFMEDEPYET LGEGLSLPPF
301 LENKREYIES EVRPFNTKRQ HG
```

CCT155 5'ATATATCTGCAGAGGTATTCACCATGTTACTGC Seq. ID No. 33
CCT156 5'ATATATGAGCTCAATTGATACACTTGGCCATCG Seq. ID No. 34

*Fig. 1e* nucleotide sequence
Seq. ID No. 11

```
ATGATAAATA ATCATGAATT ACTAGGTATT CACCATGTTA CTGCAATGAC AGATGATGCA GAACGTAATT ATAAATTTTT TACAGAAGTA CTAGGCATGC
GTTAGTTAA AAAGACAGTC AATCAAGATG GTATCATACT TTTTTTGCAG ATGATGTAGG TTCGGCAGGT ACAGACATGA CGTTCTTTGA
TTTCCAAAT ATTACAAAAG GGCAGGCAGG AACAAATTCC ATTACAAGAC CGTCTTTTAG AGTGCCTAAC GATGACGCAT TAACATATTA TGAACAGCGC
TTTGATGAGT TTGGTGTTAA ACACGAAGGT ATTCAAGAAT TATTGGTAA AAAAGTGTTG CCATTGAAAG AAGTCGATGG CCAAGTGTAT CAATTAATTT
CAGATGAGTT AAATGAAGGG GTAGCACCTG GTTACCCTTG GAAGAATGGA CCGGTTCCAG TAGATAAAGC GATTATTGGA TTAGGCCCCA TTGAAATTAA
AGTAAGTTAT TTTGACGACT TTAAAAATAT TTTAGAGACT TGACAACTAT GTTTACGGTA TGCGCATGAA GATAATGTCG CATTACTTGA AGTTGGCGAA
GGAGGCAATG GTGGCCAGGT AATCTTAATA AAGATAAAGA AAGGGCCAGC AGCACGTCAA GGTTATGGTG AGGTACATCA TGTGTCATTT CGTGTGAAAG
ATCATGATGC AATAGAAGCG TGGGCAACGA AATATAAAGA GGTAGGTATT AATAACTCAG GCATCGTTAA TCGTTTCTAT TTTGAAGCAT TATATGCACG
TGTGGGGCAT ATTTTAATAG AAATTTCAAC AGATGGACCA GGATTATGG AAGATGAACC TTATGAAACA TTAGGCGAAG GGTTATCCTT ACCACCATTT
TTAGAAAATA AAAGAGAATA TATTGAATCG GAAGTTAGAC CTTTTAATAC GAAGCGTCAA CATGGTTAA
``` peptide sequence
 Seq. ID No. 12

```
  1 MINNHELLGI HHVTAMTDDA ERNYKFFTEV LGMRLVKKTV NQDDIYTYHT FFADDVGSAG TDMTFFDFPN ITKGQAGTNS ITRPSFRVPN DDALTYYEQR
101 FDEFGVKHEG IQELFGKKVL PFEEVDGQVY PVPVDKAIYG LGPIEIKVSY FDDFKNILET VYGMTTIAHE DNVALLEVGE
201 GGNGGQVILI KDDKGPAARQ GYGEVHHVSF RVKDHDAIEA WATKYKEVGI NNSGIVNRFY FEALYARVGH ILIEISTDGP GFMEDEPYET LGEGLSLPPF
301 LENKREYIES EVRPFNTKRQ HG
```

CCT155 5′ ATATATCTGCAGAGGTATTCACCATGTTACTGC Seq. ID No. 35
CCT156 5′ ATATATGAGCTCAATTGATACACTTGGCCATCG Seq. ID No. 36

*Fig. 1f* nucleotide sequence

Seq. ID No. 13

```
     GGGACATTTTAAATCATGC
   1 ATGCGTATCT TAAAAGAGTC CATTATTGTG GCATTTGCCT TTGTTGGTGT TGTCGTTGGT GCCGGCTTTG CTACTGGTCA AGAAATTTTC CAGTTTTTCA
 101 CAAGTCATGG CGCATATAGC TCTGATTCAA ATTTCAGGCA TTATTGTAAC AGGACTATTG ATTACTTTAG GTGGAATGGT TGTCATGCAT ACAGGTCATC ATCTAAAGTC
 201 CAGAAATCAT TCTGATTCAA CAAGTTTTCA CTTATACCCC TCTATTGCAA GAGGTTTTGA TATTATTTTA ACAATGTTTA TGTTGTCTTT AGCTATTATT
 301 ATGACTGCAG GTGGTGCGTC AACCATTCAT GCTGTGCTTG GCGGTGTTAC CCCATTTTTA ATTGCGATTG TCATTATGAT TAGTCGCCTT TATTTTAGCA ACACTGTTTC
 401 TAAAATTCGA TCGTTTAATT GCCGCTAATA ATGATGCTCA CAGAAATCAT TATCACCTGG ATGGTGGTTT TGGGTCTAC TATTTCACAA CAAGTCATCT
 501 TGATTTTACT GCCGCTAATA ATGATGCTCA CAGAAATCAT TATCACCTGG ATGGTGGTTT ATGGTGGTTT TGGGTCGATTA ACTACGCAAG CTTGCAAATT
 601 GCTGCTGCCT TCAGCTTCTT ATCAGTGATG GTAGTAAAG TTAACTCAACG TGACTCAACG TTAACTAACG GCTTGATTGG CGGTTTAATC ATTACATTTT
 701 TACTCATGAT GATTAATCTA GGTTTAATTT CTCAATTCGA TGTCATCTAA CACGTAGATC TACCTACATT AAAATTAGCG ACACAAATGT CTCCGTCAAT
 801 TGGTATTATT ATGTCTGTCA TTATGATACT TGTCATCACT ATATTATGTG TTGGATTAAT ATTATCGGT TTCATTTCAT GGTCACGTT TAATTGGAAA ATTATGGGAT
 901 CGTTACTTCA TCATTATTAT TACACCTGTAC ATATTAGTAC ATTATCGGT CGTATTACCG GCAAATCTCA TAATTGGAAA AGTATTCCCT ATTATGGGAT
1001 TGTTCGGTTT CATCTTACTC TCTATAAAGG TTTAATTAAG
``` peptide sequence

Seq. ID No. 14

```
  1 MRILKESIIV AFAFVGVVVG AGFATGQEIF QFFTSHGAYS ISGIIVTGLL ITLGGMVVMH SDSINYFLYP SIARGFDIIL TMFMLSLAII
101 MTAGGASTIH QSFNLPYWLS GSKVKYRDST ALLIVAFILA TLFLKFDRLI IAIVIMIAVY YFTTSHLDFT AANNDAQIHK QKSLSPGWMF DAINYASLQI
201 AAAFSFLSVM GSKVKYRDST LYGGLIGLI ITFLLMMINL GLISQFDKIK HVDLPTLKLA TQMSPSIGII MSVIMLVIY NTVVGLMYAF ASRFSVPFSR
301 RYFIIITMA VITYISTFIG FISLIGKVFP IMGLFGFILL IPVLYKGLIK RITGKSHID
```

CCT153 5'ATATATCTGCAGGGGACATTTTAATCATGCATGC Seq. ID No. 37
CCT154 5'ATATATGAGCTCGCAGTCATAATAATAGCTAAAGAC Seq. ID No. 38

*Fig. 1g* nucleotide sequence
Seq. ID No. 17

```
   1 ATGATAATAT ATTGGTGTAT GACAGTTAAT GGAGGGAACG AAATGAAAGC TTTATTACTT AAAACAAGTG TATGGCTCGT TTTGCTTTTT AGTGTAATGG
 101 GATTATGGCA AGTCTGAAGC GCGGCTGAGC ATCATTCTGG AGCATACACC AATGAAAGCA CATGCAGTAA CAAGCAACA CAAAGCAACA ACAGATAAGC AACAAGTACC
 201 GCCAACAAAG GAAGGGCTC ATCATCTACA ACCATCCAAG CAAAGAAGCG GCAACCAAG TATCAGCATC CGAACACGC AGCAGCTGATG ACACTGATG ATACAAACAG CAAAGTAACA
 301 TCCAACGCAC CATCTAACAA GTAGTTTCAA AAACAGCATC ACTTTCACCA CGAATGTTTG CTGCTAATGC ATTAAAAACA GACGTAGATA CACCAACAAG CTCAACACAA ACACACATA AAATATTACA
 401 ACACAGCAAC GTTCAAATTA TCAAATGAT AGAAAAAGG AGAAAAAGGG CGTGTCATCG GTATGCTAA AGGCTAAAG ATGGCTAAAG CAATGAATGC AGTAGGTTAT TGATTTAATG
 501 TACAAATGAT GAGACGCCTT GACTAGCCGA CCAAGGTTTA CCACTTTCAA AGGTGAAGAA ATGGCTAAAG ATGGCTAAAG TAGACTTCC GATGCTAAGT ACTAACGTTT GATGCTATGG
 601 TTAGACGCAG CCATGAATTT CCAAGGTTGA AGGTGAAGAA CCAAGGTTGA ACGATCAGTT GAAAAAGTTA GAGGGTATGT TAGACTTCCC GATGCTAAGT ACTAACGTTT ATAAAGATGG
 701 CAGTCGGTAA CCTTTAAGCTT CAACGATTGT AACGATTAT CCATTAAAAAT GGTATTCGTT ATGGAATTAT TGGTGTAACG ACACCAGAA CAAGACGAA AACAAGACCT
 801 AAAACGCGCG GAAGGCATTA AAGGCGTTGA ATTAGAGAT GTGTGACAGC GAAATGATG CGTATTTATA AGAACGTAGA TACATTTGTT GTTATATCAC
 901 GAAGGCATTA ATTTAGGAAT TGATCCTTCA ACACAAGAAA CATGGCGTGG TAAGCAATTG TCCACAATTG AAGAACGTAA TACAGTTAT
1001 ATTTAGGAAT TGATGTCAT TCACATACAG TACTTCAAAA TGGTCAAATT TGATTACTTA GTGAACAAT TGTAAGCAA AACAGGTTG ACACACTTG CGAATATCG TAAGATTACA
1101 TTGATGTCAT GCAATGAGA GGTATCGAAT AAACTGCGAT CATGATTAA TGTTAAAGAC GTTAAAAATG TAACACCGAA CAAAGACTTG ACACACTTG GCTAAACGCG
1201 TTTAATTATC GCAATGAGA TTTAGACGAC TGATCGAA CATGATTAA TGTTAAAGAC GTTAAAAATG TAACACCGAA CAAAGGAGAA AGAGATGACG TTAGACGCG
1301 TTAATCAAGC TGATCAAACA AAACTGCGAA TGCTATGCGA GGTAATTAAT CCAAACAATA ATTTAAAAG ACTGACTTTG CCGTGACAAA TGGTGGAGGT
1401 TGAAACAAAT TTAGGAAACG CGATTGCGAA TGCTATGCGA ATTTAATCTC AGTATTACCA CAGTGTTAAC CGATTGCGCA AATTGATGTA AAAGGTTCAG
1501 ATTCGTGCCT CTATCGCAAA AGGTAAGGTG ACACGCTATG ATTTAATCTC AGTATTACCA GACGGTAAGA AGCGAATGGC GGTTTACTAC ATATCTCTGA
1601 ACGTCTGGAC GGCTTTCGAA CATAGTTTAG GCGCACCAAC AAACACAAAG ATGCTATTCA AATTTAAAT AAGAGACAG GTAAGTTTGA AATATTGAT
1701 TTCAATCCGT GTTACTATG ATATAAATAA ACCGTCTGGC CATCAGGTGG CATCAGAATTA GTATGTTCGG TGTCCTAGA GAAGAAGTA TTTCATTAGA
1801 TTAAAACGTG TATATCACGT AACGATGAAT GACTTCACAG AAGTATGATA CGACAGAACC ACACGTATG TTATTAGTTA AACCAGCAGT AAGTGAACAA
1901 TCAAGTACTA GCAAGTTATT TAACTAGCT AAAAACAGC TAACGATGAAT TAAGACAATAC ACACACCAATT GGTGACGACA AAGTGATGA TCCAGCAGAA AAACCAGCTC
2001 CCAGCTAAAG GACAACAAGG AGTAAGTCTG
2101 CAGGTAAAGT TGTATTGTTG TAG
``` peptide sequence
Seq. ID No. 18

```
  1 MIIYWCMTVN GGNEMKALLL KTSVWLVLLF SVMGLMQVSN AAEQHTPMKA HAVTTIDKAT TDKQQVPPTK EAAHHSGKEA ATNVSASAQG TADDTNSKVT
101 SNAPSNKPST VVSTKVNETR DVDTQQASTQ KPTHTATFKL SNAKTASLSP RMFAANAPQT TTHKILHTND IHGRLAEEKG RVIGMAKLKT VKEQEKPDLM
201 LDAGDAFQGL PLSNQSKGEE DAMAVGNHEF DFGYDQLKKL EGMLDFPMLS TNVYKDGKRA FKPSTIVTKN GIRYGIIGVT TPETKTKTRP
301 EGIKGVEFRD PLQSVTAEMM RIYKDVDTFV VISHLGIDPS TQETWRGDYL VKQLSQNPQL KKRITVIDGH SHTVLQNGQI YNNDALAQTG TALANIGKIT
401 FNYRNGEVSN IKPSLINVKD VENVTPNKAL AEQINQADQT FRAQTAEVII PNNTIDFKGE RDDVRTRETN LGNAIADAME AYGVKNFSKK TDFAVTNGGG
501 IRASIAKGKV TRYDLISVLP FGNTIAQIDV KGSDVWTAFE HSLGAPTTQK DGKTVLTANG GLLHISDSIR VYYDINKPSG KRINAIQILN KETGKFENID
```

Fig. 1i-1

601 LKRVYHVTMN DFTASGGDGY SMFGGPREEG ISLDQVLASY LKTANLAKYD TTEPQRMLLG KPAVSEQPAK GQQGSKGSKS GKDTQPIGDD KVMDPAKKPA
701 PGKVVLL

CCT171 5'ATATATCTGCAGACAAGTGTATGGCTCGTTTTG Seq. ID No. 41
CCT172 5'ATATATGAGCTCATTGAACGTTGCTGTGTGAG Seq. ID No. 42

*Fig. 1i-2* nucleotide sequence
Seq. ID No. 15

```
  1 ATGTTAATCG ATACACATGT CCATTAAAT  GATGAGCAAT ACGATGATGA TTTGAGTGAA GTGATTACAC AGCAGGTGTT GATCGTATGT
101 TTGTAGTTGG TTTTAACAAA TCGACAATTG AACGCGCGAT TTAGCTCAGC GATGAGTATG ATCCAAAAGT ATTTTTTATA GGTTGGCATC CAGTTGACGC
201 AATTGATTTT ACAGAAGAAC ACTTGGAATG GATTGAATCT TTAGCTCAGC AAATTGCTTT AGCTAAGCGT GATTGGTATT GGTGAAATGG GATTAGATTA TCACTGGGAT
301 AAATCTCCTG CAGATGTTCA AAGGAAGTT TTGGAGGAGC ATGCTGAAGA GCTTTAGTGG GCTTTAGTGT TTGAAGTTAC CAATTATCAT TCATAACCGT GAAGCAACTC
401 AAGACTGTAT CGATATCTTA TTGGAGGAGC ATGCTGAAGA ACCTGTGACA GGTAGGCGGA ATTATGCATA TTCTCCAGAA ATTGCAGATA TTGTAACTAA
501 TAAGCTGAAT TTTTATATTT CATTAGGTGG ACCTGTGACA TCTTTCGCCA TTTAAAAATG CTAAACAGCC TAAAGAAGTT GCTAAGCATG TGTCAATGGA GCGTTTGCTA
601 GTTGAAACCG ATGCACCGTA TCTTTCGCCA CATCCGTATA GAGGGAAGCG AAATGAACCG GCGAGAGTAA CTTTAGTAGC TGAACAAATT GCTGAATTAA
701 AAGGCTTATC TTATGAAGAA GTGTGCGAAC AAACAACTAA AAATGCAGAG AAATTGTTTA ATTTAAATTC ATAA
``` peptide sequence
Seq. ID No. 16

```
  1 MLIDTHVHLN DEQYDDDLSE VITRAREAGV DRMFVVGFNK STIERAMKLI DEYDFLYGII GWMHPVDAIDF TEEHLEWIES LAQHPKVIGI GEMGLDYHWD
101 KSPADVQKEV FRKQIALAKR LKLPIIHNR EATQDCIDIL LEEHAEEVGG IMHSFSGSPE IADIVTNKLN FYISLGGPVT FKNAKQPKEV AKHVSMERLL
201 VETDAPYLSP HPYRGKRNEP ARVTLVAEQI AELKGLSYEE VCEQTTKNAE KLFNLNS
```

CCT157 5' ATATATCTGCAGTGTTAATCGATACACATGTCC  Seq. ID No. 39
CCT158 5' ATATATGAGCTCCTTCAAACGCTTAGCTAAAGC  Seq. ID No. 40

*Fig. 1h* nucleotide sequence
Seq. ID No. 19

```
  1 ATGGATAATA ATGAAAAAGA AAAAAGTAAA AGTGAACTAT TAGTTGTAAC AGTTTATCT GGGCCAGGTA AATCTTTGGT TATTCAATGT TTAGAAGACA
101 TGGGATATTT TTGTGTAGAT AATCTACCAC AACTATTTAA TTCATTAGTT GCCTAAATTT GTAGAGTTGA TGGAACAAGG AAATCCATCC TTAAGAAAAG TGGCAATTGC
201 AATTGATTTA AGAGGTAAGG AACTATTTAA AAGGAAACGC GTCGTAGTGG ATAAAGTCAA AAGTGAAAGT GACGTCATCA TTGATGTTAT GTTTTAGAA
301 GCAAGTACTG AAAAATTAAT TTCAAGATAT AGCTAATT TCCTTTGATG GAACAAGGTA AAGATCGTT AATCAATGCA ATTAATGATG
401 AGCGAGAGCA TTTGTCTCAA ATTAGAAGTA TGTTACACA ACTACAAAGT TATCACCTAA AGAATAAAA GAACGCATTC GTCGATACTA
501 TGAAGATGAA GAGTTTACAA CTTTTACAAT AGTTTCGTT TTAAACATGG GATTCAGATG TAGTATTGA TGTACGATTT
601 TTACCAAATC CATATTATGT AGTAGATTTA AGACCTTTAA CAGGATTAGA AGGGGAAAT TATGAAATG GAAAGACG GAGATTTCT
701 TTGAAAAATT AACTGATTTG TTAGATTTTA TGATACCCGG GTATAAAAAA CTCAATTAGT AATGCCATC GGTTGTACGG GTGGACAACA
801 TCGATCTGTA GCATTAGCAG AACGACTAGG TAATTATCTA AATGAAGTAT TTGAATATAA TGTTTATGTG CATCATAGGG ACGCACATAT TGAAAGTGGC
901 GAGAAAAAT GA
``` peptide sequence
Seq. ID No. 20

```
  1 MDNNEKEKSK SELLVVTGLS GAGKSLVIQC LEDMGYFCVD NLPPVLLPKF VELMEQGNPS LRKVAIAIDL RGKELFNSLV AVVDKVKSES DVIIDVMFLE
101 ASTEKLISRY KETRRAHPLM EQGKRSLINA INDEREHLSQ IRSIANFVID TTKLSPKELK ERIRRYYEDE EFETFTINVT SFGFKHGIQM DADLVFDVRF
201 LPNPYYVVDL RPLTGLDKDV YNYVMKWKET EIFFEKLTDL LDFMIPGYKK EGKSQLVIAI GCTGGQHRSV ALAERLGNYL NEVFEYNVYV HHRDAHIESG
301 EKK
```

CCT179 5' ATATATATCTGCAGGTTGTAACAGGTTTATCTGGC Seq. ID No. 43
CCT180 5' ATATATGAGCTCATTTGAGACAAATGCTCTCGC Seq. ID No. 44

Fig. 1j nucleotide sequence
Seq. ID No. 21

```
   1 ATGCGATTTA CATTTTCAAA CGATTTAGGA ACGTTATTTA CTATTATTTT AGCCATTGGA TTCATCATTA ATTTAGTATT GGCTTTTATT ATTATCTTTT
 101 TAGAAAGAAA TAGGCGTACA GCGAGTTCAA CTTGGGCATG GCTATTTGTA CTTTTTGTCT ATTTCGATGG TGTTTATT CTTTACTTGT TTTTTGGTAG
 201 AACCGTTTCG GCACGCAAAT TGAATAAAAA CAATGGTAAC GTGTTAACGG ATTTCGATGG ACTTTTGAA AAAGCTTTGA AAAGGTAAT
 301 TATGGTACTG ATAACAAACA AGTTCAAAAA CATCATGATT TAGTACGTAT GCTTTTGATG GATCAAGATG GTTTTTTAAC TGAAAATAAT AAAGTTGATC
 401 ATTTCATTGA TGGAAATGAT TTATATGATC AAGTTTTAGA AGATATCCA AATGCAAAAG AATATATCCA TTTAGAGTAC TATACTTTCG CTTTAGATGG
 501 TTTAGGTAAA AGAATTTTAC ATGCTTTAGA AGAAGAGTTG AAGCAATTTT TGCTTCAAAA TTACCGTTAT GATGATGTTG GTAAGTGTTG TGTTAAGATG
 601 GCAAATTTTG ATCATTTTAA ATCGTTAGGT GTTATGTCGG AGATTAACAC ATTGGTGATG TGAATTTCAG AATGAATAAT AGAAATCATA
 701 GAAAATCAT CGTAACTGAT GGTCAACTAG TTGCACTGCAG TTGCGATTA CAATTCAAAT AATATCTAGG ATTAGGAAAA TTAGGATATT GGAGAGATAC
 801 GCATTACGT ATACAAGGGG ATGCGGTTGA TGCACTCCAG CAATTCAC GAATTGCAA GAATTCGCAA GCGCACCGTC CACAATTGA ATATGATGTT
 901 AAGTATTTCC CAATTTACGA AAGAAATCTG TATATTTACA ATCACCATAT CATCCATTAG GTTAGACTG TTTTAGACTG GGCCGGCTA TCAAATTGAA TACGGTTATA
1001 CAAAAATGAT TATGAGTGCA AAGAAAATCG TGATTCATG TAAGCCAGAT CATCCATTAG TGTGCTTAAT ATCGTATCCG GACATTTCA AATGCCTCTG ACTTATATC AAGTGGTGTT
1101 AGGTGTAGAT GTACATTTAA TGGATTTATA CATTCTAAAA TATATGATGA AAATCTTGCT AAAGATTTAA GGGTGGCTTA AATATGGAC ATTACAAAAT TTTAGAAGTT
1201 AAAATTTATA CGTATGAAAA AATGACCGCT TATATGATGA GTCTGTTAAA TTCAAAGAAT CGTTGTTAAA ATTAGTTTCG CCAATTTAT AA
1301 TTGAATTAAA TCATATGCCA AACCAAGAA ATAGACCGCT GTCTGTTAAA
``` peptide sequence
Seq. ID No. 22

MRFTFSNDLGTLFTIILAIGFIINLVLAFIIIFLERNRRTASSTWAMLFVLFVLPLIGFILYLFFGRTVSARKLNKNNGNVLTDFDGLLKQQIESFDKGNYGTDNKQVQKHHDLVRMLL
MDQDGFLTENNKVDHFIDGNDLYDQVLKDIKNAKEYIHLEYTFALDGLGKRIIHALEEKLKQGLEVKILYDDVGSKNVKMANFDHFKSLGGEVEAFFASKLPLLNFRMNNRHRKIIV
IDGQLGYVGGFNIGDEYLGLGKLGYWRDTHLRIQGDAVDALQLRFILDWNSQAHRPQFEYDVKYFPKKNGPLGNSPIQIAASGPASDWHQIEYGYTKMIMSAKKSVYLQSPYFIPDNSY
INAIKIAAKSGVDVHLMIPCKPDHPLVYWATFSNASDLLSSGVKIYTYENGFIHSKMCLIDDEIVSVGTANMDFRSFELNFEVNAFVYDENLAKDLRVAYEHDITKSKQLTKESYANRP
LSVKFKESLAKLVSPIL

CCT77 5'ATATATCTGCAGAGAGTACATACTTTCGCTTTAG Seq. ID No. 45
CCT78 5'ATATATGAGCTCCCTAATCCTAGATATTCATCAC Seq. ID No. 46

*Fig. 1k* nucleotide sequence
Seq. ID No. 23

```
  1 ATGAAGATTT TATTCGTTTG TACAGGTAAC ACATGTCGTA GCCCATTAGC GGAAAGTATT GCAAAAGAGG TTATGCCAAA TCATCAATTT GAATCAAGAG
101 GTATATTCGC TGTGAACAAT CAAGGTGTTT CGAATTATGT CGAATTATGT TGAAGACTTA GTTGAAGAAC ATCATTAGC TGAAACGACC TTATCGCAAC AATTACTGA
201 AGCAGATTTG AAAGCAGATA TTATTTGAC GATGTCGTAT TCGCACAAAG AATTAATAGA GGCACACTTT GGTTTGCAAA ATCATGTTTT CACATTGCAT
301 GAATATGTAA AAGAAGCAGG AGAAGTTATA AGAAGATGTAT GTGGAACAAA AGAAATGTAT GTACATACCT ATGAAGAACT TGTAAGTTTA ATTTTAAAAT
401 TAAAAGATAT TATTTGCTAG
``` protein sequence
Seq. ID No. 24

```
  1 MKILFVCTGN TCRSPLAESI AKEVMPNHQF ESRGIFAVNN QGVSNYVEDL VEEHHLAETT LSQQFTEADL KADILTMSY SHKELIEAHF GLQNHVFTLH
101 EYVKEAGEVI DPYGGTKEMY VHTYEELVSL ILKLKDIIC
```

CCT01A  5'ATATATCTGCAGTTGTACAGGTAACACATGTCG Seq. ID No. 47
CCT02A  5'ATATATGAGCTCCTGCTTTCAAATCTGCTCAG   Seq. ID No. 48

*Fig. 1l*

Expressed in pQE60

Seq. ID No. 49

ATGGGATTAAAGTATGAACATATTGCTAAGCAACTTAATGCGTTTATACATCAATCTAATTTCAAACCCGGTGATAAATTGCCAAGCGTGACGCAATTAAAAGAACGTTATCAAGTAAGT
AAGAGTACTATCATTAAAGCATTAGGCTTATTGGAACAAGATGTTTGATCTATCAAGCACAAGGCCAGTGTGTATTAATGTGAGAAATATTGCTGATGCCAATCGTATCAACGTCTTTAAG
ACTAATGGTTTCTCTAAAGTTAGGTGAACACCGAATGACAAGTTTTGTTTTAAGGAGATTGCAACGCCACCTAAATCGTACAAGATGAGCTCCAATTAAATGCAGATGAT
ACCGTCTACTATTTAGAGCGATTAAGATTCGTGGACGATGATGTTTTATGTATCGAATATTCTATTACATAAAGAAATCGTGAAATATTTAAATGATGATATTGCTAAGGCTCTATC
TTCGACTATTTAGAATCAAACATGAAACTTCGTATTGGTTTTTCAGATATTTTTCTTTAAGTAGATCAACTCACTTCAAGTGAAGCTTCATTACTACAATTGTCTACAGGTGAACCATGT
TTACGTTACCACCAGACTCTTTTATACAATGACTGGCAAACCCTTTGATTCATCTGACACTGTATTTCATTATCGTCATGCACAGTTTATATTCCTAGTAAAAAGAGATCTCATCACCAT
CACCATCACTAA

M.W. = 28.1 kd

Seq. ID No. 50
MGLKYEHIAKQLNAFIHQSNFKPGDKLPSVTQLKERYQVSKSTIIKALGLLEQDGLIYQAQGSGIYVRNIADANRINVFKTNGFSKSLGEHRMTSKVLVFKEIATPPKSVQDELQLNADD
TVYYLERLRFVDDDVLCIEYSYYHKEIVKYLNDDIAKGSIFDYLESNMKLRIGFSDIFFNVDQLTSSEASLLQLSTGEPCLRYHQTFYTMTGKPFDSSDIVFHYRHAQFYIPSKKRSHHH
HHH

Forward Primer*  5'- CCATGGGATTAAAGTATGAACATATTGCTAAGC Seq. ID No. 51
Reverse Primer   5'- GAGATCTCTTTTACTAGGAATATAAAACTGTGCATGACG Seq. ID No. 52

*Fig. 2a*

Expressed in pQE-70

Seq. ID No. 53
ATGCTGGCACTTATGGATTTGCCCAAGGACTTATTCAAGAAGACGAGGAATTAGAATTGAAACAAGTCAAATCCGAATGACCTGTTACA
AATGTAGATAAAGCAACAAGAAGATTTCATTTTGATACAATTTAGAAACATATCCAATCAAGTATTAGTGAAGAAGGCATGGTCATGACATCGATACTTCCAAAGGTACGGTA
TGGATTGTTGACCCAATAGACGGTACAAGTACTAAAGTGAATTCAATTTGTTCATCAACAAGAAAATTCGCAATTTCAAGGTATTTATATCGATGGTAAACCTATGCAGGTTTTGTATATGATGTTATG
GCTGATGTCTTATATCATGCTAAAGTAGGGAAGGTCAAATTCTAAACCATTGGATGATTCTAATCTAAGACAACATTATTGGGATGCAATTCGAACTGGTTA
ACTAAACCAATTTTAGGAGAAATCTTTAAAGAAATTGTTAATGATTCTAAGAAGTGTAGTCGCTTGAAATCGTTTCAGTTGCTACAGGTAATTTAGAAGCATAT
ATGACGCCAAGACTTCAACCATGGGATTTGCTGGCGGATTTGCTATTTATTAGAGCCCCACCATGATGCGTTAATACAATTACATGAACAACGATTTAAAGAAATCAAAAGATCTCATCA
TTAGTTGGAAATCGTGCTCTCCATCAAGAAATTAGCAATGATTATTTAGAGCCCCACCATGATGCGTTAATACAATTACATGAACAACGATTTAAAGAAATCAAAAGATCTCATCA
CCATCACCATCACTAA

M.W. = 31.6 kd
Seq. ID No. 54
MLALYGFAQGLIQEAGIRIKQLMEQNLTIETKSNPNDLVTNVDKATEDFIFDTILETYPNHQVLGEEGHGHDIDTSKGTVWIVDPIDGTLNFVHQQENFAISIGIYIDGKPYAGFVYDVM
ADVLYHAKVGEGAYRGSQPLKPLNDSNLRQSIIGINPNWLTKPILGEIFKEIVNDSRSARAYGSAALEIVSVATGNLEAYMTPRLQPWDFAGGLVILYEVNGQASNLLGGPLTISGPNSI
LVGNRGLHQEISNDYLEPHHDALIQLHEQRFKRKSKRSHHHHHH

Forward Primer* 5'- GCATGCTGGCACTTATGGATTTGCCCAAGG Seq. ID No. 55
Reverse Primer  5'- GAGAGTCTTTTGATTTCTTTTAAATCGTTGTTCATGATT Seq. ID No. 56

*Fig. 2b*

Expressed in pQE60

Seq. ID No. 57
ATGGGATTCAAAAACAATTAACATCAAATTTAACAATAAAATCGGTAATTCAGTCTTTAAAATAGAAAATGTTGACGGAAAAGGTGCAATGCCAACGACGATTCAAGAATTGAGAGAA
AGACGACAACGTGCTGAAGCAATTGTAAAGAGAAAGTCTTTAATGTCATCAACAATGAGCCGTTGTTCCAATCCGGGTTAGATTTGGTGTTGATTAAATAATGAAAGATATTATC
GAAGATGTTAATAAAATTTATGGTTTAGATCATAAGCAAGTTAATAGCCTTGGGGATGATGTGAAAGAAAGAATTATGTCTGCAGCAGCAATTCAAGGTAGTCAATTTATTGGTAAAGA
ATTTCAAATGCATTTTTAAAATTGTAATTAGAGATGTAGCTAAACGTACTGCTGCAAAACAAAATGGTTTCCTGTTGTAGGACAAGCTGTGTCTGCATCTATTAGTTACTATTTT
ATGAATAAAATTGGAAAAGATCACATTCAAAAATGCGAAAATGTCATTAAAAATGTTATTAATAAACATTCATGAGATCTCATCACCACCATCACTAA

M.W. = 28.5 kd
Seq. ID No. 58
MGFKNNLTSNLTNKIGNSVFKIENVDGKGAMPTTIQELRERRQRAEAIVKRKSLMSSTMSVVPIPGLDFGVDLKLMKDIIEDVNKIYGLDHKQVNSLGDDVKERIMSAAAIQGSQFIGKR
ISNAFLKIVIRDVAKRTAAKQTKMFPVVGQAVSASISYYFMNKIGKDHIQKCENVIKNVMRSHHHHHH

Forward Primer* 5'- CCATGGGATTCAAAAACAATTAACATC Seq. ID No. 59
Reverse Primer  5'- GAGATCTCATGACATTTTAATAACATTTTCGC Seq. ID No. 60

*Fig. 2c*

Expressed in pQE-60

Seq. ID No. 61
ATGGGATTCATGGGAGAATACGATCATCAATTAGATACAAAAGGACGTATGATTATACCGTCCAAGTTTCGTTATGACTTAAATGAGCGTTTATTATCACAAGAGGCCTTGATAAATGT
TTATTCGGTTACACTCTAGACGAATGGCAACAGATTGAAGAGAAAATGAAAACCTTACCTATGACAAAAAAGACGCACGTAAGTTTATGCGTATGTTCTTCTGGTGCTGTTGAAGTA
GAACTTGATAAGCAAGGGCGTATTAACATCCCTCAAAACTTGAGGAATCGTATAATAGTACAGTAATCGGTTGTTTCAAATCGTATTGGGATTTGGGATAGAGAAACT
TGGAATGATTTCTATGAAGAATCGAAGAAGTTTCGAAGATATTGCTAAGAACATGGTGTACATTGACTGTACGCCTTTATTTACTAAATCAATTAAATGACGGAAGATTAATAGCA
GAAACCATTGATTATTTAAATGTAAAGAAAATGGTTGCTAAAGAATGGACTTGTACATTGAAGGATAGCATTTGCATAAGGTGACTTTTGTTCATAGCAACTTCCGTGAATTAACTAAATCAAATATTAAAGACTTAAAC
ATCGATCAAGACCAAACTGGAATTATTACGACTTGGGTGTTTCAAGCCCACACGTTAGTGCAAGCGTTAGTGCTATGGCGAAGAAAATTTTCAAACAGATAGCTCGAAGAATCGAAGCACTACGA
CAAGAACTAACAGCATATGAATTGTTAACAATTAGAATTGTTGACATTAGAGAACAAGCGATTGAATTAGTGAAGAAGTATTCCTGCAAAGCAGGATTCCAGTATCCACTTTCCATTCTTTAGAAGATCGTTTATGT
CGCGAACAACAACCAATAACAATTAGAATTGTCAGCTTTTGAAGATTCAATAGAACAAGCGATTGAATTAGTGAAGAAGTATTCCTGCAAAGCAGGATTCCAGTATCCACTTTCCATTCTTTAGAAGATCGTTTATGT
ATTGCAGTAATGATGAATTGTCAGCTTTTGAAGATTCAATAGAACAAGCGATTGAATTAGTGAAGAAGTATTCCTGCAAAGCAGGATTAGTTTCCAAACCGATTACCGCTACAGAA
AAACAGGTGTTCCAAGAATGACAATAACAGAGCACGAAGCGCGAAATTACGTGCTGAAATACTTAAAGATCTCATCACCATCACCACTAA
GAAGATTAGAATGACAATAACAGAGCACGAAGCGCGAAATTACGTGCTGAAATACTTAAAAGATCTCATCACCATCACCACTAA

M.W. = 54.6 kd
Seq. ID No. 62
MGFMGEYDHQLDTKGRMIIPSKFRYDLNERFIITRGLDKCLFGYTLDEWQQIEEKMKTLPMTKKDARKFMRMFFSGAVEVELDKQGRINIPQNLRKYANLTKECTVIGVSNRIEIWDRET
WNDFYEESEESFEDIAEDLIDFXFXNGGIEVFHHISVMLNETIDYLNVKENGVYIDCTLGGAGHALYLLNQLNDDGRLIAIDQDQTAIDNAKEVLKDHLHKVTFVHSNFRELTQILKDLN
IEKVDGIYYDLGVSSPQLDIPERGFSYHHDATLDMRMDQTELTAYEIVNNWSYEALVKIFYRYGEEKFSKQIARRIEAHREQQPITTLELVDIIKEGIPAKARRKGGHPAKRVFQALR
IAVNDELSAFEDSIEQAIELVKVDGRISVITFHSLEDRLCKQVFQEYEKGPEVPRGLPVIPEAYTPKLKRVNRKPITATEEDLDDNNRARSAKLRVAEILKRSHHHHHH

Forward Primer* 5'- CCATGGGATTCATGGGAGAATACGATCATC Seq. ID No. 63
Reverse Primer  5'- GAGATCTTTTAAGTATTTCAGCTACACGTAATTTCGCG Seq. ID No. 64

*Fig. 2d*

Expressed in pQE-60

Seq. ID No. 65
ATGGGAATAAATAATCATGAATTACTAGGTATTCACCATGTTACTGCAATGACAGATGATGCAGAACGTAATTATAAATTTTTTACAGAAGTACTAGGCATGCGTTTAGTTAAAAAGACA
GTCAATCAAGATGATATTTATACGTATCATACTTTTTTGCAGATGAGTTCGGCAGGTACAGACATGACGTTCTTTGATTTTCCAAATATTACAAAAGGCAGGCAGGAACAAAT
TCCATTACAAGACCGTCTTTAGAGTGCCTAACATGACGATTAACATATTGAGTGTTGGTGTTAAACACGAAGGTATTGCAGAATTATTTGGTAAAAAGTG
TTGCCATTTGAAGAAGTCGATGGCCAAGTGTATCAATTTCAGATGAGTTAAATGAAGGGTAGCACCTGGTGTGTATGACAACTATTGCGCATGAAGATAATGTCGCATTACTTGAAGTTGGC
GGATTAGGCCCCATTGTGGAAAATTAAAGTAAGTAATTCTAATAAAGATGATAAAGGGCCAGCAGCACGTCGTCATTTCGTGTGAAAGATCATGATGCAATAGAA
GAAGGAGGCAATGGTGGCCAGGTAATCTAATCAGGACTGGTATTTAATAACTCAGGCATCGTTAATCGTTCTATTTTGAAGCATTATATGCAGTGTGGGGCATATTTAATGAAATTTCAACAGATGGA
GCGTGGGCAACGAAATATAAAGAGGTAGGTATTAATAACATTTATGAAACATTAGGCGAAGGGTTATCCTTACCACCATTTTAGAAAATAAAGAGAATATATTGAATCGGAAGTAGACCTTTTAATACGAAGCGT
CAACATGGTAGATCTCATCACCATCACCACTAA

M.W. = 37.4 kd
Seq. ID No. 66
MGINNHELLGIHHVTAMTDDAERNYKFFTEVLGMRLVKKTVNQDDIYTYHTFFADDVGSAGTDMTFFDFPNITKGQAGTNSITRPSFRVPNDDALTYYEQRFDEFGVKHEGIQELFGKKV
LPFEEVDGQVYQLISDELNEGVAPGVPWKNGPVPVDKAIYGLGPIEIKVSYFDDFKNILETVYGMTTIAHEDNVALLEVGEGNGGQVILIKDDKGPAARQYGEVHHVSFRVKDHDAIE
AWATKYKEVGINNSGIVNRFYFEALYARVGHILIEISTDGPGFMEDEPYETLGEGLSLPPFLENKREYIESEVRPFNTKRQHGRSHHHHHH

Forward Primer*  5'- CCATGGGAATAAATAATCATGAATTACTAGG Seq. ID No. 67
Reverse Primer   5'- GAGATCTACCATGTTGACGCTTCGTATTAAAAGGTC Seq. ID No. 68

*Fig. 2e*

Expressed in pQE-60

Seq. ID No. 69
ATGGGAATAAATAATCATGAATTACTAGGTATTCACCATGTTACTGCAATGACAGATGATGCAGAACGTAATTATAAATTTTTCACAGAAGTACTAGGCATGCGTTTAGTTAAAAGACA
GTCAATCAAGATGATATTTATACCTATCATACTTTTTTCGATGATGTAGGTTCGGCAGATGTAGTTGCAGAGACAGATGAGTTGGGTTCAAATATTACAAAGGGCAGGAACAAAT
TCCATTACAAGACCGTCTTTTAGAGTGCCTAACGATGACGCATTAACATATTATGAACACGCGCTTTGATGAGTTTGGTGTTAAACACGAAGGTATTCAAGAATTATTGGTAAAAAGTG
TTGCCATTTGAAGAAGTCGATGGCCAAGTCGTATCAATTTCAGATGAGTTAAATGAAGGGTAGCACCTGGAAGAATGCGATATTGCGCATGAAGATAATGTCGCATTACTTGAAGTTGGC
GGATTAGGCGCCCCATTGAAATTAAGTAAGGTATTTGACGACTTTAAAAATATTTAGAGACTGTTTACGGTATGACAACTATTCGTGTGAAGATCATGATGCAATAGAA
GAAGGAGGCAACGAATGTGGCCAGGTAATCTTAATAAGAATGATAAAGGGCCAGCACGTCAAGGTATGGTGAGGTACATCATGTTCATTTCGTGTGAAAGATCATGATGCAATAGAA
GCGTGGGCAATTATGGAAGATGAACCTTATGAAACATTAGGCGAAGGGTTATCCTTACCACCATTTTTAGAAATAAAAGAGAATATATTGAATCGGAAGTTAGACCTTTTAATACGAAGCGT
CCAGATTTATGGAAGATGAACCTTATGAAACATTAGGCGAAGGGTTATCCTTACCACCATTTTTAGAAATAAAAGAGAATATATTGAATCGGAAGTTAGACCTTTTAATACGAAGCGT
CAACATGGTAGATCTCATCACCATCACCATCACTAA

M.W. = 37.3 kd

Seq. ID No. 70
MGINNHELLGIHHVTAMTDDAERNYKFFTEVLGMRLVKKTVNQDDIYTYHTFFADDVGSAGTDMTFFDFPNITKGQAGTNSITRPSFRVPNDDALTYEQRFDEFGVKHEGIQELFGKKV
LPFEEVDGQVYQLISDELNEGVAPGVPWKNGPVPVDKAIYGLGPIEIKVSYFDDFKNILETVYGMTTIAHEDNVALLEVGEGNGGQVILIKDDKGPAARQGYGEVHHVSFRVKDHDAIE
AWATKYKEVGINNSGIVNRFYFEALYARVGHLLIEISTDGPGFMEDEPYETLGEGLSLPPFLENKREYIESEVRPFNTKRQHGRSHHHHHH

Forward Primer* 5'- CCATGGGAATAAATAATCATGAATTACTAGG Seq. ID No. 71
Reverse Primer 5'- GAGATCTACCATGTTGACGCTTCGTATTAAAAGG Seq. ID No. 72

*Fig. 2f*

Expressed in pQE-60

Seq. ID No. 73
ATGGGACGTATCTTAAAAGAGTCCATTATTGTGGCATTTGCCTTTGTTGGTGTTGTCGTTGGTGCCGGCTTTGCTACTGGTCAAGAAATTTTCCAGTTTTTCACAAGTCATGGCGCATAT
AGCATTTCAGGCTATTGTAACAGGACTATTGATTACTTTAGGTGGAATGGTTGTCATGCATACAGGTCATCATCTAAAGTCCAGAAATCATTCTGATTCAATTAACTATTTCTTATAC
CCCTCTATTGCAAGAGGTTTTGATATTATTTAACAATGTTCTTTAGCTATATTATGTTTATGCTATCGTTATGCTCGTGCTTGGCGGTGTACCTGGATTGTCATTATGATGCGGTC
AGCGCACTCATATTAGTCGCCTTTATTTTAGCAACACACTCGTTGTTCTAAAAATGATGCTCAGATTCATAAGTCAGAAATCATTATCGTGACTCAAGCGTTATACGGGGCTTGATTGGCGATTAACTATGCAAGCTTGCAA
TACTATTTCACAACAGTCATCAGCTCTTCAAGTGTTACAGTGATTTTACTCGATGATCTGTATCATACCATTTTTTACTCATGATGATTAAT
ATTGCTGCTGCCTTCAGCTTCTTCAATCTGATAAATTCAGTATCGTGACTCAAGTGTCTCCGTCAAATGTTCTCGTCATTATTTACGTTCATCACTTAGATATAGTACATTATC
CTAGGTTAATTTCTGTGTGGATATTAGTCATTGCGTCACGTTTCAGCGTTCAGGATTCTATTCTTACTCGATCAGCAGAGTCTACGTCGTCTCTGTCTCATCATTATTACCGGCAATCTCATATCGAT
GGTTTCATTTGCTATTAATTGGAAAGTATTCCCTATTATGGGATTGTTCGGTTTCGGATTCATCAGCGTATTAAGCGTATTACCGGCAAATCTCATATCGAT
GGATCCAGATCTCATCACCATCACCATCACTAA

M.W. = 40.9 kd
Seq. ID No. 74
MGRILKESIIVAFAFVGVVVGAGFATGQEIFQFFTSHGAYSISGIIVTGLLITLGGMVVMHTGHHLKSRNHSDSINYFLYPSIARGFDIILTMFMLSLAIIMTAGGASTIHQSFNLPYWL
SALIVAFILATLFLKFDRLIAVLGGVTPFLIAIVIMIAVYFTTSHLDFTAANNDAQIHKQKSLSPGWNFDAINYASLQIAAAFSFLSVMGSKVKYRDSTLYGGLIGGLIITFLLMMIN
LGLISQFDKIKHVDLPTLKLATQMSPSIGIIMSVIMILVIYNTVVGLMYAFASRFSVPFSRRYFIIITMAVITYISTFIGFISLIGKVFPIMGLFGFILLIPVLYKGLIKRITGKSHID
GFRSHHHHHH

Forward Primer*  5' - CCATGGGACGTATCTTAAAAGAGTCCATTATTGTGG Seq. ID No. 75
Reverse Primer   5' - GGATCCATCGATATGAGATTTGCCGGTAATACGC Seq. ID No. 76

*Fig. 2g*

Expressed in pQE-60
Seq. ID No. 77
ATGGGATTAATCGATACACATGTCCATTTAAATGATGAGCAATACGATGATTGAGTGAAGTGATTACACGTGCTAGAGAAGCAGGTGTTGATCGTATGTTTGTAGTTGGTTTAAC
AAATCGACACAATTGAACGCGCGATGAAATAATCGATGAGAGTAATCGGTTGGCATTCAGTTGACGCATGATTTTTACAGAAGAACACTTGGAATGGATTGAA
TCTTTAGCTCAGCATCCAATTATCATTCATAATAGCTGAATTTTTATATTTCATTAGGTGACCTGTGACATGCTAAACAGCCTAAAGAAGTTGCTAAGCATGTCAATGGAGCGTTG
CGTTTGAAGTTACCAATATTGTAACTAATAAGCTGATCTTTCGCCACATCCGTATACGTGTTTAATTGTTTAATTTAAATTCAAGATCTCATCACCATCACCATCACTAA
GAAATTGCAGATATATTGTAACTAATAAGCTGATCTTTCGCCACATCCGTATACGTGTTTAATTGTTTAATTTAAATTCAAGATCTCATCACCATCACCATCACTAA
GAAGTGGCGAACAAACAACTAAAATGCAGAGAAATTGTTTAATTTAAATTCAAGATCTCATCACCATCACCATCACTAA M.W. = 30.4 kd
Seq. ID No. 78
MGLIDTHVHLNDEQYDDLSEVITRAREAGVDRMFVVGFNKSTIERAMKLIDEYDFLYGIIGWHPVDAIDFTEEHLEWIESLAQHPKVIGIGEMGLDYHWDKSPADVQKEVFRKQIALAK
RLKLPIIIHNREATQDCIDILLEEHAEEVGGIMHSFSGSPEIADIVTNKLNFYISLGGPVTFKNAKQPKEVAKHVSMERLLVETDAPYLSPHPYRGKRNEPARVTLVAEQIAELKGLSYE
EVCEQTTKNAEKLFNLNSRSHHHHHH Forward Primer* 5'- CCATGGGATTAATCGATACACATGTCCAT Seq. ID No. 79
Reverse Primer  5'- GAGATCTTGAATTTAAATTAAACAATTCTCTGCATTTTAGTTG Seq. ID No. 80

*Fig. 2h*

Expressed in pQE-60

Seq. ID No. 81
ATGGGAATAATATATTGGTGTATGACAGTTAATGGAGGGAACGAAATGAAAGCTTTATTACTTAAAACAAGTGTATGGCTCGTTTGCTTTTAGTGTAATGGGATTATGGCAAGTCTCG
AACGCGGCTGAGCAACATGAAGCAGCAATGAGGAGGAACGAGTAACGATGAAAGCACATGAAACAGATAAGCAACAGCAAATCTGGCAACAGCGCTCATCATTCTGGCAAAGAA
GCGCGACTGACGTAGATACACAAGCCTCAACACAACAAATGATATTCACACAGGTTTCAAGCCTCTAAAACAGCATCACTTTCACCACGAATGTTGCTGCTAAAAGTCACCACAA
CGGCGACTGACGTAGATACACAAGCCTCAACACAACAAATGATATTCACACAGGTTTCAAGCCTCTAAAACAGCATCACTTTCACCACGAATGTTGCTGCTAAAAGCCTGATTTA
ACAACAACAACATAAAATATTACATAAGGGCTGTCTAAAGGTGAAGAAATGGCTAAGTGGAAAAATGGCTTATGATGCTAAGCCTTCAACGATTGTAACACAAA
ATGTTAGACGCAGGAGACGCCTTCAAGTTGAAAAGTTAGAGGGTATGTTAGACTTTCGAAAACGAAAACACCAGAAACGAAAAGTCCTTCGAAGCATTAAGACACTAAAACACAGGCGAATCCACAA
TTTGACTTGGATACGATCAGTTGAATTATTGTGTAACGACACATTGTTGTTATATCACATTAGGAATTGATCCTTCAAATTTATCACAACGTCATTAGATTACTTAGTGAAAAACAATGAAGAAAACCACAA
AATGGTATCGTATGAATTATTGTGTAACGACACATTGTTGTTATATCACATTAGGAATTGATCCTTCAAATTTATCACAACGTCATTAGATTACTTAGTGAAAAACAATGAAGAAAATCCACAA
ATGCGTATTTATAAAACGTAGAACGTATTACACATTGGTCATTCATTCAAATTGTCAAATTTATAAACATGATCGTCAAATTTGTAAAGACGTTAACAATGATCTGAACATGCATTCGAATATGATCAA
ACATTAATTATCGCAAACTCAGAGAATTTCTCTAAAAGAACTGACTTTGCCTAGGAATTGATGTGAAAGGCTCTTCAGACGTCTGGACGCTCTGAGACGTTTACTAGATAAATAAACGAATAATCGCGATTGCAGATGCTATG
GAAGCGTATGGAAATACGATTCGCAAATGCTCTGATTCAATCCGTGTTTACTAGCTAAGTTGACGACGATATCAGGTGGGACGGATATAGTATGTCTGGCAAACGATATATGTTCGGTGTGCCAAATAGAAAACCAGCTAAAGAACGATACTAGCAAGTT
CCATTTGGAAATACGATTCGCAAATGCTCTGATTCAATCCGTGTTTACTAGCTAAGTTGACGACGATATCAGGTGGGACGGATATAGTATGTCTGGCAAACGATATATGTTCAAATTTAAATAAGGACCAGCTAAAGAACAACCAGCTAAAGAACGATACTAGCAAGTT
GGCGGTTTACTACAATCTCTGATTCAATCCGTGTTTACTAGCTAAGTTGACGACGATATCAGGTGGGACGGATATAGTATGTCTGGCAAACGATATATGTTAGGTAAAAAAACCAGCTAAAGAACAACCAGCTAAAGAACGATACTAGCAAGTT
ATTTAAAACGTGATTCACGTAACGATGAACTGTCTAACTTGGTGACGACAAGTGATGACGACAAAGTGTATGTTGATATTGTTGAGATCTCATCATCCACCATCACTAA
CTGGTAAAGATACACAACCAATTGGTGACGACAAAGTGATGACGACAAAGTGTATGTTGATATTGTTGAGATCTCATCATCCACCATCACTAA

M.W. = 78.1 kd
Seq. ID No. 82
MGIIYWCMTVNGGNEMKALLLKTSVMLVLLFSVMGLWQVSNAAEQHTPMKAHAVTTIDKATTDKQQVPPTKEAAHHSGKEAATNVSASAQGTADDTNSKVTSNAPSNKPSTVVSTKVNET
RDVDTQQASTQKPTHTATFKLSNAKTASLSPRMFAANAPQTTHKILHTNDIHGRLAEEKGRVIGMAKLKTVKEQEKPDLMLDAGDAFQGLPLSNQSKGEEMAKAMNAVGYDAMAVGNHE
FDFGYDQLKKLEGMLDFPMLSTNVYKDGKRAFKPSTIVTKNGIRYGIIGVTTPETKTKTRPEGIKGVEFRDPLQSVTAEMRIYKDVDTFVVISHLGIDPSTQETWRGDYLVKQLSQNPQ
LKKRITVIDGHSHTVLQNGQIYNNDALAQTGTALANIGKITFNYRNGEVSNIKPSLINVKDVENVTPNKALAEQINQADQTFRAQTAEVIIPNNTIDFKGERDDVRTRETNLGNAIADAM
EAYGVKNFSKKTDFAVTNGGGIRASIAKGKVTRYDLISVLPFGNTIAQIDVKGSDWTAFEHSLGAPTTQKDGKTVLTANGLLHISDSIRVYYDINKPSGKRINAIQILNKETGKFENI
DLKRVYHVTMNDFTASGGDGYSMFGGPREEGISLDQVLASYLKTANLAKYDTTEPQRMLLGKPAVSEQPAKGQQGSKGSKSGKDTQPIGDDKVMDPAKKPAPGKVVLLRSHHHHHH

Forward Primer* 5'- CCATGGGAATAATATATATTGGTGTATGACACAG Seq. ID No. 83
Reverse Primer 5'- GAGATCTCAACAATACAACTTTACCTGGAGCTGG Seq. ID No. 84

Fig. 2i

Expressed in pQE-60

Seq. ID No. 85
ATGGATAATAATGAAAAAAGAAAAAGTAAAGTGAACTATTAGTTGTAACAGGTTTATCTGGCGCAGTAAATCTTTGGTTATTCAATGTTTAGAAGACATGGATATTTTGTGTAGAT
AATCTACCACCAGTGTTATTGCCTAAATTGTGAGAGTTGATGAAGACAAGGAAATCCATCCTAAGAAAAGTGGCAATTGATTGATTTAAGAGGTAAGAACTATTAATTCATTAGTT
GCAGTAGTGGATAAAGTCAAAGTGAAAGTGACGTCATCATTGATGTTTATGTTTCAAGATATAAGGAAAACGCGTCGTGCACATCCTTTGATG
GAACAAGGTAAAAGATCGTTAATCAATGATGAGAGTTTGAAACCTTTAACAGATTAGATAGCTAATTTGTTATAGATACTACAAAGTTATCACCTAAAGAATTAAAA
GAACGCATTCGTCGATACTATTATGTAGTAGATTAAGACCTTTAACAGATTAGATAAAGACGTTATATAATTATGTTATGAAAATGGAAGATTTTCTTTGAAAAATTAACTGATTTG
TTACCAAATCCATATTATGTAGTAGATTAAGACCTTTAACAGATTAGATAAAGACGTTATATAATTATGTTATGAAAATGGAAGATTTTCTTTGAAAAATTAACTGATTTG
TTAGATTTATGATACCCGGGTATAAAAAGAAGGGAAATCTCAATTAGTAATTGCCATCGGTGTACGGTGACAACATCTGATCTGTAGCATTAGCAGAACGACTAGGTAATTATCTA
AATGAAGTATTTGAATATATGTTATGTGCATCATAGGGACGCACATATTGAAAGTGGCGAGAAAAAGATCTCATCACCATCACCATCACTAA

M.W. = 35.9 kd
Seq. ID No. 86
MDNNEKEKSKSELLVVTGLSGAGKSLVIQCLEDMGYFCVDNLPPVLLPKFVELMEQGNPSLRKVAIAIDLRGKELFNSLVAVVDKVKSESDVIIDVMFLEASTEKLISRYKETRRAHPLM
EQGKRSLINAINDEREHLSQIRSIANFVIDTKLSPKELKERIRRYYEDEEFETFTINVTSFGFKHGIQMDADLVFDVRFLPNPYYVVDLRPLTGLDKDVYNYVMKWKETEIFFEKLTDL
LDFMIPGYKKEGKSQLVIAIGCTGGQHRSVALAERLGNYLNEVFEYNVYHHRDAHIESGEKKRSHHHHHH

Forward Primer* 5'- CCATGGATAATAATGAAAAAGAAAAAGTGAAC Seq. ID No. 87
Reverse Primer  5'- GAGATCTTTTTTCTCGGCCACTTTCAATATGTGCGTCCC Seq. ID No. 88

*Fig. 2j*

Expressed in pQE-60

Seq. ID No. 89
ATGGGACGATTTACATTTCAAACGATTTAGGAACGATTATTACTATTATATTTGGATTCATCATTAATTAGTATTGGCTTTTATTATTATCTTTTAGAAGAAATAGGCGT
ACAGCGAGTTCAACTTGGGCATGGGTTTGTCTTACCATTGATTGGTTTTATTCTTTGTTTTTTGGTAGAACCGTTTCGGCACGCAAATTGAATAAAACAATGGT
AACGTGTTAACGATTCGATGGACTTTTAAAACAACAAGTTTAAATTATGGTAACAAGCTTCATTGATATGAAGATATTAAAGATATTAAAGAATATATCCATTAGAG
ATGGATCAAGATGGTTTTAGATGGTTTGATGATCATTCATTGAAGATGGAAGATTTATATGACTCAAGTTTAAAGAATTATATGAAACAAGGCTAGAATGTTGAGATCATCGTAAG
TACTATACTTTCGTTGAGATGCTTTAAATCGTTAGGTGGAGAAGTTAGCCATTTTTGCTCAAAATTTACCGTTATTGAATATCTTAGGAATAATGATGAATATTGGAGAGATACGCATTTGAATACGTATACAAGGGATGCGGTTGATGCACTG
GATGTGCAACTAGGTATGTCGAGGATTTAACATTGGTGATGAATATCGGTGATGAATATCTAGGATTTGAAGCATTTGAAATTGGAAAATTGAAATGATGGACCACGAAAAACGAACGACCATTGGCAATTCATTCCGGATAATCATTATAAAT
CAGTTGCGATTTATTTTAGACTGGCATCAAATTGAATACGTACATTTGAAGATGGTAGCCCGGCTAGTGACTGGCTCAAATCAGGTGTAGATGATACAGTTATGGGCAAATCATCCATAGTAATGGCCGGATCAAATTTCAATGCCTCTGACTTATTATCAAGTGGT
GTAAATTTATACGATGAAAATGGATTATATCATTGCTAAAGATTGTGGCTTAATGCAATTCTAAAATCGTGCTAATCGAGAAATCGTATCAGTGGGCACAGCAAATATGGACTTTAGAAGTTTGAATTAAATTTGAA
AATTCAAAGAATCGTTAGCAGAATGCAAAATTAGTTTCGCCAATTTAAGATCTCATCACCATCACCACTAA

M.W. = 57.4 kd
Seq. ID No. 90
MGRFTFSNDLGTLFTIIAIGFIINLVLAFIIFLERNRRTASSTWAWLFVLFVLPLIGFILYLFFGRTVSARKLNKNNGNVLTDFDGLLKQQIESFDKGNYGTDNKQVQKHHDLVRMLL
MDQDGFLTENNKVDHFIDGNDLYDQVLKDIKNAKEYIHLEYYTFALDGLGKRIHALEEKLKQGLEVKILYDDVGSKNVKMANFDHFKSLGGEVEAFFASKLPLLNFRMNRNHRKIIVI
DQGLGYVGGFNIGDEVYLGLGKLGYMRDTHLRIQGDAVDALQLRFILDWNSQAHRPQFEYDVKYFPKKNGPLGNSPIQIAASGPASDWHQIEYGYTKMIMSAKKSVYLQSPYFIPDNSYIN
AIKIAAKSGVDVHLMIPCKPDHPLVYWATFSNASDLLSSGVKIYTYENGFIHSKMCLIDDEIVSVGTANMDFRSFELNFEVNAFVYDENLAKDLRVAYEHDITKSKQLTKESYANRPLSV
KFKESLAKLVSPIILRSHHHHHH

Forward Primer* 5'- CCATGGGACGATTTACATTTCAAACGATTAGG Seq. ID No. 91
Reverse Primer 5'- GAGATCTTAAAATTGGCGAAACTAATTTGCTAACG Seq. ID No. 92

*Fig. 2k*

Expressed in pQE-60
Seq. ID No. 93
ATGGGAAAGATTTTATTCGTTTGTACAGGTAACACATGTCGTAGCCCATTAGCGGAAAGTATTGCAAAGAGGTTATGCCAAATCATCAATTTGAATCAAGAGGTATATTCGCTGTGAAC
AATCAAGGTGTTTCACAGAATTAGTTGAAGAACATCATTAGCTGAAGACCTTATCGCAACAATTTACTGAAACAGATTTGAAAGCAGATATTATTTTGACGATGTCG
TATTCGCACAAAGAATTAATAGAGAACTTGTAAGAGGCACACTTTGGTTTGCAAATCATGTTTTCACATTGCATGAATATGTAAAAGAAGCAGGAGAAGTTATAGATCCATACGGTGGAACAAAGAAATG
TATGTACATAACCTATGAAGAATGTTGTAAGTTTAATTTAAAAGATATTATTTGCAGATCTCATCACCATCACCATCACTAA M.W. = 16.9 kd
Seq. ID No. 94
MGKILFVCTGNTCRSPLAESIAKEVMPNHQFESRGIFAVNNQGVSNYVEDLVEEHHILAETTLSQQPTEADLKADIILTMSYSHKELIEAHFGLQNHVFTLH
EYVKEAGEVIDPYGGTKEMYVHTYEELVSLIIKLKDIICRSHHHHHH Forward Primer* 5'- CCATGGGAAAGATTTTATTCGTTTGTACAGGTAAC Seq. ID No. 95
Reverse Primer 5'- GAGATCTGCAAATAATATCTTTTAATTTAAAATTAAAGAATG Seq. ID No. 96

*Fig. 2l*

SEQUENCE LISTING

<160> NUMBER OF SEQ ID NOS: 99

<210> SEQ ID NO 1
<211> LENGTH: 819
<212> TYPE: DNA
<213> ORGANISM: Staphylococcus aureus

<400> SEQUENCE: 1

```
atgtatttac ttacctccaa ttataattgt accggttcaa tttgtaaacg ccgatacaat      60
tataatattt tgtgctataa taattacaga caaagtgaaa acgaggacag atatattgtta    120
aagtatgaac atattgctaa gcaacttaat gcgtttatac atcaatctaa tttcaaaccc    180
ggtgataaat tgccaagcgt gacgcaatta aaagaacgtt atcaagtaag taagagtact    240
atcattaaag cattaggctt attggaacaa gatggtttga tctatcaagc acaaggcagt    300
ggtatttatg tgagaaatat tgctgatgcc aatcgtatca acgtctttaa gactaatggt    360
ttctctaaaa gtttaggtga acaccgaatg acaagtaagg tacttgtttt taaggagatt    420
gcaacgccac ctaaatctgt acaagatgag ctccaattaa atgcagatga taccgtctac    480
tatttagagc gattaagatt cgtggacgat gatgttttat gtatcgaata ttcttattat    540
cataaagaaa tcgtgaaata tttaaatgat gatattgcta agggctctat cttcgactat    600
ttagaatcaa acatgaaact tcgtattggt ttttcagata ttttctttaa tgtagatcaa    660
ctcacttcaa gtgaagcttc attactacaa ttgtctacag gtgaaccatg tttacgttac    720
caccagactt tttatacaat gactggcaaa ccctttgatt catctgacat cgtatttcat    780
tatcgtcatg cacagtttta tattcctagt aaaaagtaa                           819
```

<210> SEQ ID NO 2
<211> LENGTH: 272
<212> TYPE: PRT
<213> ORGANISM: Staphylococcus aureus

<400> SEQUENCE: 2

Met Tyr Leu Leu Thr Ser Asn Tyr Asn Cys Thr Gly Ser Ile Cys Lys
1               5                   10                  15

Arg Arg Tyr Asn Tyr Asn Ile Leu Cys Tyr Asn Asn Tyr Arg Gln Ser
            20                  25                  30

Glu Asn Glu Asp Arg Ile Leu Leu Lys Tyr Glu His Ile Ala Lys Gln
        35                  40                  45

Leu Asn Ala Phe Ile His Gln Ser Asn Phe Lys Pro Gly Asp Lys Leu
    50                  55                  60

Pro Ser Val Thr Gln Leu Lys Glu Arg Tyr Gln Val Ser Lys Ser Thr
65                  70                  75                  80

Ile Ile Lys Ala Leu Gly Leu Leu Glu Gln Asp Gly Leu Ile Tyr Gln
                85                  90                  95

Ala Gln Gly Ser Gly Ile Tyr Val Arg Asn Ile Ala Asp Ala Asn Arg
            100                 105                 110

Ile Asn Val Phe Lys Thr Asn Gly Phe Ser Lys Ser Leu Gly Glu His
        115                 120                 125

Arg Met Thr Ser Lys Val Leu Val Phe Lys Glu Ile Ala Thr Pro Pro
    130                 135                 140

Lys Ser Val Gln Asp Glu Leu Gln Leu Asn Ala Asp Asp Thr Val Tyr
145                 150                 155                 160

Tyr Leu Glu Arg Leu Arg Phe Val Asp Asp Asp Val Leu Cys Ile Glu 165                 170                 175
Tyr Ser Tyr Tyr His Lys Glu Ile Val Lys Tyr Leu Asn Asp Asp Ile
                180                 185                 190

Ala Lys Gly Ser Ile Phe Asp Tyr Leu Glu Ser Asn Met Lys Leu Arg
            195                 200                 205

Ile Gly Phe Ser Asp Ile Phe Phe Asn Val Asp Gln Leu Thr Ser Ser
        210                 215                 220

Glu Ala Ser Leu Leu Gln Leu Ser Thr Gly Glu Pro Cys Leu Arg Tyr
225                 230                 235                 240

His Gln Thr Phe Tyr Thr Met Thr Gly Lys Pro Phe Asp Ser Ser Asp
                245                 250                 255

Ile Val Phe His Tyr Arg His Ala Gln Phe Tyr Ile Pro Ser Lys Lys
                260                 265                 270

<210> SEQ ID NO 3
<211> LENGTH: 828
<212> TYPE: DNA
<213> ORGANISM: Staphylococcus aureus

<400> SEQUENCE: 3
atggcacttt atggatttgc ccaaggactt attcaagaag caggaattag aattaaacaa      60
ttgatggagc aaaatttaac aattgaaaca aagtcaaatc cgaatgacct tgttacaaat     120
gtagataaag caacagaaga tttcattttt gatacaattt tagaaacata tcccaatcat     180
caagtattag gtgaagaagg gcatggtcat gacatcgata cttccaaagg tacggtatgg     240
attgttgacc aatagacgg tacattgaat tttgttcatc aacaagaaaa tttcgcaatt     300
tcaattggta tttatatcga tggtaaacct tatgcaggtt ttgtatatga tgttatggct     360
gatgtcttat atcatgctaa agtaggggaa ggtgcatatc gtggtagcca acccttgaaa     420
ccattgaatg attctaatct aagacaaagc attattggga tcaatccgaa ctggttaact     480
aaaccaattt taggagaaat ctttaaagaa attgttaatg attctagaag tgcaagggca     540
tatggtagtg cagcgcttga atcgtttca gttgctacag gtaatttaga agcatatatg     600
acgccaagac ttcaaccatg ggattttgct ggcggattgg ttatttata tgaagtaaat     660 ggacaagctt ccaatttact aggaggacca ttaacaatta gtggtccaaa ttcaatctta     720
gttggaaatc gtggtctcca tcaagaaatt agcaatgatt atttagagcc ccaccatgat     780
gcgttaatac aattacatga caacgatttt aaagaaaat caaaataa                   828

<210> SEQ ID NO 4
<211> LENGTH: 275
<212> TYPE: PRT
<213> ORGANISM: Staphylococcus aureus

<400> SEQUENCE: 4

Met Ala Leu Tyr Gly Phe Ala Gln Gly Leu Ile Gln Glu Ala Gly Ile
1               5                   10                  15

Arg Ile Lys Gln Leu Met Glu Gln Asn Leu Thr Ile Glu Thr Lys Ser
            20                  25                  30

Asn Pro Asn Asp Leu Val Thr Asn Val Asp Lys Ala Thr Glu Asp Phe
        35                  40                  45

Ile Phe Asp Thr Ile Leu Glu Thr Tyr Pro Asn His Gln Val Leu Gly
    50                  55                  60

Glu Glu Gly His Gly His Asp Ile Asp Thr Ser Lys Gly Thr Val Trp
65                  70                  75                  80

```
Ile Val Asp Pro Ile Asp Gly Thr Leu Asn Phe Val His Gln Gln Glu
                85                  90                  95

Asn Phe Ala Ile Ser Ile Gly Ile Tyr Ile Asp Gly Lys Pro Tyr Ala
            100                 105                 110

Gly Phe Val Tyr Asp Val Met Ala Asp Val Leu Tyr His Ala Lys Val
        115                 120                 125

Gly Glu Gly Ala Tyr Arg Gly Ser Gln Pro Leu Lys Pro Leu Asn Asp
    130                 135                 140

Ser Asn Leu Arg Gln Ser Ile Ile Gly Ile Asn Pro Asn Trp Leu Thr
145                 150                 155                 160

Lys Pro Ile Leu Gly Glu Ile Phe Lys Glu Ile Val Asn Asp Ser Arg
                165                 170                 175

Ser Ala Arg Ala Tyr Gly Ser Ala Ala Leu Glu Ile Val Ser Val Ala
            180                 185                 190

Thr Gly Asn Leu Glu Ala Tyr Met Thr Pro Arg Leu Gln Pro Trp Asp
        195                 200                 205

Phe Ala Gly Gly Leu Val Ile Leu Tyr Glu Val Asn Gly Gln Ala Ser
    210                 215                 220

Asn Leu Leu Gly Gly Pro Leu Thr Ile Ser Gly Pro Asn Ser Ile Leu
225                 230                 235                 240

Val Gly Asn Arg Gly Leu His Gln Glu Ile Ser Asn Asp Tyr Leu Glu
                245                 250                 255

Pro His His Asp Ala Leu Ile Gln Leu His Glu Gln Arg Phe Lys Arg
            260                 265                 270

Lys Ser Lys
        275
```

<210> SEQ ID NO 5
<211> LENGTH: 543
<212> TYPE: DNA
<213> ORGANISM: Staphylococcus aureus

<400> SEQUENCE: 5

```
atgggattca aaacaatttt aacatcaaat ttaacaaata aaatcggtaa ttcagtcttt      60
aaaatagaaa atgttgacgg aaaaggtgca atgccaacga cgattcaaga attgagagaa     120
agacgacaac gtgctgaagc aattgtaaag agaaagtctt taatgtcatc aacaatgagc     180
gttgttccaa ttccgggttt agattttggt gttgatttaa aattaatgaa agatattatc     240
gaagatgtta ataaaattta tggtttagat cataagcaag ttaatagcct tggggatgat     300
gtgaaagaaa gaattatgtc tgcagcagca attcaaggta gtcaatttat tggtaaaaga     360
atttcaaatg cattttttaaa aattgtaatt agagatgtag ctaaacgtac tgctgcaaaa     420
caaacaaaat ggtttcctgt tgtaggacaa gctgtgtctg catctattag ttactatttt     480
atgaataaaa ttggaaaaga tcacattcaa aaatgcgaaa atgttattaa aaatgtcatg     540
tag                                                                   543
```

<210> SEQ ID NO 6
<211> LENGTH: 180
<212> TYPE: PRT
<213> ORGANISM: Staphylococcus aureus

<400> SEQUENCE: 6

```
Met Gly Phe Lys Asn Asn Leu Thr Ser Asn Leu Thr Asn Lys Ile Gly
1               5                   10                  15

Asn Ser Val Phe Lys Ile Glu Asn Val Asp Gly Lys Gly Ala Met Pro
```

|     | 20 |     |     |     | 25 |     |     |     | 30 |     |     |
| --- | --- | --- | --- | --- | --- | --- | --- | --- | --- | --- | --- |

Thr Thr Ile Gln Glu Leu Arg Glu Arg Gln Arg Ala Glu Ala Ile
          35              40              45

Val Lys Arg Lys Ser Leu Met Ser Ser Thr Met Ser Val Val Pro Ile
50              55              60

Pro Gly Leu Asp Phe Gly Val Asp Leu Lys Leu Met Lys Asp Ile Ile
65              70              75              80

Glu Asp Val Asn Lys Ile Tyr Gly Leu Asp His Lys Gln Val Asn Ser
              85              90              95

Leu Gly Asp Asp Val Lys Glu Arg Ile Met Ser Ala Ala Ala Ile Gln
          100             105            110

Gly Ser Gln Phe Ile Gly Lys Arg Ile Ser Asn Ala Phe Leu Lys Ile
          115             120            125

Val Ile Arg Asp Val Ala Lys Arg Thr Ala Ala Lys Gln Thr Lys Trp
          130             135            140

Phe Pro Val Val Gly Gln Ala Val Ser Ala Ser Ile Ser Tyr Tyr Phe
145              150              155              160

Met Asn Lys Ile Gly Lys Asp His Ile Gln Lys Cys Glu Asn Val Ile
          165             170            175

Lys Asn Val Met
          180

<210> SEQ ID NO 7
<211> LENGTH: 1383
<212> TYPE: DNA
<213> ORGANISM: Staphylococcus aureus

<400> SEQUENCE: 7

```
atgttcatgg gagaatacga tcatcaatta gatacaaaag gacgtatgat tataccgtcc      60
aagtttcgtt atgacttaaa tgagcgtttt attatcacaa gaggccttga taaatgttta     120
ttcggttaca ctctagacga atggcaacag attgaagaga aaatgaaaac cttacctatg     180
acaaaaaaag acgcacgtaa gtttatgcgt atgttcttct ctggtgctgt tgaagtagaa     240
cttgataagc aagggcgtat taacatccct caaaacttga ggaaatacgc taatttaact     300
aaagaatgta cagtaatcgg tgtttcaaat cgtattgaga tttgggatag agaaacttgg     360
aatgatttct atgaagaatc tgaagaaagt ttcgaagata ttgctgaaga tttaatagat     420
tttsatttty aaaatggagg aattgaagtg tttcatcata tcagcgttat gttaaacgaa     480
accattgatt atttaaatgt aaaagaaaat ggtgtgtaca ttgactgtac gctaggtgga     540
gcgggacatg ccctttattt actaaatcaa ttaaatgacg acggaagatt aatagcaatc     600
gatcaagacc aaactgcaat tgataatgct aaagaggtat aaaggatca tttgcataag     660
gtgactttg ttcatagcaa cttccgtgaa ttaactcaaa tattaaaaga cttaaacatt     720
gaaaagtag atggaattta ttacgacttg gtgtttcaa gcccacaact cgacattcca     780
gaacgaggat tcagttatca ccatgacgca acattagaca tgcgtatgga ccaaacacaa     840
gaactaacag catatgaaat tgttaacaat tggtcatatg aagcgttagt gaagattttt     900
tatcgctatg gcgaggagaa attttcaaaa cagatagctc gaagaatcga agcacatcgc     960
gaacaacaac caataacaac aacattgaa ttagttgaca ttataaaaga ggtattcct    1020
gcaaaagcaa gaagaaaagg cggacatcct gcaaaacgag tatttcaagc actacgaatt    1080
gcagtaaacg atgaattgtc agcttttgaa gattcaatag aacaagcgat tgaattagtg    1140
aaagtagatg gcaggatttc ggtaatcact ttccattctt tagaagatcg tttatgtaaa    1200
```

```
caggtgttcc aagaatatga aaaggtcca gaggtaccaa gaggattacc agttatacca    1260
gaagcatata cacctaagtt aaagcgtgtt aatcgtaaac cgattaccgc tacagaagaa    1320
gatttagatg acaataacag agcacgaagc gcgaaattac gtgtagctga aatacttaaa    1380
taa                                                                   1383
```

<210> SEQ ID NO 8
<211> LENGTH: 460
<212> TYPE: PRT
<213> ORGANISM: Staphylococcus aureus
<220> FEATURE:
<221> NAME/KEY: misc_feature
<222> LOCATION: (142)..(142)
<223> OTHER INFORMATION: Corresponding codon encodes either asparagine
      or histidine.

<400> SEQUENCE: 8

```
Met Phe Met Gly Glu Tyr Asp His Gln Leu Asp Thr Lys Gly Arg Met
1               5                   10                  15

Ile Ile Pro Ser Lys Phe Arg Tyr Asp Leu Asn Glu Arg Phe Ile Ile
            20                  25                  30

Thr Arg Gly Leu Asp Lys Cys Leu Phe Gly Tyr Thr Leu Asp Glu Trp
        35                  40                  45

Gln Gln Ile Glu Glu Lys Met Lys Thr Leu Pro Met Thr Lys Lys Asp
    50                  55                  60

Ala Arg Lys Phe Met Arg Met Phe Phe Ser Gly Ala Val Glu Val Glu
65                  70                  75                  80

Leu Asp Lys Gln Gly Arg Ile Asn Ile Pro Gln Asn Leu Arg Lys Tyr
                85                  90                  95

Ala Asn Leu Thr Lys Glu Cys Thr Val Ile Gly Val Ser Asn Arg Ile
            100                 105                 110

Glu Ile Trp Asp Arg Glu Thr Trp Asn Asp Phe Tyr Glu Glu Ser Glu
        115                 120                 125

Glu Ser Phe Glu Asp Ile Ala Glu Asp Leu Ile Asp Phe Xaa Phe Gln
    130                 135                 140

Asn Gly Gly Ile Glu Val Phe His His Ile Ser Val Met Leu Asn Glu
145                 150                 155                 160

Thr Ile Asp Tyr Leu Asn Val Lys Glu Asn Gly Val Tyr Ile Asp Cys
                165                 170                 175

Thr Leu Gly Gly Ala Gly His Ala Leu Tyr Leu Leu Asn Gln Leu Asn
            180                 185                 190

Asp Asp Gly Arg Leu Ile Ala Ile Asp Gln Asp Gln Thr Ala Ile Asp
        195                 200                 205

Asn Ala Lys Glu Val Leu Lys Asp His Leu His Lys Val Thr Phe Val
    210                 215                 220

His Ser Asn Phe Arg Glu Leu Thr Gln Ile Leu Lys Asp Leu Asn Ile
225                 230                 235                 240

Glu Lys Val Asp Gly Ile Tyr Tyr Asp Leu Gly Val Ser Ser Pro Gln
                245                 250                 255

Leu Asp Ile Pro Glu Arg Gly Phe Ser Tyr His His Asp Ala Thr Leu
            260                 265                 270

Asp Met Arg Met Asp Gln Thr Gln Glu Leu Thr Ala Tyr Glu Ile Val
        275                 280                 285

Asn Asn Trp Ser Tyr Glu Ala Leu Val Lys Ile Phe Tyr Arg Tyr Gly
    290                 295                 300
```

-continued

```
Glu Glu Lys Phe Ser Lys Gln Ile Ala Arg Arg Ile Glu Ala His Arg
305                 310                 315                 320

Glu Gln Gln Pro Ile Thr Thr Thr Leu Glu Leu Val Asp Ile Ile Lys
            325                 330                 335

Glu Gly Ile Pro Ala Lys Ala Arg Arg Lys Gly Gly His Pro Ala Lys
        340                 345                 350

Arg Val Phe Gln Ala Leu Arg Ile Ala Val Asn Asp Glu Leu Ser Ala
    355                 360                 365

Phe Glu Asp Ser Ile Glu Gln Ala Ile Glu Leu Val Lys Val Asp Gly
370                 375                 380

Arg Ile Ser Val Ile Thr Phe His Ser Leu Glu Asp Arg Leu Cys Lys
385                 390                 395                 400

Gln Val Phe Gln Glu Tyr Glu Lys Gly Pro Glu Val Pro Arg Gly Leu
                405                 410                 415

Pro Val Ile Pro Glu Ala Tyr Thr Pro Lys Leu Lys Arg Val Asn Arg
            420                 425                 430

Lys Pro Ile Thr Ala Thr Glu Glu Asp Leu Asp Asp Asn Asn Arg Ala
        435                 440                 445

Arg Ser Ala Lys Leu Arg Val Ala Glu Ile Leu Lys
    450                 455                 460

<210> SEQ ID NO 9
<211> LENGTH: 969
<212> TYPE: DNA
<213> ORGANISM: Staphylococcus aureus

<400> SEQUENCE: 9 atgataaaata atcatgaatt actaggtatt caccatgtta ctgcaatgac agatgatgca    60
gaacgtaatt ataaattttt tacagaagta ctaggcatgc gtttagttaa aaagacagtc   120
aatcaagatg atatttatac gtatcatact ttttttgcag atgatgtagg ttcggcaggt   180
acagacatga cgttctttga ttttccaaat attacaaaag ggcaggcagg aacaaattcc   240
attacaagac cgtctttag agtgcctaac gatgacgcat taacatatta tgaacagcgc   300
tttgatgagt ttggtgttaa acacgaaggt attcaagaat tatttggtaa aaaagtgttg   360
ccatttgaag aagtcgatgg ccaagtgtat caattaattt cagatgagtt aaatgaaggg   420
gtagcacctg tgtaccttg aagaatggga ccggttccag tagataaagc gatttatgga   480 ttaggccccca ttgaaattaa agtaagttat tttgacgact ttaaaaatat tttagagact   540
gtttacggta tgacaactat tgcgcatgaa gataatgtcg cattacttga agttggcgaa   600
ggaggcaatg gtggccaggt aatcttaata aagatgata aagggccagc agcacgtcaa   660
ggttatggtg aggtacatca tgtgtcattt cgtgtgaaag atcatgatgc aatagaagcg   720
tgggcaacga aatataaaga ggtaggtatt aataactcag gcatcgttaa tcgtttctat   780
tttgaagcat tatatgcacg tgtggggcat atttttaatag aaatttcaac agatggacca   840
ggatttatgg aagatgaacc ttatgaaaca ttaggcgaag ggttatcctt accaccattt   900
ttagaaaata aaagagaata tattgaatcg gaagttagac cttttaatac gaagcgtcaa   960
catggttaa                                                           969

<210> SEQ ID NO 10
<211> LENGTH: 322
<212> TYPE: PRT
<213> ORGANISM: Staphylococcus aureus

<400> SEQUENCE: 10
```

```
Met Ile Asn Asn His Glu Leu Leu Gly Ile His His Val Thr Ala Met
1               5                   10                  15

Thr Asp Asp Ala Glu Arg Asn Tyr Lys Phe Phe Thr Glu Val Leu Gly
            20                  25                  30

Met Arg Leu Val Lys Lys Thr Val Asn Gln Asp Asp Ile Tyr Thr Tyr
        35                  40                  45

His Thr Phe Phe Ala Asp Asp Val Gly Ser Ala Gly Thr Asp Met Thr
    50                  55                  60

Phe Phe Asp Phe Pro Asn Ile Thr Lys Gly Gln Ala Gly Thr Asn Ser
65                  70                  75                  80

Ile Thr Arg Pro Ser Phe Arg Val Pro Asn Asp Asp Ala Leu Thr Tyr
                85                  90                  95

Tyr Glu Gln Arg Phe Asp Glu Phe Gly Val Lys His Glu Gly Ile Gln
            100                 105                 110

Glu Leu Phe Gly Lys Lys Val Leu Pro Phe Glu Glu Val Asp Gly Gln
        115                 120                 125

Val Tyr Gln Leu Ile Ser Asp Glu Leu Asn Glu Gly Val Ala Pro Gly
    130                 135                 140

Val Pro Trp Lys Asn Gly Pro Val Pro Val Asp Lys Ala Ile Tyr Gly
145                 150                 155                 160

Leu Gly Pro Ile Glu Ile Lys Val Ser Tyr Phe Asp Asp Phe Lys Asn
                165                 170                 175

Ile Leu Glu Thr Val Tyr Gly Met Thr Thr Ile Ala His Glu Asp Asn
            180                 185                 190

Val Ala Leu Leu Glu Val Gly Glu Gly Gly Asn Gly Gly Gln Val Ile
        195                 200                 205

Leu Ile Lys Asp Asp Lys Gly Pro Ala Ala Arg Gln Gly Tyr Gly Glu
    210                 215                 220

Val His His Val Ser Phe Arg Val Lys Asp His Asp Ala Ile Glu Ala
225                 230                 235                 240

Trp Ala Thr Lys Tyr Lys Glu Val Gly Ile Asn Asn Ser Gly Ile Val
                245                 250                 255

Asn Arg Phe Tyr Phe Glu Ala Leu Tyr Ala Arg Val Gly His Ile Leu
            260                 265                 270

Ile Glu Ile Ser Thr Asp Gly Pro Gly Phe Met Glu Asp Glu Pro Tyr
        275                 280                 285

Glu Thr Leu Gly Glu Gly Leu Ser Leu Pro Pro Phe Leu Glu Asn Lys
    290                 295                 300

Arg Glu Tyr Ile Glu Ser Glu Val Arg Pro Phe Asn Thr Lys Arg Gln
305                 310                 315                 320

His Gly

<210> SEQ ID NO 11
<211> LENGTH: 969
<212> TYPE: DNA
<213> ORGANISM: Staphylococcus aureus

<400> SEQUENCE: 11 atgataaaata atcatgaatt actaggtatt caccatgtta ctgcaatgac agatgatgca      60
gaacgtaatt ataaattttt tacagaagta ctaggcatgc gtttagttaa aagacagtc      120 aatcaagatg atatttatac gtatcatact tttttttgcag atgatgtagg ttcggcaggt     180
acagacatga cgttctttga ttttccaaat attacaaaag ggcaggcagg aacaaattcc     240
```

-continued

```
attacaagac cgtcttttag agtgcctaac gatgacgcat taacatatta tgaacagcgc    300
tttgatgagt ttggtgttaa acacgaaggt attcaagaat tatttggtaa aaaagtgttg    360
ccatttgaag aagtcgatgg ccaagtgtat caattaattt cagatgagtt aaatgaaggg    420
gtagcacctg gtgtaccttg aagaatggga ccggttccag tagataaagc gatttatgga    480
ttaggcccca ttgaaattaa agtaagttat tttgacgact ttaaaaatat tttagagact    540
gtttacggta tgacaactat tgcgcatgaa gataatgtcg cattacttga agttggcgaa    600
ggaggcaatg gtggccaggt aatcttaata aaagatgata aagggccagc agcacgtcaa    660
ggttatggtg aggtacatca tgtgtcattt cgtgtgaaag atcatgatgc aatagaagcg    720
tgggcaacga aatataaaga ggtaggtatt aataactcag gcatcgttaa tcgtttctat    780
tttgaagcat tatatgcacg tgtggggcat atttttaatag aaatttcaac agatggacca    840
ggatttatgg aagatgaacc ttatgaaaca ttaggcgaag ggttatcctt accaccattt    900
ttagaaaata aaagagaata tattgaatcg gaagttagac cttttaatac gaagcgtcaa    960
catggttaa                                                            969
```

<210> SEQ ID NO 12
<211> LENGTH: 322
<212> TYPE: PRT
<213> ORGANISM: Staphylococcus aureus

<400> SEQUENCE: 12

```
Met Ile Asn Asn His Glu Leu Leu Gly Ile His His Val Thr Ala Met
1               5                   10                  15

Thr Asp Asp Ala Glu Arg Asn Tyr Lys Phe Phe Thr Glu Val Leu Gly
            20                  25                  30

Met Arg Leu Val Lys Lys Thr Val Asn Gln Asp Asp Ile Tyr Thr Tyr
        35                  40                  45

His Thr Phe Phe Ala Asp Val Gly Ser Ala Gly Thr Asp Met Thr
    50                  55                  60

Phe Phe Asp Phe Pro Asn Ile Thr Lys Gly Gln Ala Gly Thr Asn Ser
65                  70                  75                  80

Ile Thr Arg Pro Ser Phe Arg Val Pro Asn Asp Asp Ala Leu Thr Tyr
                85                  90                  95

Tyr Glu Gln Arg Phe Asp Glu Phe Gly Val Lys His Glu Gly Ile Gln
            100                 105                 110

Glu Leu Phe Gly Lys Lys Val Leu Pro Phe Glu Glu Val Asp Gly Gln
        115                 120                 125

Val Tyr Gln Leu Ile Ser Asp Glu Leu Asn Glu Gly Val Ala Pro Gly
    130                 135                 140

Val Pro Trp Lys Asn Gly Pro Val Pro Val Asp Lys Ala Ile Tyr Gly
145                 150                 155                 160

Leu Gly Pro Ile Glu Ile Lys Val Ser Tyr Phe Asp Asp Phe Lys Asn
                165                 170                 175

Ile Leu Glu Thr Val Tyr Gly Met Thr Thr Ile Ala His Glu Asp Asn
            180                 185                 190

Val Ala Leu Leu Glu Val Gly Glu Gly Gly Asn Gly Gly Gln Val Ile
        195                 200                 205

Leu Ile Lys Asp Asp Lys Gly Pro Ala Ala Arg Gln Gly Tyr Gly Glu
    210                 215                 220

Val His His Val Ser Phe Arg Val Lys Asp His Asp Ala Ile Glu Ala
225                 230                 235                 240
```

```
Trp Ala Thr Lys Tyr Lys Glu Val Gly Ile Asn Asn Ser Gly Ile Val
                245                 250                 255

Asn Arg Phe Tyr Phe Glu Ala Leu Tyr Ala Arg Val Gly His Ile Leu
            260                 265                 270

Ile Glu Ile Ser Thr Asp Gly Pro Gly Phe Met Glu Asp Glu Pro Tyr
        275                 280                 285

Glu Thr Leu Gly Glu Gly Leu Ser Leu Pro Pro Phe Leu Glu Asn Lys
    290                 295                 300

Arg Glu Tyr Ile Glu Ser Glu Val Arg Pro Phe Asn Thr Lys Arg Gln
305                 310                 315                 320

His Gly
```

<210> SEQ ID NO 13
<211> LENGTH: 1100
<212> TYPE: DNA
<213> ORGANISM: Staphylococcus aureus

<400> SEQUENCE: 13

```
gggacatttt taaatcatgc atgcgtatct taaaagagtc cattattgtg gcatttgcct      60
ttgttggtgt tgtcgttggt gccggctttg ctactggtca agaaattttc cagttttca     120
caagtcatgg cgcatatagc atttcaggca ttattgtaac aggactattg attactttag    180
gtggaatggt tgtcatgcat acaggtcatc atctaaagtc cagaaatcat tctgattcaa    240
ttaactattt cttataccc tctattgcaa gaggttttga tattatttta acaatgttta    300
tgttgtcttt agctattatt atgactgcag gtggtgcgtc aaccattcat caaagtttca    360
acttaccgta ttggctgagc gcactcatat tagtcgcctt tattttagca acactgtttc    420
taaaattcga tcgtttaatt gctgtgcttg gcggtgttac cccatttta attgcgattg    480
tcattatgat tgcggtctac tatttcacaa caagtcatct tgattttact gccgctaata    540
atgatgctca gattcataag cagaaatcat tatcacctgg atggtggttt gatgcgatta    600
actatgcaag cttgcaaatt gctgctgcct tcagcttctt atcagtgatg gtagtaaag     660
ttaaatatcg tgactcaacg ttatacgggg gcttgattgg cggtttaatc attacatttt    720
tactcatgat gattaatcta ggtttaatt ctcaattcga taaaattaaa cacgtagatc    780
tacctacatt aaaattagcg acacaaatgt ctccgtcaat tggtattatt atgtctgtca    840
ttatgatact tgtcatctac aatactgttg ttggattaat gtatgcattt gcgtcacgtt    900
tcagcgttcc attcagcaga cgttacttca tcattattat tacaatggct gtcatcactt    960
atattagtac atttatcggt ttcatttcat taattggaaa agtattccct attatgggat   1020
tgttcggttt catcttactc ataccctgtac tctataaagg tttaattaag cgtattaccg   1080
gcaaatctca tatcgattaa                                                1100
```

<210> SEQ ID NO 14
<211> LENGTH: 359
<212> TYPE: PRT
<213> ORGANISM: Staphylococcus aureus

<400> SEQUENCE: 14

```
Met Arg Ile Leu Lys Glu Ser Ile Ile Val Ala Phe Ala Phe Val Gly
1               5                   10                  15

Val Val Val Gly Ala Gly Phe Ala Thr Gly Gln Glu Ile Phe Gln Phe
            20                  25                  30

Phe Thr Ser His Gly Ala Tyr Ser Ile Ser Gly Ile Ile Val Thr Gly
        35                  40                  45
```

```
Leu Leu Ile Thr Leu Gly Gly Met Val Val Met His Thr Gly His His
    50                  55                  60

Leu Lys Ser Arg Asn His Ser Asp Ser Ile Asn Tyr Phe Leu Tyr Pro
65                  70                  75                  80

Ser Ile Ala Arg Gly Phe Asp Ile Ile Leu Thr Met Phe Met Leu Ser
                85                  90                  95

Leu Ala Ile Ile Met Thr Ala Gly Gly Ala Ser Thr Ile His Gln Ser
            100                 105                 110

Phe Asn Leu Pro Tyr Trp Leu Ser Ala Leu Ile Leu Val Ala Phe Ile
        115                 120                 125

Leu Ala Thr Leu Phe Leu Lys Phe Asp Arg Leu Ile Ala Val Leu Gly
    130                 135                 140

Gly Val Thr Pro Phe Leu Ile Ala Ile Val Ile Met Ile Ala Val Tyr
145                 150                 155                 160

Tyr Phe Thr Thr Ser His Leu Asp Phe Thr Ala Ala Asn Asn Asp Ala
                165                 170                 175

Gln Ile His Lys Gln Lys Ser Leu Ser Pro Gly Trp Trp Phe Asp Ala
            180                 185                 190

Ile Asn Tyr Ala Ser Leu Gln Ile Ala Ala Ala Phe Ser Phe Leu Ser
        195                 200                 205

Val Met Gly Ser Lys Val Lys Tyr Arg Asp Ser Thr Leu Tyr Gly Gly
    210                 215                 220

Leu Ile Gly Gly Leu Ile Ile Thr Phe Leu Leu Met Met Ile Asn Leu
225                 230                 235                 240

Gly Leu Ile Ser Gln Phe Asp Lys Ile Lys His Val Asp Leu Pro Thr
                245                 250                 255

Leu Lys Leu Ala Thr Gln Met Ser Pro Ser Ile Gly Ile Ile Met Ser
            260                 265                 270

Val Ile Met Ile Leu Val Ile Tyr Asn Thr Val Val Gly Leu Met Tyr
        275                 280                 285

Ala Phe Ala Ser Arg Phe Ser Val Pro Phe Ser Arg Arg Tyr Phe Ile
    290                 295                 300

Ile Ile Ile Thr Met Ala Val Ile Thr Tyr Ile Ser Thr Phe Ile Gly
305                 310                 315                 320

Phe Ile Ser Leu Ile Gly Lys Val Phe Pro Ile Met Gly Leu Phe Gly
                325                 330                 335

Phe Ile Leu Leu Ile Pro Val Leu Tyr Lys Gly Leu Ile Lys Arg Ile
            340                 345                 350

Thr Gly Lys Ser His Ile Asp
        355

<210> SEQ ID NO 15
<211> LENGTH: 774
<212> TYPE: DNA
<213> ORGANISM: Staphylococcus aureus

<400> SEQUENCE: 15
atgttaatcg atacacatgt ccatttaaat gatgagcaat acgatgatga tttgagtgaa      60
gtgattacac gtgctagaga agcaggtgtt gatcgtatgt ttgtagttgg ttttaacaaa     120
tcgacaattg aacgcgcgat gaaattaatc gatgagtatg attttttata tggcattatc     180
ggttggcatc cagttgacgc aattgatttt acagaagaac acttggaatg gattgaatct     240
ttagctcagc atccaaaagt gattggtatt ggtgaaatgg gattagatta tcactgggat     300
```

-continued

| | |
|---|---|
| aaatctcctg cagatgttca aaaggaagtt tttagaaagc aaattgcttt agctaagcgt | 360 |
| ttgaagttac caattatcat tcataaccgt gaagcaactc aagactgtat cgatatctta | 420 |
| ttggaggagc atgctgaaga ggtaggcggg attatgcata gctttagtgg ttctccagaa | 480 |
| attgcagata ttgtaactaa taagctgaat ttttatattt cattaggtgg acctgtgaca | 540 |
| tttaaaaatg ctaaacagcc taagaagtt gctaagcatg tgtcaatgga gcgtttgcta | 600 |
| gttgaaaccg atgcaccgta tctttcgcca catccgtata gagggaagcg aaatgaaccg | 660 |
| gcgagagtaa ctttagtagc tgaacaaatt gctgaattaa aaggcttatc ttatgaagaa | 720 |
| gtgtgcgaac aaacaactaa aaatgcagag aaattgttta atttaaattc ataa | 774 |

<210> SEQ ID NO 16
<211> LENGTH: 257
<212> TYPE: PRT
<213> ORGANISM: Staphylococcus aureus

<400> SEQUENCE: 16

```
Met Leu Ile Asp Thr His Val His Leu Asn Asp Glu Gln Tyr Asp Asp
1               5                   10                  15

Asp Leu Ser Glu Val Ile Thr Arg Ala Arg Glu Ala Gly Val Asp Arg
            20                  25                  30

Met Phe Val Val Gly Phe Asn Lys Ser Thr Ile Glu Arg Ala Met Lys
        35                  40                  45

Leu Ile Asp Glu Tyr Asp Phe Leu Tyr Gly Ile Ile Gly Trp His Pro
    50                  55                  60

Val Asp Ala Ile Asp Phe Thr Glu Glu His Leu Glu Trp Ile Glu Ser
65                  70                  75                  80

Leu Ala Gln His Pro Lys Val Ile Gly Ile Gly Glu Met Gly Leu Asp
                85                  90                  95

Tyr His Trp Asp Lys Ser Pro Ala Asp Val Gln Lys Glu Val Phe Arg
            100                 105                 110

Lys Gln Ile Ala Leu Ala Lys Arg Leu Lys Leu Pro Ile Ile Ile His
        115                 120                 125

Asn Arg Glu Ala Thr Gln Asp Cys Ile Asp Ile Leu Glu Glu His
    130                 135                 140

Ala Glu Glu Val Gly Gly Ile Met His Ser Phe Ser Gly Ser Pro Glu
145                 150                 155                 160

Ile Ala Asp Ile Val Thr Asn Lys Leu Asn Phe Tyr Ile Ser Leu Gly
                165                 170                 175

Gly Pro Val Thr Phe Lys Asn Ala Lys Gln Pro Lys Glu Val Ala Lys
            180                 185                 190

His Val Ser Met Glu Arg Leu Leu Val Glu Thr Asp Ala Pro Tyr Leu
        195                 200                 205

Ser Pro His Pro Tyr Arg Gly Lys Arg Asn Glu Pro Ala Arg Val Thr
    210                 215                 220

Leu Val Ala Glu Gln Ile Ala Glu Leu Lys Gly Leu Ser Tyr Glu Glu
225                 230                 235                 240

Val Cys Glu Gln Thr Thr Lys Asn Ala Glu Lys Leu Phe Asn Leu Asn
                245                 250                 255

Ser
```

<210> SEQ ID NO 17
<211> LENGTH: 2123
<212> TYPE: DNA
<213> ORGANISM: Staphylococcus aureus

<400> SEQUENCE: 17

```
atgataatat attggtgtat gacagttaat ggagggaacg aaatgaaagc tttattactt      60
aaaacaagtg tatggctcgt tttgctttt agtgtaatgg gattatggca agtctcgaac     120
gcggctgagc agcatacacc aatgaaagca catgcagtaa caacgataga caaagcaaca    180
acagataagc aacaagtacc gccaacaaag gaagcggctc atcattctgg caaagaagcg    240
gcaaccaacg tatcagcatc agcgcaggga acagctgatg atacaaacag caaagtaaca    300
tccaacgcac catctaacaa accatctaca gtagtttcaa caaaagtaaa cgaaacacgc    360
gacgtagata cacaacaagc ctcaacacaa aaaccaactc acacagcaac gttcaaatta    420
tcaaatgcta aaacagcatc actttcacca cgaatgtttg ctgctaatgc accacaaaca    480
acaacacata aaatattaca tacaaatgat atccatggcc gactagccga agaaaaaggg    540
cgtgtcatcg gtatggctaa attaaaaaca gtaaaagaac aagaaaagcc tgatttaatg    600
ttagacgcag gagacgcctt ccaaggttta ccactttcaa accagtctaa aggtgaagaa    660
atggctaaag caatgaatgc agtaggttat gatgctatgg cagtcggtaa ccatgaattt    720
gactttggat acgatcagtt gaaaaagtta gagggtatgt tagacttccc gatgctaagt    780
actaacgttt ataaagatgg aaaacgcgcg tttaagcctt caacgattgt aacaaaaaat    840
ggtattcgtt atggaattat tggtgtaacg acaccagaaa caaagacgaa acaagacct     900
gaaggcatta aggcgttga  atttagagat ccattacaaa gtgtgacagc ggaaatgatg    960
cgtatttata aagacgtaga tacatttgtt gttatatcac atttaggaat tgatccttca   1020
acacaagaaa catggcgtgg tgattactta gtgaaacaat taagtcaaaa tccacaattg   1080
aagaaacgta ttacagttat tgatggtcat tcacatacag tacttcaaaa tggtcaaatt   1140
tataacaatg atgcattggc acaaacaggt acagcacttg cgaatatcgg taagattaca   1200
tttaattatc gcaatggaga ggtatcgaat attaaaccgt cattgattaa tgttaaagac   1260
gttgaaaatg taacaccgaa caaagcatta gctgaacaaa ttaatcaagc tgatcaaaca   1320
tttagagcac aaactgcaga ggtaattatt ccaaacaata ccattgattt caaaggagaa   1380
agagatgacg ttagaacgcg tgaaacaaat ttaggaaacg cgattgcaga tgctatggaa   1440
gcgtatggcg ttaagaattt ctctaaaaag actgactttg ccgtgacaaa tggtggaggt   1500
attcgtgcct ctatcgcaaa aggtaaggtg acacgctatg atttaatctc agtattacca   1560
tttggaaata cgattgcgca aattgatgta aaaggttcag acgtctggac ggctttcgaa   1620
catagtttag gcgcaccaac aacacaaaag gacggtaaga cagtgttaac agcgaatggc   1680
ggtttactac atatctctga ttcaatccgt gtttactatg atataaataa accgtctggc   1740
aaacgaatta atgctattca aatttttaaat aaagagacag gtaagtttga aaatattgat   1800
ttaaaacgtg tatatcacgt aacgatgaat gacttcacag catcaggtgg gacggatata   1860
gtatgttcgg tggtcctaga aagaaggta  tttcattaga tcaagtacta gcaagttatt   1920
taaaaacagc taacttagct aagtatgata cgacagaacc acaacgtatg ttattaggta   1980
aaccagcagt aagtgaacaa ccagctaaag gacaacaagg tagcaaaggt agtaagtctg   2040
gtaaagatac acaaccaatt ggtgacgaca agtgatggga tccagcgaaa aaaccagctc   2100
caggtaaagt tgtattgttg tag                                           2123
```

<210> SEQ ID NO 18
<211> LENGTH: 707
<212> TYPE: PRT

-continued

<213> ORGANISM: Staphylococcus aureus

<400> SEQUENCE: 18

| | | | | | | | | | | | | | | |
|---|---|---|---|---|---|---|---|---|---|---|---|---|---|---|
| Met | Ile | Ile | Tyr | Trp | Cys | Met | Thr | Val | Asn | Gly | Gly | Asn | Glu | Met | Lys |
| 1 | | | | 5 | | | | | 10 | | | | | 15 | |
| Ala | Leu | Leu | Leu | Lys | Thr | Ser | Val | Trp | Leu | Val | Leu | Leu | Phe | Ser | Val |
| | | | 20 | | | | | 25 | | | | | 30 | | |
| Met | Gly | Leu | Trp | Gln | Val | Ser | Asn | Ala | Ala | Glu | Gln | His | Thr | Pro | Met |
| | | 35 | | | | | 40 | | | | | 45 | | | |
| Lys | Ala | His | Ala | Val | Thr | Thr | Ile | Asp | Lys | Ala | Thr | Thr | Asp | Lys | Gln |
| | 50 | | | | | 55 | | | | | 60 | | | | |
| Gln | Val | Pro | Pro | Thr | Lys | Glu | Ala | Ala | His | His | Ser | Gly | Lys | Glu | Ala |
| 65 | | | | | 70 | | | | 75 | | | | | | 80 |
| Ala | Thr | Asn | Val | Ser | Ala | Ser | Ala | Gln | Gly | Thr | Ala | Asp | Asp | Thr | Asn |
| | | | | 85 | | | | | 90 | | | | | 95 | |
| Ser | Lys | Val | Thr | Ser | Asn | Ala | Pro | Ser | Asn | Lys | Pro | Ser | Thr | Val | Val |
| | | | 100 | | | | | 105 | | | | | 110 | | |
| Ser | Thr | Lys | Val | Asn | Glu | Thr | Arg | Asp | Val | Asp | Thr | Gln | Gln | Ala | Ser |
| | | 115 | | | | | 120 | | | | | 125 | | | |
| Thr | Gln | Lys | Pro | Thr | His | Thr | Ala | Thr | Phe | Lys | Leu | Ser | Asn | Ala | Lys |
| | 130 | | | | | 135 | | | | | 140 | | | | |
| Thr | Ala | Ser | Leu | Ser | Pro | Arg | Met | Phe | Ala | Ala | Asn | Ala | Pro | Gln | Thr |
| 145 | | | | | 150 | | | | | 155 | | | | | 160 |
| Thr | Thr | His | Lys | Ile | Leu | His | Thr | Asn | Asp | Ile | His | Gly | Arg | Leu | Ala |
| | | | | 165 | | | | | 170 | | | | | 175 | |
| Glu | Glu | Lys | Gly | Arg | Val | Ile | Gly | Met | Ala | Lys | Leu | Lys | Thr | Val | Lys |
| | | | 180 | | | | | 185 | | | | | 190 | | |
| Glu | Gln | Glu | Lys | Pro | Asp | Leu | Met | Leu | Asp | Ala | Gly | Asp | Ala | Phe | Gln |
| | | 195 | | | | | 200 | | | | | 205 | | | |
| Gly | Leu | Pro | Leu | Ser | Asn | Gln | Ser | Lys | Gly | Glu | Glu | Met | Ala | Lys | Ala |
| | 210 | | | | | 215 | | | | | 220 | | | | |
| Met | Asn | Ala | Val | Gly | Tyr | Asp | Ala | Met | Ala | Val | Gly | Asn | His | Glu | Phe |
| 225 | | | | | 230 | | | | | 235 | | | | | 240 |
| Asp | Phe | Gly | Tyr | Asp | Gln | Leu | Lys | Lys | Leu | Glu | Gly | Met | Leu | Asp | Phe |
| | | | | 245 | | | | | 250 | | | | | 255 | |
| Pro | Met | Leu | Ser | Thr | Asn | Val | Tyr | Lys | Asp | Gly | Lys | Arg | Ala | Phe | Lys |
| | | | 260 | | | | | 265 | | | | | 270 | | |
| Pro | Ser | Thr | Ile | Val | Thr | Lys | Asn | Gly | Ile | Arg | Tyr | Gly | Ile | Ile | Gly |
| | | 275 | | | | | 280 | | | | | 285 | | | |
| Val | Thr | Thr | Pro | Glu | Thr | Lys | Thr | Lys | Thr | Arg | Pro | Glu | Gly | Ile | Lys |
| | 290 | | | | | 295 | | | | | 300 | | | | |
| Gly | Val | Glu | Phe | Arg | Asp | Pro | Leu | Gln | Ser | Val | Thr | Ala | Glu | Met | Met |
| 305 | | | | | 310 | | | | | 315 | | | | | 320 |
| Arg | Ile | Tyr | Lys | Asp | Val | Asp | Thr | Phe | Val | Val | Ile | Ser | His | Leu | Gly |
| | | | | 325 | | | | | 330 | | | | | 335 | |
| Ile | Asp | Pro | Ser | Thr | Gln | Glu | Thr | Trp | Arg | Gly | Asp | Tyr | Leu | Val | Lys |
| | | | 340 | | | | | 345 | | | | | 350 | | |
| Gln | Leu | Ser | Gln | Asn | Pro | Gln | Leu | Lys | Lys | Arg | Ile | Thr | Val | Ile | Asp |
| | | 355 | | | | | 360 | | | | | 365 | | | |
| Gly | His | Ser | His | Thr | Val | Leu | Gln | Asn | Gly | Gln | Ile | Tyr | Asn | Asn | Asp |
| | 370 | | | | | 375 | | | | | 380 | | | | |
| Ala | Leu | Ala | Gln | Thr | Gly | Thr | Ala | Leu | Ala | Asn | Ile | Gly | Lys | Ile | Thr |
| 385 | | | | | 390 | | | | | 395 | | | | | 400 |

```
Phe Asn Tyr Arg Asn Gly Glu Val Ser Asn Ile Lys Pro Ser Leu Ile
                405                 410                 415
Asn Val Lys Asp Val Glu Asn Val Thr Pro Asn Lys Ala Leu Ala Glu
            420                 425                 430
Gln Ile Asn Gln Ala Asp Gln Thr Phe Arg Ala Gln Thr Ala Glu Val
        435                 440                 445
Ile Ile Pro Asn Asn Thr Ile Asp Phe Lys Gly Glu Arg Asp Asp Val
    450                 455                 460
Arg Thr Arg Glu Thr Asn Leu Gly Asn Ala Ile Ala Asp Ala Met Glu
465                 470                 475                 480
Ala Tyr Gly Val Lys Asn Phe Ser Lys Lys Thr Asp Phe Ala Val Thr
                485                 490                 495
Asn Gly Gly Gly Ile Arg Ala Ser Ile Ala Lys Gly Lys Val Thr Arg
            500                 505                 510
Tyr Asp Leu Ile Ser Val Leu Pro Phe Gly Asn Thr Ile Ala Gln Ile
        515                 520                 525
Asp Val Lys Gly Ser Asp Val Trp Thr Ala Phe Glu His Ser Leu Gly
    530                 535                 540
Ala Pro Thr Thr Gln Lys Asp Gly Lys Thr Val Leu Thr Ala Asn Gly
545                 550                 555                 560
Gly Leu Leu His Ile Ser Asp Ser Ile Arg Val Tyr Tyr Asp Ile Asn
                565                 570                 575
Lys Pro Ser Gly Lys Arg Ile Asn Ala Ile Gln Ile Leu Asn Lys Glu
            580                 585                 590
Thr Gly Lys Phe Glu Asn Ile Asp Leu Lys Arg Val Tyr His Val Thr
        595                 600                 605
Met Asn Asp Phe Thr Ala Ser Gly Gly Asp Gly Tyr Ser Met Phe Gly
    610                 615                 620
Gly Pro Arg Glu Glu Gly Ile Ser Leu Asp Gln Val Leu Ala Ser Tyr
625                 630                 635                 640
Leu Lys Thr Ala Asn Leu Ala Lys Tyr Asp Thr Thr Glu Pro Gln Arg
                645                 650                 655
Met Leu Leu Gly Lys Pro Ala Val Ser Glu Gln Pro Ala Lys Gly Gln
            660                 665                 670
Gln Gly Ser Lys Gly Ser Lys Ser Gly Lys Asp Thr Gln Pro Ile Gly
        675                 680                 685
Asp Asp Lys Val Met Asp Pro Ala Lys Lys Pro Ala Pro Gly Lys Val
    690                 695                 700
Val Leu Leu
705

<210> SEQ ID NO 19
<211> LENGTH: 912
<212> TYPE: DNA
<213> ORGANISM: Staphylococcus aureus

<400> SEQUENCE: 19
atggataata atgaaaaaga aaaagtaaa  agtgaactat tagttgtaac aggtttatct    60
ggcgcaggta aatctttggt tattcaatgt ttagaagaca tgggatattt tgtgtagat   120 aatctaccac cagtgttatt gcctaaattt gtagagttga tggaacaagg aaatccatcc   180
ttaagaaaag tggcaattgc aattgattta agaggtaagg aactatttaa ttcattagtt   240
gcagtagtgg ataaagtcaa aagtgaaagt gacgtcatca ttgatgttat gttttagaa    300 gcaagtactg aaaattaat  ttcaagatat aaggaaacgc gtcgtgcaca tcctttgatg   360
```

-continued

```
gaacaaggta aaagatcgtt aatcaatgca attaatgatg agcgagagca tttgtctcaa    420
attagaagta tagctaattt tgttatagat actacaaagt tatcacctaa agaattaaaa    480
gaacgcattc gtcgatacta tgaagatgaa gagtttgaaa cttttacaat taatgtcaca    540
agtttcggtt ttaaacatgg gattcagatg gatgcagatt tagtatttga tgtacgattt    600
ttaccaaatc catattatgt agtagattta agacctttaa caggattaga taaagacgtt    660
tataattatg ttatgaaatg gaaagagacg gagattttct ttgaaaaatt aactgatttg    720
ttagatttta tgatacccgg gtataaaaaa gaagggaaat ctcaattagt aattgccatc    780
ggttgtacgg gtggacaaca tcgatctgta gcattagcag aacgactagg taattatcta    840
aatgaagtat ttgaatataa tgtttatgtg catcataggg acgcacatat tgaaagtggc    900
gagaaaaaat ga                                                        912
```

<210> SEQ ID NO 20
<211> LENGTH: 303
<212> TYPE: PRT
<213> ORGANISM: Staphylococcus aureus

<400> SEQUENCE: 20

```
Met Asp Asn Asn Glu Lys Glu Lys Ser Lys Ser Glu Leu Leu Val Val
1               5                   10                  15

Thr Gly Leu Ser Gly Ala Gly Lys Ser Leu Val Ile Gln Cys Leu Glu
                20                  25                  30

Asp Met Gly Tyr Phe Cys Val Asp Asn Leu Pro Pro Val Leu Leu Pro
            35                  40                  45

Lys Phe Val Glu Leu Met Glu Gln Gly Asn Pro Ser Leu Arg Lys Val
        50                  55                  60

Ala Ile Ala Ile Asp Leu Arg Gly Lys Glu Leu Phe Asn Ser Leu Val
65                  70                  75                  80

Ala Val Val Asp Lys Val Lys Ser Glu Ser Asp Val Ile Ile Asp Val
                85                  90                  95

Met Phe Leu Glu Ala Ser Thr Glu Lys Leu Ile Ser Arg Tyr Lys Glu
            100                 105                 110

Thr Arg Arg Ala His Pro Leu Met Glu Gln Gly Lys Arg Ser Leu Ile
        115                 120                 125

Asn Ala Ile Asn Asp Glu Arg Glu His Leu Ser Gln Ile Arg Ser Ile
    130                 135                 140

Ala Asn Phe Val Ile Asp Thr Thr Lys Leu Ser Pro Lys Glu Leu Lys
145                 150                 155                 160

Glu Arg Ile Arg Arg Tyr Tyr Glu Asp Glu Glu Phe Glu Thr Phe Thr
                165                 170                 175

Ile Asn Val Thr Ser Phe Gly Phe Lys His Gly Ile Gln Met Asp Ala
            180                 185                 190

Asp Leu Val Phe Asp Val Arg Phe Leu Pro Asn Pro Tyr Tyr Val Val
        195                 200                 205

Asp Leu Arg Pro Leu Thr Gly Leu Asp Lys Asp Val Tyr Asn Tyr Val
    210                 215                 220

Met Lys Trp Lys Glu Thr Glu Ile Phe Phe Glu Lys Leu Thr Asp Leu
225                 230                 235                 240

Leu Asp Phe Met Ile Pro Gly Tyr Lys Lys Glu Gly Lys Ser Gln Leu
                245                 250                 255

Val Ile Ala Ile Gly Cys Thr Gly Gly Gln His Arg Ser Val Ala Leu
            260                 265                 270
```

```
Ala Glu Arg Leu Gly Asn Tyr Leu Asn Glu Val Phe Glu Tyr Asn Val
        275                 280                 285

Tyr Val His His Arg Asp Ala His Ile Glu Ser Gly Glu Lys Lys
        290                 295                 300

<210> SEQ ID NO 21
<211> LENGTH: 1482
<212> TYPE: DNA
<213> ORGANISM: Staphylococcus aureus

<400> SEQUENCE: 21
atgcgattta cattttcaaa cgatttagga acgttattta ctattatttt agccattgga      60
ttcatcatta atttagtatt ggcttttatt attatctttt tagaaagaaa taggcgtaca     120
gcgagttcaa cttgggcatg ctatttgta cttttgtct taccattgat tggtttatt       180 ctttacttgt tttttggtag aaccgtttcg cacgcaaat tgaataaaaa caatggtaac      240
gtgttaacgg atttcgatgg acttttaaaa caacaaatag aaagctttga taaaggtaat     300
tatggtactg ataacaaaca agttcaaaaa catcatgatt tagtacgtat gcttttgatg     360
gatcaagatg gttttttaac tgaaaataat aaagttgatc atttcattga tggaaatgat     420
ttatatgatc aagttttaaa agatattaaa atgcaaaag aatatatcca tttagagtac     480
tatactttcg ctttagatgg tttaggtaaa agaattttac atgctttaga agaaaaattg     540
aaacaaggtc tagaagtaaa atatattatat gatgatgttg atctaaaaa tgttaagatg     600 gcaaattttg atcattttaa atcgttaggt ggagaagttg aagcattttt tgcttcaaaa     660
ttaccgttat tgaatttcag aatgaataat agaaatcata gaaaatcat cgtaatcgat     720 ggtcaactag gttatgtcgg aggatttaac attggtgatg aatatctagg attaggaaaa     780
ttaggatatt ggagagatac gcatttacgt atacaagggg atgcggttga tgcactgcag     840
ttgcgattta ttttagactg gaattcgcaa gcgcaccgtc acaatttga atatgatgtt      900 aagtatttcc ctaaaaagaa cggaccattg gcaattcac caattcaaat agctgcaagt     960
ggcccggcta gtgactggca tcaaattgaa tacggttata caaaaatgat tatgagtgca    1020
aagaaatctg tatatttaca atcaccatat tcattccgg ataattcata tataaatgcc    1080
attaaaattg ctgctaaatc aggtgtagat gtacatttaa tgattccatg taagccagat    1140
catccattag tatattgggc gacattttca aatgcctctg acttattatc aagtggtgtt    1200
aaaatttata cgtatgaaaa tggatttata cattctaaaa tgtgcttaat tgatgatgaa    1260
atcgtatcag tgggcacagc aaatatggac tttagaagtt ttgaattaaa ttttgaagta    1320
aatgcctttg tatatgatga aaatcttgct aaagatttaa gggtggctta tgaacatgat    1380
attacaaaat caaacaaact aaccaaagaa tcatatgcca atagaccgct gtctgttaaa    1440
ttcaaagaat cgttagcaaa attagtttcg ccaatttat aa                        1482

<210> SEQ ID NO 22
<211> LENGTH: 493
<212> TYPE: PRT
<213> ORGANISM: Staphylococcus aureus

<400> SEQUENCE: 22

Met Arg Phe Thr Phe Ser Asn Asp Leu Gly Thr Leu Phe Thr Ile Ile
1               5                   10                  15

Leu Ala Ile Gly Phe Ile Ile Asn Leu Val Leu Ala Phe Ile Ile Ile
            20                  25                  30
```

```
Phe Leu Glu Arg Asn Arg Arg Thr Ala Ser Ser Thr Trp Ala Trp Leu
         35                  40                  45

Phe Val Leu Phe Val Leu Pro Leu Ile Gly Phe Ile Leu Tyr Leu Phe
     50                  55                  60

Phe Gly Arg Thr Val Ser Ala Arg Lys Leu Asn Lys Asn Asn Gly Asn
 65                  70                  75                  80

Val Leu Thr Asp Phe Asp Gly Leu Leu Lys Gln Gln Ile Glu Ser Phe
                 85                  90                  95

Asp Lys Gly Asn Tyr Gly Thr Asp Asn Lys Gln Val Gln Lys His His
            100                 105                 110

Asp Leu Val Arg Met Leu Leu Met Asp Gln Asp Gly Phe Leu Thr Glu
            115                 120                 125

Asn Asn Lys Val Asp His Phe Ile Asp Gly Asn Asp Leu Tyr Asp Gln
        130                 135                 140

Val Leu Lys Asp Ile Lys Asn Ala Lys Glu Tyr Ile His Leu Glu Tyr
145                 150                 155                 160

Tyr Thr Phe Ala Leu Asp Gly Leu Gly Lys Arg Ile Leu His Ala Leu
                165                 170                 175

Glu Glu Lys Leu Lys Gln Gly Leu Glu Val Lys Ile Leu Tyr Asp Asp
            180                 185                 190

Val Gly Ser Lys Asn Val Lys Met Ala Asn Phe Asp His Phe Lys Ser
        195                 200                 205

Leu Gly Gly Glu Val Glu Ala Phe Phe Ala Ser Lys Leu Pro Leu Leu
    210                 215                 220

Asn Phe Arg Met Asn Asn Arg Asn His Arg Lys Ile Ile Val Ile Asp
225                 230                 235                 240

Gly Gln Leu Gly Tyr Val Gly Gly Phe Asn Ile Gly Asp Glu Tyr Leu
                245                 250                 255

Gly Leu Gly Lys Leu Gly Tyr Trp Arg Asp Thr His Leu Arg Ile Gln
            260                 265                 270

Gly Asp Ala Val Asp Ala Leu Gln Leu Arg Phe Ile Leu Asp Trp Asn
        275                 280                 285

Ser Gln Ala His Arg Pro Gln Phe Glu Tyr Asp Val Lys Tyr Phe Pro
    290                 295                 300

Lys Lys Asn Gly Pro Leu Gly Asn Ser Pro Ile Gln Ile Ala Ala Ser
305                 310                 315                 320

Gly Pro Ala Ser Asp Trp His Gln Ile Glu Tyr Gly Tyr Thr Lys Met
                325                 330                 335

Ile Met Ser Ala Lys Lys Ser Val Tyr Leu Gln Ser Pro Tyr Phe Ile
            340                 345                 350

Pro Asp Asn Ser Tyr Ile Asn Ala Ile Lys Ile Ala Ala Lys Ser Gly
        355                 360                 365

Val Asp Val His Leu Met Ile Pro Cys Lys Pro Asp His Pro Leu Val
    370                 375                 380

Tyr Trp Ala Thr Phe Ser Asn Ala Ser Asp Leu Leu Ser Ser Gly Val
385                 390                 395                 400

Lys Ile Tyr Thr Tyr Glu Asn Gly Phe Ile His Ser Lys Met Cys Leu
                405                 410                 415

Ile Asp Asp Glu Ile Val Ser Val Gly Thr Ala Asn Met Asp Phe Arg
            420                 425                 430

Ser Phe Glu Leu Asn Phe Glu Val Asn Ala Phe Val Tyr Asp Glu Asn
        435                 440                 445

Leu Ala Lys Asp Leu Arg Val Ala Tyr Glu His Asp Ile Thr Lys Ser
```

```
                450             455             460
Lys Gln Leu Thr Lys Glu Ser Tyr Ala Asn Arg Pro Leu Ser Val Lys
465             470             475             480

Phe Lys Glu Ser Leu Ala Lys Leu Val Ser Pro Ile Leu
                485             490
```

<210> SEQ ID NO 23
<211> LENGTH: 420
<212> TYPE: DNA
<213> ORGANISM: Staphylococcus aureus

<400> SEQUENCE: 23

```
atgaagattt tattcgtttg tacaggtaac acatgtcgta gcccattagc ggaaagtatt      60
gcaaaagagg ttatgccaaa tcatcaattt gaatcaagag gtatattcgc tgtgaacaat     120
caaggtgttt cgaattatgt tgaagactta gttgaagaac atcatttagc tgaaacgacc     180
ttatcgcaac aatttactga agcagatttg aaagcagata ttattttgac gatgtcgtat     240
tcgcacaaag aattaataga ggcacacttt ggtttgcaaa atcatgtttt cacattgcat     300
gaatatgtaa agaagcagg agaagttata gatccatacg gtggaacaaa agaaatgtat     360
gtacatacct atgaagaact tgtaagttta attttaaaat taaagatat tatttgctag      420
```

<210> SEQ ID NO 24
<211> LENGTH: 139
<212> TYPE: PRT
<213> ORGANISM: Staphylococcus aureus

<400> SEQUENCE: 24

```
Met Lys Ile Leu Phe Val Cys Thr Gly Asn Thr Cys Arg Ser Pro Leu
1               5                   10                  15

Ala Glu Ser Ile Ala Lys Glu Val Met Pro Asn His Gln Phe Glu Ser
                20                  25                  30

Arg Gly Ile Phe Ala Val Asn Asn Gln Gly Val Ser Asn Tyr Val Glu
            35                  40                  45

Asp Leu Val Glu Glu His His Leu Ala Glu Thr Thr Leu Ser Gln Gln
        50                  55                  60

Phe Thr Glu Ala Asp Leu Lys Ala Asp Ile Ile Leu Thr Met Ser Tyr
65                  70                  75                  80

Ser His Lys Glu Leu Ile Glu Ala His Phe Gly Leu Gln Asn His Val
                85                  90                  95

Phe Thr Leu His Glu Tyr Val Lys Glu Ala Gly Glu Val Ile Asp Pro
            100                 105                 110

Tyr Gly Gly Thr Lys Glu Met Tyr Val His Thr Tyr Glu Glu Leu Val
        115                 120                 125

Ser Leu Ile Leu Lys Leu Lys Asp Ile Ile Cys
    130                 135
```

<210> SEQ ID NO 25
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 25

```
atatatctgc agtgataaat tgccaagcgt gac                                   33
```

<210> SEQ ID NO 26

<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 26
atatatgagc tctcttgtac agatttaggt ggc          33

<210> SEQ ID NO 27
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 27
atatatctgc agcaagtatt aggtgaagaa ggg          33

<210> SEQ ID NO 28
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 28
atatatgagc tcacggattg atcccaataa tgc          33

<210> SEQ ID NO 29
<211> LENGTH: 36
<212> TYPE: DNA
<213> ORGANISM: Artificial Sequence
<220> FEATURE:
<223> OTHER INFORMATION: Oligonucleotide Primer.

<400> SEQUENCE: 29
atatatctgc agggattca aaacaattt aacatc         36

<210> SEQ ID NO 30
<211> LENGTH: 36
<212> TYPE: DNA
<213> ORGANISM: Artificial Sequence
<220> FEATURE:
<223> OTHER INFORMATION: Oligonucleotide Primer.

<400> SEQUENCE: 30
atatatgagc tcaaggctat taacttgctt atgatc       36

<210> SEQ ID NO 31
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 31
atagatctgc agaagtgttt catcatatca gcg          33

<210> SEQ ID NO 32
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 32
atatatgagc tcacccaagt cgtaataaat tcc    33

<210> SEQ ID NO 33
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 33
atatatctgc agaggtattc accatgttac tgc    33

<210> SEQ ID NO 34
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 34
atatatgagc tcaattgata cacttggcca tcg    33

<210> SEQ ID NO 35
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 35
atatatctgc agaggtattc accatgttac tgc    33

<210> SEQ ID NO 36
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 36
atatatgagc tcaattgata cacttggcca tcg    33

<210> SEQ ID NO 37
<211> LENGTH: 35
<212> TYPE: DNA
<213> ORGANISM: Artificial Sequence
<220> FEATURE:
<223> OTHER INFORMATION: Oligonucleotide Primer.
<221> NAME/KEY: misc_feature
<223> OTHER INFORMATION: Oligonucleotide Primer

<400> SEQUENCE: 37
atatatctgc agggacatt tttaatcatg catgc    35

<210> SEQ ID NO 38
<211> LENGTH: 36
<212> TYPE: DNA
<213> ORGANISM: Artificial Sequence
<220> FEATURE:
<223> OTHER INFORMATION: Oligonucleotide Primer.

<400> SEQUENCE: 38
atatatgagc tcgcagtcat aataatagct aaagac    36

<210> SEQ ID NO 39

<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 39
atatatctgc agtgttaatc gatacacatg tcc        33

<210> SEQ ID NO 40
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 40
atatatgagc tccttcaaac gcttagctaa agc        33

<210> SEQ ID NO 41
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 41
atatatctgc agacaagtgt atggctcgtt ttg        33

<210> SEQ ID NO 42
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 42
atatatgagc tcatttgaac gttgctgtgt gag        33

<210> SEQ ID NO 43
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 43
atatatctgc aggttgtaac aggtttatct ggc        33

<210> SEQ ID NO 44
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 44
atatatgagc tcatttgaga caaatgctct cgc        33

<210> SEQ ID NO 45
<211> LENGTH: 34
<212> TYPE: DNA
<213> ORGANISM: Artificial Sequence
<220> FEATURE:
<223> OTHER INFORMATION: Oligonucleotide Primer.

<400> SEQUENCE: 45
atatatctgc agagagtaca tactttcgct ttag    34

<210> SEQ ID NO 46
<211> LENGTH: 34
<212> TYPE: DNA
<213> ORGANISM: Artificial Sequence
<220> FEATURE:
<223> OTHER INFORMATION: Oligonucleotide Primer.

<400> SEQUENCE: 46
atatatgagc tccctaatcc tagatattca tcac    34

<210> SEQ ID NO 47
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 47
atatatctgc agttgtacag gtaacacatg tcg    33

<210> SEQ ID NO 48
<211> LENGTH: 32
<212> TYPE: DNA
<213> ORGANISM: Artificial Sequence
<220> FEATURE:
<223> OTHER INFORMATION: Oligonucleotide Primer.

<400> SEQUENCE: 48
atatatgagc tcctgctttc aaatctgctc ag    32

<210> SEQ ID NO 49
<211> LENGTH: 731
<212> TYPE: DNA
<213> ORGANISM: Artificial Sequence
<220> FEATURE:
<223> OTHER INFORMATION: Nucleotide sequence of S. aureus coding region
       cloned for expression in E. coli.

<400> SEQUENCE: 49
atgggattaa agtatgaaca tattgctaag caacttaatg cgtttataca tcaatctaat    60
ttcaaacccg gtgataaatt gccaagcgtg acgcaattaa aagaacgtta tcaagtaagt   120
aagagtacta tcattaaagc attaggctta ttggaacaag atggtttgat ctatcaagca   180
caaggcagtg gtatttatgt gagaaatatt gctgatgcca atcgtatcaa cgtctttaag   240
actaatggtt tctctaaaag tttaggtgaa caccgaatga caagtaaggt acttgttttt   300
aaggagattg caacgccacc taatctgta caagatgagc tccaattaaa tgcagatgat   360
accgtctact atttagagcg attaagattc gtggacgatg atgttttatg tatcgaatat   420
tcttattatc ataaagaaat cgtgaaatat ttaaatgatg atattgctaa gggctctatc   480
ttcgactttt agaatcaaac atgaaacttc gtattggttt ttcagatatt ttctttaatg   540
tagatcaact cacttcaagt gaagcttcat tactacaatt gtctacaggt gaaccatgtt   600
tacgttacca ccagactttt tatacaatga ctggcaaacc ctttgattca tctgacatcg   660
tatttcatta tcgtcatgca cagttttata ttcctagtaa aaagagatct catcaccatc   720
accatcacta a    731

<210> SEQ ID NO 50
<211> LENGTH: 243

```
<212> TYPE: PRT
<213> ORGANISM: Artificial Sequence
<220> FEATURE:
<223> OTHER INFORMATION: Amino acid sequence encoded by S. aureus coding
      region cloned for expression in E. coli.

<400> SEQUENCE: 50

Met Gly Leu Lys Tyr Glu His Ile Ala Lys Gln Leu Asn Ala Phe Ile
1               5                   10                  15

His Gln Ser Asn Phe Lys Pro Gly Asp Lys Leu Pro Ser Val Thr Gln
            20                  25                  30

Leu Lys Glu Arg Tyr Gln Val Ser Lys Ser Thr Ile Ile Lys Ala Leu
        35                  40                  45

Gly Leu Leu Glu Gln Asp Gly Leu Ile Tyr Gln Ala Gln Gly Ser Gly
    50                  55                  60

Ile Tyr Val Arg Asn Ile Ala Asp Ala Asn Arg Ile Asn Val Phe Lys
65                  70                  75                  80

Thr Asn Gly Phe Ser Lys Ser Leu Gly Glu His Arg Met Thr Ser Lys
                85                  90                  95

Val Leu Val Phe Lys Glu Ile Ala Thr Pro Pro Lys Ser Val Gln Asp
            100                 105                 110

Glu Leu Gln Leu Asn Ala Asp Asp Thr Val Tyr Tyr Leu Glu Arg Leu
        115                 120                 125

Arg Phe Val Asp Asp Val Leu Cys Ile Glu Tyr Ser Tyr His
    130                 135                 140

Lys Glu Ile Val Lys Tyr Leu Asn Asp Asp Ile Ala Lys Gly Ser Ile
145                 150                 155                 160

Phe Asp Tyr Leu Glu Ser Asn Met Lys Leu Arg Ile Gly Phe Ser Asp
                165                 170                 175

Ile Phe Phe Asn Val Asp Gln Leu Thr Ser Ser Glu Ala Ser Leu Leu
            180                 185                 190

Gln Leu Ser Thr Gly Glu Pro Cys Leu Arg Tyr His Gln Thr Phe Tyr
        195                 200                 205

Thr Met Thr Gly Lys Pro Phe Asp Ser Ser Asp Ile Val Phe His Tyr
    210                 215                 220

Arg His Ala Gln Phe Tyr Ile Pro Ser Lys Lys Arg Ser His His His
225                 230                 235                 240

His His His

<210> SEQ ID NO 51
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 51
ccatgggatt aaagtatgaa catattgcta agc                              33

<210> SEQ ID NO 52
<211> LENGTH: 40
<212> TYPE: DNA
<213> ORGANISM: Artificial Sequence
<220> FEATURE:
<223> OTHER INFORMATION: Oligonucleotide Primer.

<400> SEQUENCE: 52
gagatctctt tttactagga atataaaact gtgcatgacg                       40
```

-continued

```
<210> SEQ ID NO 53
<211> LENGTH: 855
<212> TYPE: DNA
<213> ORGANISM: Artificial Sequence
<220> FEATURE:
<223> OTHER INFORMATION: Nucleotide sequence of S. aureus coding region
      cloned for expression in E. coli.

<400> SEQUENCE: 53
atgctggcac tttatggatt tgcccaagga cttattcaag aagcaggaat tagaattaaa      60
caattgatgg agcaaaattt aacaattgaa acaaagtcaa atccgaatga ccttgttaca     120
aatgtagata aagcaacaga agatttcatt tttgatacaa ttttagaaac atatcccaat     180
catcaagtat taggtgaaga agggcatggt catgacatcg atacttccaa aggtacggta     240
tggattgttg acccaataga cggtacattg aattttgttc atcaacaaga aaatttcgca     300
atttcaattg gtatttatat cgatggtaaa ccttatgcag gttttgtata tgatgttatg     360
gctgatgtct tatatcatgc taaagtaggg gaaggtgcat atcgtggtag ccaaccctta     420
aaaccattga atgattctaa tctaagacaa agcattattg ggatcaatcc gaactggtta     480
actaaaccaa tttttaggaga atctttaaaa gaaattgtta atgattctag aagtgcaagg     540
gcatatggta gtgcagcgct tgaaatcgtt tcagttgcta caggtaattt agaagcatat     600
atgacgccaa gacttcaacc atgggatttt gctggcggat tggttattt atatgaagta     660 aatggacaag cttccaattt actaggagga ccattaacaa ttagtggtcc aaattcaatc     720
ttagttggaa atcgtggtct ccatcaagaa attagcaatg attatttaga gccccaccat     780
gatgcgttaa tacaattaca tgaacaacga tttaaaagaa aatcaaaaag atctcatcac     840
catcaccatc actaa                                                      855

<210> SEQ ID NO 54
<211> LENGTH: 284
<212> TYPE: PRT
<213> ORGANISM: Artificial Sequence
<220> FEATURE:
<223> OTHER INFORMATION: Amino acid sequence encoded by S. aureus coding
      region cloned for expression in E. coli.

<400> SEQUENCE: 54

Met Leu Ala Leu Tyr Gly Phe Ala Gln Gly Leu Ile Gln Glu Ala Gly
1               5                   10                  15

Ile Arg Ile Lys Gln Leu Met Glu Gln Asn Leu Thr Ile Glu Thr Lys
            20                  25                  30

Ser Asn Pro Asn Asp Leu Val Thr Asn Val Asp Lys Ala Thr Glu Asp
        35                  40                  45

Phe Ile Phe Asp Thr Ile Leu Glu Thr Tyr Pro Asn His Gln Val Leu
    50                  55                  60

Gly Glu Glu Gly His Gly His Asp Ile Asp Thr Ser Lys Gly Thr Val
65                  70                  75                  80

Trp Ile Val Asp Pro Ile Asp Gly Thr Leu Asn Phe Val His Gln Gln
                85                  90                  95

Glu Asn Phe Ala Ile Ser Ile Gly Ile Tyr Ile Asp Gly Lys Pro Tyr
            100                 105                 110

Ala Gly Phe Val Tyr Asp Val Met Ala Asp Val Leu Tyr His Ala Lys
        115                 120                 125

Val Gly Glu Gly Ala Tyr Arg Gly Ser Gln Pro Leu Lys Pro Leu Asn
    130                 135                 140
```

-continued

```
Asp Ser Asn Leu Arg Gln Ser Ile Ile Gly Ile Asn Pro Asn Trp Leu
145                 150                 155                 160

Thr Lys Pro Ile Leu Gly Glu Ile Phe Lys Glu Ile Val Asn Asp Ser
            165                 170                 175

Arg Ser Ala Arg Ala Tyr Gly Ser Ala Ala Leu Glu Ile Val Ser Val
        180                 185                 190

Ala Thr Gly Asn Leu Glu Ala Tyr Met Thr Pro Arg Leu Gln Pro Trp
    195                 200                 205

Asp Phe Ala Gly Gly Leu Val Ile Leu Tyr Glu Val Asn Gly Gln Ala
210                 215                 220

Ser Asn Leu Leu Gly Gly Pro Leu Thr Ile Ser Gly Pro Asn Ser Ile
225                 230                 235                 240

Leu Val Gly Asn Arg Gly Leu His Gln Glu Ile Ser Asn Asp Tyr Leu
                245                 250                 255

Glu Pro His His Asp Ala Leu Ile Gln Leu His Glu Gln Arg Phe Lys
            260                 265                 270

Arg Lys Ser Lys Arg Ser His His His His His
        275                 280
```

<210> SEQ ID NO 55
<211> LENGTH: 31
<212> TYPE: DNA
<213> ORGANISM: Artificial Sequence
<220> FEATURE:
<223> OTHER INFORMATION: Oligonucleotide Primer.

<400> SEQUENCE: 55
gcatgctggc actttatgga tttgcccaag g          31

<210> SEQ ID NO 56
<211> LENGTH: 40
<212> TYPE: DNA
<213> ORGANISM: Artificial Sequence
<220> FEATURE:
<223> OTHER INFORMATION: Oligonucleotide Primer.

<400> SEQUENCE: 56
gagatctttt tgattttctt ttaaatcgtt gttcatgatt          40

<210> SEQ ID NO 57
<211> LENGTH: 567
<212> TYPE: DNA
<213> ORGANISM: Artificial Sequence
<220> FEATURE:
<223> OTHER INFORMATION: Nucleotide sequence of S. aureus coding region
      cloned for expression in E. coli.

<400> SEQUENCE: 57
atgggattca aaacaatttt aacatcaaat ttaacaaata aaatcggtaa ttcagtcttt     60
aaaatagaaa atgttgacgg aaaaggtgca atgccaacga cgattcaaga attgagagaa    120
agacgacaac gtgctgaagc aattgtaaag agaaagtctt taatgtcatc aacaatgagc    180
gttgttccaa ttccgggttt agattttggt gttgatttaa attaatgaa agatattatc     240 gaagatgtta ataaaattta tggtttagat cataagcaag ttaatagcct tggggatgat    300
gtgaaagaaa gaattatgtc tgcagcagca attcaaggta gtcaatttat tggtaaagaa    360
atttcaaatg cattttttaaa aattgtaatt agagatgtag ctaaacgtac tgctgcaaaa    420
caaacaaaat ggtttcctgt tgtaggacaa gctgtgtctg catctattag ttactatttt    480
atgaataaaa ttggaaaaga tcacattcaa aaatgcgaaa atgttattaa aaatgtcatg    540
agatctcatc accatcacca tcactaa       567

<210> SEQ ID NO 58
<211> LENGTH: 188
<212> TYPE: PRT
<213> ORGANISM: Artificial Sequence
<220> FEATURE:
<223> OTHER INFORMATION: Amino acid sequence encoded by S. aureus coding
      region cloned for expression in E. coli.

<400> SEQUENCE: 58

Met Gly Phe Lys Asn Asn Leu Thr Ser Asn Leu Thr Asn Lys Ile Gly
1               5                   10                  15

Asn Ser Val Phe Lys Ile Glu Asn Val Asp Gly Lys Gly Ala Met Pro
            20                  25                  30

Thr Thr Ile Gln Glu Leu Arg Glu Arg Gln Arg Ala Glu Ala Ile
        35                  40                  45

Val Lys Arg Lys Ser Leu Met Ser Ser Thr Met Ser Val Val Pro Ile
    50                  55                  60

Pro Gly Leu Asp Phe Gly Val Asp Leu Lys Leu Met Lys Asp Ile Ile
65                  70                  75                  80

Glu Asp Val Asn Lys Ile Tyr Gly Leu Asp His Lys Gln Val Asn Ser
                85                  90                  95

Leu Gly Asp Asp Val Lys Glu Arg Ile Met Ser Ala Ala Ile Gln
            100                 105                 110

Gly Ser Gln Phe Ile Gly Lys Arg Ile Ser Asn Ala Phe Leu Lys Ile
        115                 120                 125

Val Ile Arg Asp Val Ala Lys Arg Thr Ala Ala Lys Gln Thr Lys Trp
    130                 135                 140

Phe Pro Val Val Gly Gln Ala Val Ser Ala Ser Ile Ser Tyr Tyr Phe
145                 150                 155                 160

Met Asn Lys Ile Gly Lys Asp His Ile Gln Lys Cys Glu Asn Val Ile
                165                 170                 175

Lys Asn Val Met Arg Ser His His His His His His
            180                 185

<210> SEQ ID NO 59
<211> LENGTH: 28
<212> TYPE: DNA
<213> ORGANISM: Artificial Sequence
<220> FEATURE:
<223> OTHER INFORMATION: Oligonucleotide Primer.

<400> SEQUENCE: 59
ccatgggatt caaaaacaat ttaacatc       28

<210> SEQ ID NO 60
<211> LENGTH: 33
<212> TYPE: DNA
<213> ORGANISM: Artificial Sequence
<220> FEATURE:
<223> OTHER INFORMATION: Oligonucleotide Primer.

<400> SEQUENCE: 60
gagatctcat gacatttta ataacatttt cgc       33

<210> SEQ ID NO 61
<211> LENGTH: 1410
<212> TYPE: DNA
<213> ORGANISM: Artificial Sequence

```
<220> FEATURE:
<223> OTHER INFORMATION: Nucleotide sequence of S. aureus coding region
      cloned for expression in E. coli.

<400> SEQUENCE: 61
atgggattca tgggagaata cgatcatcaa ttagatacaa aaggacgtat gattataccg      60
tccaagtttc gttatgactt aaatgagcgt tttattatca caagaggcct tgataaatgt     120
ttattcggtt acactctaga cgaatggcaa cagattgaag agaaaatgaa aaccttacct     180
atgacaaaaa aagacgcacg taagtttatg cgtatgttct tctctggtgc tgttgaagta     240
gaacttgata agcaagggcg tattaacatc cctcaaaact tgaggaaata cgctaattta     300
actaaagaat gtacagtaat cggtgtttca aatcgtattg agatttggga tagagaaact     360
tggaatgatt tctatgaaga atctgaagaa agtttcgaag atattgctga agatttaata     420
gattttsatt ttyaaaatgg aggaattgaa gtgtttcatc atatcagcgt tatgttaaac     480
gaaaccattg attatttaaa tgtaaaagaa atggtgtgt acattgactg tacgctaggt      540
ggagcgggac atgccctta tttactaaat caattaaatg acgacggaag attaatagca      600
atcgatcaag accaaactgc aattgataat gctaaagagg tattaaagga tcatttgcat     660
aaggtgactt tgttcatag caacttccgt gaattaactc aaatattaaa agacttaaac      720
attgaaaaag tagatggaat ttattacgac ttgggtgttt caagcccaca actcgacatt     780
ccagaacgag gattcagtta tcaccatgac gcaacattag acatgcgtat ggaccaaaca     840
caagaactaa cagcatatga aattgttaac aattggtcat atgaagcgtt agtgaagatt     900 tttttatcgct atggcgagga gaaatttttca aaacagatag ctcgaagaat cgaagcacat    960
cgcgaacaac aaccaataac aacaacatta gaattagttg acattataaa agaaggtatt    1020
cctgcaaaag caagaagaaa aggcggacat cctgcaaaac gagtatttca agcactacga    1080
attgcagtaa acgatgaatt gtcagctttt gaagattcaa tagaacaagc gattgaatta    1140
gtgaaagtag atggcaggat ttcggtaatc actttccatt ctttagaaga tcgtttatgt    1200
aaacaggtgt tccaagaata tgaaaaaggt ccagaggtac aagaggatt accagttata    1260 ccagaagcat atacacctaa gttaaagcgt gttaatcgta aaccgattac cgctacagaa    1320
gaagatttag atgacaataa cagagcacga agcgcgaaat tacgtgtagc tgaaatactt    1380
aaaagatctc atcaccatca ccatcactaa                                     1410

<210> SEQ ID NO 62
<211> LENGTH: 469
<212> TYPE: PRT
<213> ORGANISM: Artificial Sequence
<220> FEATURE:
<223> OTHER INFORMATION: Amino acid sequence encoded by S. aureus coding
      region cloned for expression in E. coli.
<221> NAME/KEY: misc_feature
<222> LOCATION: (143)..(143)
<223> OTHER INFORMATION: Corresponding codin encodes either asparagine
      or histidine.

<400> SEQUENCE: 62

Met Gly Phe Met Gly Glu Tyr Asp His Gln Leu Asp Thr Lys Gly Arg
1               5                   10                  15

Met Ile Ile Pro Ser Lys Phe Arg Tyr Asp Leu Asn Glu Arg Phe Ile
            20                  25                  30

Ile Thr Arg Gly Leu Asp Lys Cys Leu Phe Gly Tyr Thr Leu Asp Glu
        35                  40                  45

Trp Gln Gln Ile Glu Glu Lys Met Lys Thr Leu Pro Met Thr Lys Lys
```

```
              50                  55                  60
Asp Ala Arg Lys Phe Met Arg Met Phe Phe Ser Gly Ala Val Glu Val
 65                  70                  75                  80

Glu Leu Asp Lys Gln Gly Arg Ile Asn Ile Pro Gln Asn Leu Arg Lys
                 85                  90                  95

Tyr Ala Asn Leu Thr Lys Glu Cys Thr Val Ile Gly Val Ser Asn Arg
                100                 105                 110

Ile Glu Ile Trp Asp Arg Glu Thr Trp Asn Asp Phe Tyr Glu Glu Ser
            115                 120                 125

Glu Glu Ser Phe Glu Asp Ile Ala Glu Asp Leu Ile Asp Phe Xaa Phe
130                 135                 140

Gln Asn Gly Gly Ile Glu Val Phe His His Ile Ser Val Met Leu Asn
145                 150                 155                 160

Glu Thr Ile Asp Tyr Leu Asn Val Lys Glu Asn Gly Val Tyr Ile Asp
                165                 170                 175

Cys Thr Leu Gly Gly Ala Gly His Ala Leu Tyr Leu Leu Asn Gln Leu
            180                 185                 190

Asn Asp Asp Gly Arg Leu Ile Ala Ile Asp Gln Asp Gln Thr Ala Ile
        195                 200                 205

Asp Asn Ala Lys Glu Val Leu Lys Asp His Leu His Lys Val Thr Phe
210                 215                 220

Val His Ser Asn Phe Arg Glu Leu Thr Gln Ile Leu Lys Asp Leu Asn
225                 230                 235                 240

Ile Glu Lys Val Asp Gly Ile Tyr Tyr Asp Leu Gly Val Ser Ser Pro
                245                 250                 255

Gln Leu Asp Ile Pro Glu Arg Gly Phe Ser Tyr His His Asp Ala Thr
            260                 265                 270

Leu Asp Met Arg Met Asp Gln Thr Gln Glu Leu Thr Ala Tyr Glu Ile
        275                 280                 285

Val Asn Asn Trp Ser Tyr Glu Ala Leu Val Lys Ile Phe Tyr Arg Tyr
290                 295                 300

Gly Glu Glu Lys Phe Ser Lys Gln Ile Ala Arg Arg Ile Glu Ala His
305                 310                 315                 320

Arg Glu Gln Gln Pro Ile Thr Thr Leu Glu Leu Val Asp Ile Ile
                325                 330                 335

Lys Glu Gly Ile Pro Ala Lys Ala Arg Arg Lys Gly His Pro Ala
            340                 345                 350

Lys Arg Val Phe Gln Ala Leu Arg Ile Ala Val Asn Asp Glu Leu Ser
        355                 360                 365

Ala Phe Glu Asp Ser Ile Glu Gln Ala Ile Glu Leu Val Lys Val Asp
370                 375                 380

Gly Arg Ile Ser Val Ile Thr Phe His Ser Leu Glu Asp Arg Leu Cys
385                 390                 395                 400

Lys Gln Val Phe Gln Glu Tyr Glu Lys Gly Pro Glu Val Pro Arg Gly
                405                 410                 415

Leu Pro Val Ile Pro Glu Ala Tyr Thr Pro Lys Leu Lys Arg Val Asn
            420                 425                 430

Arg Lys Pro Ile Thr Ala Thr Glu Glu Asp Leu Asp Asp Asn Asn Arg
        435                 440                 445

Ala Arg Ser Ala Lys Leu Arg Val Ala Glu Ile Leu Lys Arg Ser His
    450                 455                 460

His His His His
465
```

<210> SEQ ID NO 63
<211> LENGTH: 30
<212> TYPE: DNA
<213> ORGANISM: Artificial Sequence
<220> FEATURE:
<223> OTHER INFORMATION: Oligonucleotide Primer.

<400> SEQUENCE: 63
ccatgggatt catgggagaa tacgatcatc                                          30

<210> SEQ ID NO 64
<211> LENGTH: 38
<212> TYPE: DNA
<213> ORGANISM: Artificial Sequence
<220> FEATURE:
<223> OTHER INFORMATION: Oligonucleotide Primer.

<400> SEQUENCE: 64
gagatctttt aagtatttca gctacacgta atttcgcg                                 38

<210> SEQ ID NO 65
<211> LENGTH: 996
<212> TYPE: DNA
<213> ORGANISM: Artificial Sequence
<220> FEATURE:
<223> OTHER INFORMATION: Nucleotide sequence of S. aureus coding region
      cloned for expression in E. coli.

<400> SEQUENCE: 65
atgggaataa taatcatga attactaggt attcaccatg ttactgcaat gacagatgat        60
gcagaacgta attataaatt ttttacagaa gtactaggca tgcgtttagt taaaaagaca      120
gtcaatcaag atgatattta tacgtatcat acttttttg cagatgatgt aggttcggca       180
ggtacagaca tgacgttctt tgattttcca aatattacaa agggcaggc aggaacaaat       240 tccattacaa gaccgtcttt tagagtgcct aacgatgacg cattaacata ttatgaacag      300
cgctttgatg agtttggtgt taaacacgaa ggtattcaag aattatttgg taaaaaagtg      360
ttgccatttg aagaagtcga tggccaagtg tatcaattaa tttcagatga gttaaatgaa      420
ggggtagcac ctggtgtacc ttggaagaat ggaccggttc cagtagataa agcgatttat      480
ggattaggcc ccattgaaat taagtaagt tatttttgacg actttaaaaa tattttagag      540
actgtttacg gtatgacaac tattgcgcat gaagataatg tcgcattact tgaagttggc      600
gaaggaggca atggtggcca ggtaatctta ataaaagatg ataaagggcc agcagcacgt      660
caaggttatg gtgaggtaca tcatgtgtca tttcgtgtga agatcatga tgcaatagaa       720 gcgtgggcaa cgaaatataa agaggtaggt attaataact caggcatcgt taatcgtttc      780
tattttgaag cattatatgc acgtgtgggg catattttaa tagaaatttc aacagatgga      840
ccaggattta tggaagatga accttatgaa acattaggcg aagggttatc cttaccacca      900
tttttagaaa ataaaagaga atatattgaa tcggaagtta gaccttttaa tacgaagcgt      960
caacatggta gatctcatca ccatcaccat cactaa                                996

<210> SEQ ID NO 66
<211> LENGTH: 331
<212> TYPE: PRT
<213> ORGANISM: Artificial Sequence
<220> FEATURE:
<223> OTHER INFORMATION: Amino acid sequence encoded by S. aureus coding
      region cloned for expression in E. coli.

<400> SEQUENCE: 66

```
Met Gly Ile Asn Asn His Glu Leu Leu Gly Ile His Val Thr Ala
1               5                   10                  15
Met Thr Asp Asp Ala Glu Arg Asn Tyr Lys Phe Phe Thr Glu Val Leu
            20                  25                  30
Gly Met Arg Leu Val Lys Lys Thr Val Asn Gln Asp Ile Tyr Thr
            35                  40                  45
Tyr His Thr Phe Phe Ala Asp Asp Val Gly Ser Ala Gly Thr Asp Met
    50                  55                  60
Thr Phe Phe Asp Phe Pro Asn Ile Thr Lys Gly Gln Ala Gly Thr Asn
65                  70                  75                  80
Ser Ile Thr Arg Pro Ser Phe Arg Val Pro Asn Asp Asp Ala Leu Thr
                85                  90                  95
Tyr Tyr Glu Gln Arg Phe Asp Glu Phe Gly Val Lys His Glu Gly Ile
                100                 105                 110
Gln Glu Leu Phe Gly Lys Lys Val Leu Pro Phe Glu Val Asp Gly
            115                 120                 125
Gln Val Tyr Gln Leu Ile Ser Asp Glu Leu Asn Glu Gly Val Ala Pro
            130                 135                 140
Gly Val Pro Trp Lys Asn Gly Pro Val Pro Val Asp Lys Ala Ile Tyr
145                 150                 155                 160
Gly Leu Gly Pro Ile Glu Ile Lys Val Ser Tyr Phe Asp Asp Phe Lys
                165                 170                 175
Asn Ile Leu Glu Thr Val Tyr Gly Met Thr Thr Ile Ala His Glu Asp
            180                 185                 190
Asn Val Ala Leu Leu Glu Val Gly Glu Gly Gly Asn Gly Gly Gln Val
            195                 200                 205
Ile Leu Ile Lys Asp Asp Lys Gly Pro Ala Ala Arg Gln Gly Tyr Gly
            210                 215                 220
Glu Val His His Val Ser Phe Arg Val Lys Asp His Asp Ala Ile Glu
225                 230                 235                 240
Ala Trp Ala Thr Lys Tyr Lys Glu Val Gly Ile Asn Asn Ser Gly Ile
                245                 250                 255
Val Asn Arg Phe Tyr Phe Glu Ala Leu Tyr Ala Arg Val Gly His Ile
                260                 265                 270
Leu Ile Glu Ile Ser Thr Asp Gly Pro Gly Phe Met Glu Asp Glu Pro
            275                 280                 285
Tyr Glu Thr Leu Gly Gly Leu Ser Leu Pro Pro Phe Leu Glu Asn
            290                 295                 300
Lys Arg Glu Tyr Ile Glu Ser Glu Val Arg Pro Phe Asn Thr Lys Arg
305                 310                 315                 320
Gln His Gly Arg Ser His His His His His
                325                 330
```

<210> SEQ ID NO 67
<211> LENGTH: 31
<212> TYPE: DNA
<213> ORGANISM: Artificial Sequence
<220> FEATURE:
<223> OTHER INFORMATION: Oligonucleotide Primer.

<400> SEQUENCE: 67
ccatgggaat aaataatcat gaattactag g          31

<210> SEQ ID NO 68

-continued

```
<211> LENGTH: 36
<212> TYPE: DNA
<213> ORGANISM: Artificial Sequence
<220> FEATURE:
<223> OTHER INFORMATION: Oligonucleotide Primer.

<400> SEQUENCE: 68
gagatctacc atgttgacgc ttcgtattaa aaggtc                            36

<210> SEQ ID NO 69
<211> LENGTH: 996
<212> TYPE: DNA
<213> ORGANISM: Artificial Sequence
<220> FEATURE:
<223> OTHER INFORMATION: Nucleotide sequence of S. aureus coding region
      cloned for expression in E. coli.

<400> SEQUENCE: 69
atgggaataa ataatcatga attactaggt attcaccatg ttactgcaat gacagatgat    60
gcagaacgta attataaatt ttttacagaa gtactaggca tgcgtttagt taaaaagaca   120
gtcaatcaag atgatattta tacgtatcat acttttttg cagatgatgt aggttcggca   180
ggtacagaca tgacgttctt tgattttcca aatattacaa aagggcaggc aggaacaaat   240
tccattacaa gaccgtcttt tagagtgcct aacgatgacg cattaacata ttatgaacag   300
cgctttgatg agtttggtgt taaacacgaa ggtattcaag aattatttgg taaaaaagtg   360
ttgccatttg aagaagtcga tggccaagtg tatcaattaa tttcagatga gttaaatgaa   420
ggggtagcac ctggtgtacc ttggaagaat ggaccggttc cagtagataa agcgatttat   480
ggattaggcc ccattgaaat taagtaagt tattttgacg acttaaaaa tattttagag   540 actgtttacg gtatgacaac tattgcgcat gaagataatg tcgcattact tgaagttggc   600
gaaggaggca atggtggcca ggtaatctta ataaaagatg ataaagggcc agcagcacgt   660
caaggttatg gtgaggtaca tcatgtgtca tttcgtgtga aagatcatga tgcaatagaa   720
gcgtgggcaa cgaaatataa agaggtaggt attaataact caggcatcgt taatcgtttc   780
tattttgaag cattatatgc acgtgtgggg catattttaa tagaaatttc aacagatgga   840
ccaggattta tggaagatga accttatgaa acattaggcg aagggttatc cttaccacca   900 ttttagaaa ataaaagaga atatattgaa tcggaagtta gacctttaa tacgaagcgt   960 caacatggta gatctcatca ccatcaccat cactaa                             996

<210> SEQ ID NO 70
<211> LENGTH: 331
<212> TYPE: PRT
<213> ORGANISM: Artificial Sequence
<220> FEATURE:
<223> OTHER INFORMATION: Amino acid sequence encoded by S. aureus coding
      region cloned for expression in E. coli.

<400> SEQUENCE: 70

Met Gly Ile Asn Asn His Glu Leu Leu Gly Ile His His Val Thr Ala
1               5                   10                  15

Met Thr Asp Asp Ala Glu Arg Asn Tyr Lys Phe Phe Thr Glu Val Leu
            20                  25                  30

Gly Met Arg Leu Val Lys Lys Thr Val Asn Gln Asp Asp Ile Tyr Thr
        35                  40                  45

Tyr His Thr Phe Phe Ala Asp Asp Val Gly Ser Ala Gly Thr Asp Met
    50                  55                  60

Thr Phe Phe Asp Phe Pro Asn Ile Thr Lys Gly Gln Ala Gly Thr Asn
```

```
            65                  70                  75                  80
        Ser Ile Thr Arg Pro Ser Phe Arg Val Pro Asn Asp Asp Ala Leu Thr
                        85                  90                  95

Tyr Tyr Glu Gln Arg Phe Asp Glu Phe Gly Val Lys His Glu Gly Ile
                    100                 105                 110

Gln Glu Leu Phe Gly Lys Lys Val Leu Pro Phe Glu Glu Val Asp Gly
                115                 120                 125

Gln Val Tyr Gln Leu Ile Ser Asp Glu Leu Asn Glu Gly Val Ala Pro
            130                 135                 140

Gly Val Pro Trp Lys Asn Gly Pro Val Pro Val Asp Lys Ala Ile Tyr
        145                 150                 155                 160

Gly Leu Gly Pro Ile Glu Ile Lys Val Ser Tyr Phe Asp Asp Phe Lys
                        165                 170                 175

Asn Ile Leu Glu Thr Val Tyr Gly Met Thr Thr Ile Ala His Glu Asp
                    180                 185                 190

Asn Val Ala Leu Leu Glu Val Gly Glu Gly Asn Gly Gly Gln Val
                195                 200                 205

Ile Leu Ile Lys Asp Asp Lys Gly Pro Ala Ala Arg Gln Gly Tyr Gly
            210                 215                 220

Glu Val His His Val Ser Phe Arg Val Lys Asp His Asp Ala Ile Glu
        225                 230                 235                 240

Ala Trp Ala Thr Lys Tyr Lys Glu Val Gly Ile Asn Asn Ser Gly Ile
                        245                 250                 255

Val Asn Arg Phe Tyr Phe Glu Ala Leu Tyr Ala Arg Val Gly His Ile
                    260                 265                 270

Leu Ile Glu Ile Ser Thr Asp Gly Pro Gly Phe Met Glu Asp Glu Pro
                275                 280                 285

Tyr Glu Thr Leu Gly Glu Gly Leu Ser Leu Pro Pro Phe Leu Glu Asn
            290                 295                 300

Lys Arg Glu Tyr Ile Glu Ser Glu Val Arg Pro Phe Asn Thr Lys Arg
        305                 310                 315                 320

Gln His Gly Arg Ser His His His His His
                        325                 330

<210> SEQ ID NO 71
<211> LENGTH: 31
<212> TYPE: DNA
<213> ORGANISM: Artificial Sequence
<220> FEATURE:
<223> OTHER INFORMATION: Oligonucleotide Primer.

<400> SEQUENCE: 71
ccatgggaat aaataatcat gaattactag g                                      31

<210> SEQ ID NO 72
<211> LENGTH: 34
<212> TYPE: DNA
<213> ORGANISM: Artificial Sequence
<220> FEATURE:
<223> OTHER INFORMATION: Oligonucleotide Primer.

<400> SEQUENCE: 72
gagatctacc atgttgacgc ttcgtattaa aagg                                   34

<210> SEQ ID NO 73
<211> LENGTH: 1113
<212> TYPE: DNA
<213> ORGANISM: Artificial Sequence
```

<220> FEATURE:
<223> OTHER INFORMATION: Nucleotide sequence of S. aureus coding region
     cloned for expression in E. coli.

<400> SEQUENCE: 73

```
atgggacgta tcttaaaaga gtccattatt gtggcatttg cctttgttgg tgttgtcgtt    60
ggtgccggct ttgctactgg tcaagaaatt ttccagtttt cacaagtca tggcgcatat   120
agcatttcag gcattattgt aacaggacta ttgattactt taggtggaat ggttgtcatg   180
catacaggtc atcatctaaa gtccagaaat cattctgatt caattaacta tttcttatac   240
ccctctattg caagagggttt tgatattatt ttaacaatgt ttatgttgtc tttagctatt   300
attatgactg caggtggtgc gtcaaccatt catcaaagtt tcaacttacc gtattggctg   360
agcgcactca tattagtcgc ctttatttta gcaacactgt ttctaaaatt cgatcgttta   420
attgctgtgc ttggcggtgt tacccctttt ttaattgcga ttgtcattat gattgcggtc   480
tactatttca caacaagtca tcttgatttt actgccgcta ataatgatgc tcagattcat   540
aagcagaaat cattatcacc tggatggtgg tttgatgcga ttaactatgc aagcttgcaa   600
attgctgctg ccttcagctt cttatcagtg atgggtagta agttaaata tcgtgactca   660
acgttatacg ggggcttgat tggcggttta atcattacat ttttactcat gatgattaat   720
ctaggtttaa tttctcaatt cgataaaatt aaacacgtag atctacctac attaaaatta   780
gcgacacaaa tgtctccgtc aattggtatt attatgtctg tcattatgat acttgtcatc   840
tacaatactg ttgttggatt aatgtatgca tttgcgtcac gtttcagcgt tccattcagc   900
agacgttact tcatcattat tattacaatg gctgtcatca cttatattag tacatttatc   960
ggtttcattt cattaattgg aaaagtattc cctattatgg gattgttcgg tttcatctta  1020
ctcataccctg tactctataa aggtttaatt aagcgtatta ccggcaaatc tcatatcgat  1080
ggatccagat ctcatcacca tcaccatcac taa                                1113
```

<210> SEQ ID NO 74
<211> LENGTH: 370
<212> TYPE: PRT
<213> ORGANISM: Artificial Sequence
<220> FEATURE:
<223> OTHER INFORMATION: Amino acid sequence encoded by S. aureus coding
     region cloned for expression in E. coli.

<400> SEQUENCE: 74

```
Met Gly Arg Ile Leu Lys Glu Ser Ile Ile Val Ala Phe Ala Phe Val
1               5                   10                  15

Gly Val Val Gly Ala Gly Phe Ala Thr Gly Gln Glu Ile Phe Gln
            20                  25                  30

Phe Phe Thr Ser His Gly Ala Tyr Ser Ile Ser Gly Ile Ile Val Thr
        35                  40                  45

Gly Leu Leu Ile Thr Leu Gly Gly Met Val Val Met His Thr Gly His
    50                  55                  60

His Leu Lys Ser Arg Asn His Ser Asp Ser Ile Asn Tyr Phe Leu Tyr
65                  70                  75                  80

Pro Ser Ile Ala Arg Gly Phe Asp Ile Ile Leu Thr Met Phe Met Leu
                85                  90                  95

Ser Leu Ala Ile Ile Met Thr Ala Gly Gly Ala Ser Thr Ile His Gln
            100                 105                 110

Ser Phe Asn Leu Pro Tyr Trp Leu Ser Ala Leu Ile Leu Val Ala Phe
        115                 120                 125
```

-continued

```
Ile Leu Ala Thr Leu Phe Leu Lys Phe Asp Arg Leu Ile Ala Val Leu
130                 135                 140

Gly Gly Val Thr Pro Phe Leu Ile Ala Ile Val Ile Met Ile Ala Val
145                 150                 155                 160

Tyr Tyr Phe Thr Thr Ser His Leu Asp Phe Thr Ala Ala Asn Asn Asp
                165                 170                 175

Ala Gln Ile His Lys Gln Lys Ser Leu Ser Pro Gly Trp Trp Phe Asp
                180                 185                 190

Ala Ile Asn Tyr Ala Ser Leu Gln Ile Ala Ala Phe Ser Phe Leu
                195                 200                 205

Ser Val Met Gly Ser Lys Val Lys Tyr Arg Asp Ser Thr Leu Tyr Gly
210                 215                 220

Gly Leu Ile Gly Gly Leu Ile Ile Thr Phe Leu Leu Met Met Ile Asn
225                 230                 235                 240

Leu Gly Leu Ile Ser Gln Phe Asp Lys Ile Lys His Val Asp Leu Pro
                245                 250                 255

Thr Leu Lys Leu Ala Thr Gln Met Ser Pro Ser Ile Gly Ile Ile Met
                260                 265                 270

Ser Val Ile Met Ile Leu Val Ile Tyr Asn Thr Val Val Gly Leu Met
                275                 280                 285

Tyr Ala Phe Ala Ser Arg Phe Ser Val Pro Phe Ser Arg Arg Tyr Phe
290                 295                 300

Ile Ile Ile Ile Thr Met Ala Val Ile Thr Tyr Ile Ser Thr Phe Ile
305                 310                 315                 320

Gly Phe Ile Ser Leu Ile Gly Lys Val Phe Pro Ile Met Gly Leu Phe
                325                 330                 335

Gly Phe Ile Leu Leu Ile Pro Val Leu Tyr Lys Gly Leu Ile Lys Arg
                340                 345                 350

Ile Thr Gly Lys Ser His Ile Asp Gly Phe Arg Ser His His His His
                355                 360                 365

His His
    370
```

<210> SEQ ID NO 75
<211> LENGTH: 36
<212> TYPE: DNA
<213> ORGANISM: Artificial Sequence
<220> FEATURE:
<223> OTHER INFORMATION: Oligonucleotide Primer.

<400> SEQUENCE: 75
ccatgggacg tatcttaaaa gagtccatta ttgtgg         36

<210> SEQ ID NO 76
<211> LENGTH: 34
<212> TYPE: DNA
<213> ORGANISM: Artificial Sequence
<220> FEATURE:
<223> OTHER INFORMATION: Oligonucleotide Primer.

<400> SEQUENCE: 76
ggatccatcg atatgagatt tgccggtaat acgc         34

<210> SEQ ID NO 77
<211> LENGTH: 801
<212> TYPE: DNA
<213> ORGANISM: Artificial Sequence
<220> FEATURE:
<223> OTHER INFORMATION: Nucleotide sequence of S. aureus coding region -continued cloned for expression in E. coli.

<400> SEQUENCE: 77

| atgggattaa | tcgatacaca | tgtccattta | aatgatgagc | aatacgatga | tgatttgagt | 60 |
| gaagtgatta | cacgtgctag | agaagcaggt | gttgatcgta | tgtttgtagt | tggttttaac | 120 |
| aaatcgacaa | ttgaacgcgc | gatgaaatta | atcgatgagt | atgatttttt | atatggcatt | 180 |
| atcggttggc | atccagttga | cgcaattgat | tttacagaag | aacacttgga | atggattgaa | 240 |
| tctttagctc | agcatccaaa | agtgattggt | attggtgaaa | tgggattaga | ttatcactgg | 300 |
| gataaatctc | ctgcagatgt | tcaaaaggaa | gtttttagaa | agcaaattgc | tttagctaag | 360 |
| cgtttgaagt | taccaattat | cattcataac | cgtgaagcaa | ctcaagactg | tatcgatatc | 420 |
| ttattggagg | agcatgctga | agaggtaggc | gggattatgc | atagctttag | tggttctcca | 480 |
| gaaattgcag | atattgtaac | taataagctg | aattttata | tttcattagg | tggacctgtg | 540 |
| acatttaaaa | atgctaaaca | gcctaaagaa | gttgctaagc | atgtgtcaat | ggagcgtttg | 600 |
| ctagttgaaa | ccgatgcacc | gtatctttcg | ccacatccgt | atagagggaa | gcgaaatgaa | 660 |
| ccggcgagag | taactttagt | agctgaacaa | attgctgaat | taaaaggctt | atcttatgaa | 720 |
| gaagtgtgcg | aacaaacaac | taaaaatgca | gagaaattgt | ttaatttaaa | ttcaagatct | 780 |
| catcaccatc | accatcacta | a | | | | 801 |

<210> SEQ ID NO 78
<211> LENGTH: 266
<212> TYPE: PRT
<213> ORGANISM: Artificial Sequence
<220> FEATURE:
<223> OTHER INFORMATION: Amino acid sequence encoded by S. aureus coding region cloned for expression in E. coli.

<400> SEQUENCE: 78

Met Gly Leu Ile Asp Thr His Val His Leu Asn Asp Glu Gln Tyr Asp
1               5                   10                  15

Asp Asp Leu Ser Glu Val Ile Thr Arg Ala Arg Glu Ala Gly Val Asp
            20                  25                  30

Arg Met Phe Val Val Gly Phe Asn Lys Ser Thr Ile Glu Arg Ala Met
        35                  40                  45

Lys Leu Ile Asp Glu Tyr Asp Phe Leu Tyr Gly Ile Ile Gly Trp His
    50                  55                  60

Pro Val Asp Ala Ile Asp Phe Thr Glu Glu His Leu Glu Trp Ile Glu
65                  70                  75                  80

Ser Leu Ala Gln His Pro Lys Val Ile Gly Ile Gly Glu Met Gly Leu
                85                  90                  95

Asp Tyr His Trp Asp Lys Ser Pro Ala Asp Val Gln Lys Glu Val Phe
            100                 105                 110

Arg Lys Gln Ile Ala Leu Ala Lys Arg Leu Lys Leu Pro Ile Ile Ile
        115                 120                 125

His Asn Arg Glu Ala Thr Gln Asp Cys Ile Asp Ile Leu Leu Glu Glu
    130                 135                 140

His Ala Glu Glu Val Gly Gly Ile Met His Ser Phe Ser Gly Ser Pro
145                 150                 155                 160

Glu Ile Ala Asp Ile Val Thr Asn Lys Leu Asn Phe Tyr Ile Ser Leu
                165                 170                 175

Gly Gly Pro Val Thr Phe Lys Asn Ala Lys Gln Pro Lys Glu Val Ala
            180                 185                 190

```
Lys His Val Ser Met Glu Arg Leu Leu Val Glu Thr Asp Ala Pro Tyr
        195                 200                 205

Leu Ser Pro His Pro Tyr Arg Gly Lys Arg Asn Glu Pro Ala Arg Val
        210                 215                 220

Thr Leu Val Ala Glu Gln Ile Ala Glu Leu Lys Gly Leu Ser Tyr Glu
225                 230                 235                 240

Glu Val Cys Glu Gln Thr Thr Lys Asn Ala Glu Lys Leu Phe Asn Leu
                245                 250                 255

Asn Ser Arg Ser His His His His His His
            260                 265

<210> SEQ ID NO 79
<211> LENGTH: 29
<212> TYPE: DNA
<213> ORGANISM: Artificial Sequence
<220> FEATURE:
<223> OTHER INFORMATION: Oligonucleotide Primer.

<400> SEQUENCE: 79
ccatgggatt aatcgataca catgtccat                                    29

<210> SEQ ID NO 80
<211> LENGTH: 45
<212> TYPE: DNA
<213> ORGANISM: Artificial Sequence
<220> FEATURE:
<223> OTHER INFORMATION: Oligonucleotide Primer.

<400> SEQUENCE: 80
gagatcttga atttaaatta aacaatttct ctgcattttt agttg                  45

<210> SEQ ID NO 81
<211> LENGTH: 2150
<212> TYPE: DNA
<213> ORGANISM: Artificial Sequence
<220> FEATURE:
<223> OTHER INFORMATION: Nucleotide sequence of S. aureus coding region
      cloned for expression in E. coli.

<400> SEQUENCE: 81
atgggaataa tatattggtg tatgacagtt aatggaggga acgaaatgaa agctttatta    60
cttaaaacaa gtgtatggct cgttttgctt tttagtgtaa tgggattatg caagtctcg    120 aacgcggctg agcagcatac accaatgaaa gcacatgcag taacaacgat agacaaagca   180
acaacagata agcaacaagt accgccaaca aaggaagcgg ctcatcattc tggcaaagaa   240
gcggcaacca acgtatcagc atcagcgcag ggaacagctg atgatacaaa cagcaaagta   300
acatccaacg caccatctaa caaaccatct acagtagttt caacaaaagt aaacgaaaca   360
cgcgacgtag atacacaaca agcctcaaca caaaaaccaa ctcacacagc aacgttcaaa   420
ttatcaaatg ctaaaacagc atcactttca ccacgaatgt tgctgctaa tgcaccacaa   480 acaacaacac ataaaatatt acatacaaat gatatccatg ccgactagc cgaagaaaa    540 gggcgtgtca tcggtatggc taaattaaaa acagtaaaag aacaagaaaa gcctgattta   600
atgttagacg caggagacgc cttccaaggt ttaccacttt caaaccagtc taaaggtgaa   660
gaaatggcta agcaatgaa tgcagtaggt tatgatgcta tggcagtcgg taaccatgaa   720
tttgactttg gatacgatca gttgaaaaag ttagagggta tgttagactt cccgatgcta   780
agtactaacg tttataaaga tggaaaacgc gcgtttaagc cttcaacgat tgtaacaaaa   840
aatggtattc gttatggaat tattggtgta acgacaccag aaacaaagac gaaaacaaga   900
```

```
cctgaaggca ttaaaggcgt tgaatttaga gatccattac aaagtgtgac agcggaaatg      960
atgcgtattt ataaagacgt agatacattt gttgttatat cacatttagg aattgatcct     1020
tcaacacaag aaacatggcg tggtgattac ttagtgaaac aattaagtca aaatccacaa     1080
ttgaagaaac gtattacagt tatttgatggt cattcacata cagtacttca aatggtcaa     1140 atttataaca atgatgcatt ggcacaaaca ggtacagcac ttgcgaatat cggtaagatt     1200
acatttaatt atcgcaatgg agaggtatcg aatattaaac cgtcattgat taatgttaaa     1260
gacgttgaaa atgtaacacc gaacaaagca ttagctgaac aaattaatca agctgatcaa     1320
acatttagag cacaaactgc agaggtaatt attccaaaca ataccattga tttcaaagga     1380
gaaagagatg acgttagaac gcgtgaaaca aatttaggaa acgcgattgc agatgctatg     1440
gaagcgtatg gcgttaagaa tttctctaaa aagactgact ttgccgtgac aaatggtgga     1500
ggtattcgtg cctctatcgc aaaaggtaag gtgacacgct atgatttaat ctcagtatta     1560
ccatttggaa atacgattgc gcaaattgat gtaaaaggtt cagacgtctg gacggctttc     1620
gaacatagtt taggcgcacc aacaacacaa aaggacggta agacagtgtt aacagcgaat     1680
ggcggtttac tacatatctc tgattcaatc cgtgtttact atgatataaa taaaccgtct     1740
ggcaaacgaa ttaatgctat tcaaatttta aataaagaga caggtaagtt tgaaaatatt     1800
gatttaaaac gtgtatatca cgtaacgatg aatgacttca cagcatcagg tgggacggat     1860
atagtatgtt cggtggtcct agagaagaag gtatttcatt agatcaagta ctagcaagtt     1920
atttaaaaac agctaactta gctaagtatg atacgacaga accacaacgt atgttattag     1980
gtaaaccagc agtaagtgaa caaccagcta aaggacaaca aggtagcaaa ggtagtaagt     2040
ctggtaaaga tacacaacca attggtgacg acaaagtgat ggatccagcg aaaaaaccag     2100
ctccaggtaa agttgtattg ttgagatctc atcaccatca ccatcactaa               2150
```

<210> SEQ ID NO 82
<211> LENGTH: 716
<212> TYPE: PRT
<213> ORGANISM: Artificial Sequence
<220> FEATURE:
<223> OTHER INFORMATION: Amino acid sequence encoded by S. aureus coding
       region cloned for expression in E. coli.

<400> SEQUENCE: 82

```
Met Gly Ile Ile Tyr Trp Cys Met Thr Val Asn Gly Gly Asn Glu Met
1               5                   10                  15

Lys Ala Leu Leu Leu Lys Thr Ser Val Trp Leu Val Leu Leu Phe Ser
                20                  25                  30

Val Met Gly Leu Trp Gln Val Ser Asn Ala Ala Glu Gln His Thr Pro
            35                  40                  45

Met Lys Ala His Ala Val Thr Thr Ile Asp Lys Ala Thr Thr Asp Lys
        50                  55                  60

Gln Gln Val Pro Pro Thr Lys Glu Ala Ala His His Ser Gly Lys Glu
65                  70                  75                  80

Ala Ala Thr Asn Val Ser Ala Ser Ala Gln Gly Thr Ala Asp Asp Thr
                85                  90                  95

Asn Ser Lys Val Thr Ser Asn Ala Pro Ser Asn Lys Pro Ser Thr Val
            100                 105                 110

Val Ser Thr Lys Val Asn Glu Thr Arg Asp Val Asp Thr Gln Gln Ala
        115                 120                 125

Ser Thr Gln Lys Pro Thr His Thr Ala Thr Phe Lys Leu Ser Asn Ala
```

```
            130                 135                 140
Lys Thr Ala Ser Leu Ser Pro Arg Met Phe Ala Ala Asn Ala Pro Gln
145                 150                 155                 160

Thr Thr Thr His Lys Ile Leu His Thr Asn Asp Ile His Gly Arg Leu
                165                 170                 175

Ala Glu Glu Lys Gly Arg Val Ile Gly Met Ala Lys Leu Lys Thr Val
                180                 185                 190

Lys Glu Gln Glu Lys Pro Asp Leu Met Leu Asp Ala Gly Asp Ala Phe
            195                 200                 205

Gln Gly Leu Pro Leu Ser Asn Gln Ser Lys Gly Glu Glu Met Ala Lys
210                 215                 220

Ala Met Asn Ala Val Gly Tyr Asp Ala Met Ala Val Gly Asn His Glu
225                 230                 235                 240

Phe Asp Phe Gly Tyr Asp Gln Leu Lys Lys Leu Glu Gly Met Leu Asp
                245                 250                 255

Phe Pro Met Leu Ser Thr Asn Val Tyr Lys Asp Gly Lys Arg Ala Phe
                260                 265                 270

Lys Pro Ser Thr Ile Val Thr Lys Asn Gly Ile Arg Tyr Gly Ile Ile
            275                 280                 285

Gly Val Thr Thr Pro Glu Thr Lys Thr Lys Thr Arg Pro Glu Gly Ile
290                 295                 300

Lys Gly Val Glu Phe Arg Asp Pro Leu Gln Ser Val Thr Ala Glu Met
305                 310                 315                 320

Met Arg Ile Tyr Lys Asp Val Asp Thr Phe Val Val Ile Ser His Leu
                325                 330                 335

Gly Ile Asp Pro Ser Thr Gln Glu Thr Trp Arg Gly Asp Tyr Leu Val
                340                 345                 350

Lys Gln Leu Ser Gln Asn Pro Gln Leu Lys Lys Arg Ile Thr Val Ile
            355                 360                 365

Asp Gly His Ser His Thr Val Leu Gln Asn Gly Gln Ile Tyr Asn Asn
            370                 375                 380

Asp Ala Leu Ala Gln Thr Gly Thr Ala Leu Ala Asn Ile Gly Lys Ile
385                 390                 395                 400

Thr Phe Asn Tyr Arg Asn Gly Glu Val Ser Asn Ile Lys Pro Ser Leu
                405                 410                 415

Ile Asn Val Lys Asp Val Glu Asn Val Thr Pro Asn Lys Ala Leu Ala
                420                 425                 430

Glu Gln Ile Asn Gln Ala Asp Gln Thr Phe Arg Ala Gln Thr Ala Glu
            435                 440                 445

Val Ile Ile Pro Asn Asn Thr Ile Asp Phe Lys Gly Glu Arg Asp Asp
450                 455                 460

Val Arg Thr Arg Glu Thr Asn Leu Gly Asn Ala Ile Ala Asp Ala Met
465                 470                 475                 480

Glu Ala Tyr Gly Val Lys Asn Phe Ser Lys Lys Thr Asp Phe Ala Val
                485                 490                 495

Thr Asn Gly Gly Gly Ile Arg Ala Ser Ile Ala Lys Gly Lys Val Thr
                500                 505                 510

Arg Tyr Asp Leu Ile Ser Val Leu Pro Phe Gly Asn Thr Ile Ala Gln
            515                 520                 525

Ile Asp Val Lys Gly Ser Asp Val Trp Thr Ala Phe Glu His Ser Leu
            530                 535                 540

Gly Ala Pro Thr Thr Gln Lys Asp Gly Lys Thr Val Leu Thr Ala Asn
545                 550                 555                 560
```

```
Gly Gly Leu Leu His Ile Ser Asp Ser Ile Arg Val Tyr Tyr Asp Ile
              565                 570                 575

Asn Lys Pro Ser Gly Lys Arg Ile Asn Ala Ile Gln Ile Leu Asn Lys
            580                 585                 590

Glu Thr Gly Lys Phe Glu Asn Ile Asp Leu Lys Arg Val Tyr His Val
        595                 600                 605

Thr Met Asn Asp Phe Thr Ala Ser Gly Asp Gly Tyr Ser Met Phe
    610                 615                 620

Gly Gly Pro Arg Glu Glu Gly Ile Ser Leu Asp Gln Val Leu Ala Ser
625                 630                 635                 640

Tyr Leu Lys Thr Ala Asn Leu Ala Lys Tyr Asp Thr Thr Glu Pro Gln
                645                 650                 655

Arg Met Leu Leu Gly Lys Pro Ala Val Ser Glu Gln Pro Ala Lys Gly
            660                 665                 670

Gln Gln Gly Ser Lys Gly Ser Lys Ser Gly Lys Asp Thr Gln Pro Ile
        675                 680                 685

Gly Asp Asp Lys Val Met Asp Pro Ala Lys Lys Pro Ala Pro Gly Lys
    690                 695                 700

Val Val Leu Leu Arg Ser His His His His His
705                 710                 715
```

```
<210> SEQ ID NO 83
<211> LENGTH: 30
<212> TYPE: DNA
<213> ORGANISM: Artificial Sequence
<220> FEATURE:
<223> OTHER INFORMATION: Oligonucleotide Primer.

<400> SEQUENCE: 83
ccatgggaat aatatattgg tgtatgacag                                    30

<210> SEQ ID NO 84
<211> LENGTH: 34
<212> TYPE: DNA
<213> ORGANISM: Artificial Sequence
<220> FEATURE:
<223> OTHER INFORMATION: Oligonucleotide Primer.

<400> SEQUENCE: 84
gagatctcaa caatacaact ttacctggag ctgg                               34

<210> SEQ ID NO 85
<211> LENGTH: 936
<212> TYPE: DNA
<213> ORGANISM: Artificial Sequence
<220> FEATURE:
<223> OTHER INFORMATION: Nucleotide sequence of S. aureus coding region
      cloned for expression in E. coli.

<400> SEQUENCE: 85
atggataata atgaaaaaga aaaagtaaa agtgaactat tagttgtaac aggtttatct     60
ggcgcaggta atctttggt tattcaatgt ttagaagaca tgggatattt ttgtgtagat    120
aatctaccac cagtgttatt gcctaaattt gtagagttga tggaacaagg aaatccatcc   180
ttaagaaaag tggcaattgc aattgattta agaggtaagg aactatttaa ttcattagtt   240
gcagtagtgg ataaagtcaa aagtgaaagt gacgtcatca ttgatgttat gttttagaa    300 gcaagtactg aaaaattaat ttcaagatat aaggaaacgc gtcgtgcaca tcctttgatg   360
gaacaaggta aagatcgtt aatcaatgca attaatgatg agcgagagca tttgtctcaa   420
```

```
attagaagta tagctaattt tgttatagat actacaaagt tatcacctaa agaattaaaa    480
gaacgcattc gtcgatacta tgaagatgaa gagtttgaaa cttttacaat taatgtcaca    540
agtttcggtt ttaaacatgg gattcagatg gatgcagatt tagtatttga tgtacgattt    600
ttaccaaatc catattatgt agtagattta agacctttaa caggattaga taaagacgtt    660
tataattatg ttatgaaatg gaaagagacg gagattttct ttgaaaaatt aactgatttg    720
ttagatttta tgatacccgg gtataaaaaa gaagggaaat ctcaattagt aattgccatc    780
ggttgtacgg gtggacaaca tcgatctgta gcattagcag aacgactagg taattatcta    840
aatgaagtat ttgaatataa tgtttatgtg catcataggg acgcacatat tgaaagtggc    900
gagaaaaaaa gatctcatca ccatcaccat cactaa                              936
```

<210> SEQ ID NO 86
<211> LENGTH: 311
<212> TYPE: PRT
<213> ORGANISM: Artificial Sequence
<220> FEATURE:
<223> OTHER INFORMATION: Amino acid sequence encoded by S. aureus coding region cloned for expression in E. coli.

<400> SEQUENCE: 86

```
Met Asp Asn Asn Glu Lys Glu Lys Ser Lys Ser Glu Leu Leu Val Val
1               5                   10                  15

Thr Gly Leu Ser Gly Ala Gly Lys Ser Leu Val Ile Gln Cys Leu Glu
            20                  25                  30

Asp Met Gly Tyr Phe Cys Val Asp Asn Leu Pro Pro Val Leu Leu Pro
        35                  40                  45

Lys Phe Val Glu Leu Met Glu Gln Gly Asn Pro Ser Leu Arg Lys Val
    50                  55                  60

Ala Ile Ala Ile Asp Leu Arg Gly Lys Glu Leu Phe Asn Ser Leu Val
65                  70                  75                  80

Ala Val Val Asp Lys Val Lys Ser Glu Ser Asp Val Ile Ile Asp Val
                85                  90                  95

Met Phe Leu Glu Ala Ser Thr Glu Lys Leu Ile Ser Arg Tyr Lys Glu
            100                 105                 110

Thr Arg Arg Ala His Pro Leu Met Glu Gln Gly Lys Arg Ser Leu Ile
        115                 120                 125

Asn Ala Ile Asn Asp Glu Arg Glu His Leu Ser Gln Ile Arg Ser Ile
    130                 135                 140

Ala Asn Phe Val Ile Asp Thr Thr Lys Leu Ser Pro Lys Glu Leu Lys
145                 150                 155                 160

Glu Arg Ile Arg Arg Tyr Tyr Glu Asp Glu Glu Phe Glu Thr Phe Thr
                165                 170                 175

Ile Asn Val Thr Ser Phe Gly Phe Lys His Gly Ile Gln Met Asp Ala
            180                 185                 190

Asp Leu Val Phe Asp Val Arg Phe Leu Pro Asn Pro Tyr Tyr Val Val
        195                 200                 205

Asp Leu Arg Pro Leu Thr Gly Leu Asp Lys Asp Val Tyr Asn Tyr Val
    210                 215                 220

Met Lys Trp Lys Glu Thr Glu Ile Phe Phe Glu Lys Leu Thr Asp Leu
225                 230                 235                 240

Leu Asp Phe Met Ile Pro Gly Tyr Lys Lys Glu Gly Lys Ser Gln Leu
                245                 250                 255

Val Ile Ala Ile Gly Cys Thr Gly Gly Gln His Arg Ser Val Ala Leu
```

-continued

```
                  260                 265                 270
Ala Glu Arg Leu Gly Asn Tyr Leu Asn Glu Val Phe Glu Tyr Asn Val
        275                 280                 285

Tyr Val His His Arg Asp Ala His Ile Glu Ser Gly Glu Lys Lys Arg
        290                 295                 300

Ser His His His His His
305                 310

<210> SEQ ID NO 87
<211> LENGTH: 39
<212> TYPE: DNA
<213> ORGANISM: Artificial Sequence
<220> FEATURE:
<223> OTHER INFORMATION: Oligonucleotide Primer.

<400> SEQUENCE: 87
ccatggataa taatgaaaaa gaaaaaagta aaagtgaac                         39

<210> SEQ ID NO 88
<211> LENGTH: 39
<212> TYPE: DNA
<213> ORGANISM: Artificial Sequence
<220> FEATURE:
<223> OTHER INFORMATION: Oligonucleotide Primer.

<400> SEQUENCE: 88
gagatctttt tttctcgcca ctttcaatat gtgcgtccc                         39

<210> SEQ ID NO 89
<211> LENGTH: 1509
<212> TYPE: DNA
<213> ORGANISM: Artificial Sequence
<220> FEATURE:
<223> OTHER INFORMATION: Nucleotide sequence of S. aureus coding region
      cloned for expression in E. coli.

<400> SEQUENCE: 89
atgggacgat tacatttttc aaacgattta ggaacgttat ttactattat tttagccatt     60
ggattcatca ttaatttagt attggctttt attattatct ttttagaaag aaataggcgt    120
acagcgagtt caactgggc atggctattt gtacttttg tcttaccatt gattggtttt     180
attctttact tgttttttgg tagaaccgtt tcggcacgca aattgaataa aaacaatggt    240
aacgtgttaa cggatttcga tggacttttta aaacaacaaa tagaaagctt tgataaaggt    300
aattatggta ctgataacaa acaagttcaa aaacatcatg atttagtacg tatgctttttg    360 atggatcaag atggttttttt aactgaaaat aataaagttg atcatttcat tgatggaaat    420
gatttatatg atcaagtttt aaaagatatt aaaaatgcaa agaatatat ccatttagag    480 tactatactt tcgctttaga tggtttaggt aaaagaattt tacatgcttt agaagaaaaa    540
ttgaaacaag gtctagaagt aaaaatatta tatgatgatg ttggatctaa aaatgttaag    600
atggcaaatt ttgatcattt taaatcgtta ggtggagaag ttgaagcatt ttttgcttca    660
aaattaccgt tattgaattt cagaatgaat aatagaaatc atagaaaaat catcgtaatc    720
gatggtcaac taggttatgt cggaggattt aacattggtg atgaatatct aggattagga    780
aaattaggat attggagaga tacgcatttt acgtatacaag gggatgcggt tgatgcactg    840
cagttgcgat ttatttttaga ctggaattcg caagcgcacc gtccacaatt tgaatatgat    900
gttaagtatt tccctaaaaa gaacggacca ttgggcaatt caccaattca aatagctgca    960
agtggcccgg ctagtgactg gcatcaaatt gaatacggtt atacaaaaat gattatgagt   1020
```

-continued

```
gcaaagaaat ctgtatattt acaatcacca tatttcattc cggataattc atatataaat    1080
gccattaaaa ttgctgctaa atcaggtgta gatgtacatt taatgattcc atgtaagcca    1140
gatcatccat tagtatattg ggcgacattt tcaaatgcct ctgacttatt atcaagtggt    1200
gttaaaattt atacgtatga aaatggattt atacattcta aaatgtgctt aattgatgat    1260
gaaatcgtat cagtgggcac agcaaatatg gactttagaa gttttgaatt aaattttgaa    1320
gtaaatgcct ttgtatatga tgaaaatctt gctaaagatt taagggtggc ttatgaacat    1380
gatattacaa aatcaaaaca actaaccaaa gaatcatatg ccaatagacc gctgtctgtt    1440
aaattcaaag aatcgttagc aaaattagtt tcgccaattt taagatctca tcaccatcac    1500
catcactaa                                                            1509
```

<210> SEQ ID NO 90
<211> LENGTH: 502
<212> TYPE: PRT
<213> ORGANISM: Artificial Sequence
<220> FEATURE:
<223> OTHER INFORMATION: Amino acid sequence encoded by S. aureus coding
      region cloned for expression in E. coli.

<400> SEQUENCE: 90

```
Met Gly Arg Phe Thr Phe Ser Asn Asp Leu Gly Thr Leu Phe Thr Ile
1               5                   10                  15

Ile Leu Ala Ile Gly Phe Ile Ile Asn Leu Val Leu Ala Phe Ile Ile
                20                  25                  30

Ile Phe Leu Glu Arg Asn Arg Arg Thr Ala Ser Ser Thr Trp Ala Trp
            35                  40                  45

Leu Phe Val Leu Phe Val Leu Pro Leu Ile Gly Phe Ile Leu Tyr Leu
    50                  55                  60

Phe Phe Gly Arg Thr Val Ser Ala Arg Lys Leu Asn Lys Asn Asn Gly
65                  70                  75                  80

Asn Val Leu Thr Asp Phe Asp Gly Leu Leu Lys Gln Gln Ile Glu Ser
                85                  90                  95

Phe Asp Lys Gly Asn Tyr Gly Thr Asp Asn Lys Gln Val Gln Lys His
            100                 105                 110

His Asp Leu Val Arg Met Leu Leu Met Asp Gln Asp Gly Phe Leu Thr
        115                 120                 125

Glu Asn Asn Lys Val Asp His Phe Ile Asp Gly Asn Asp Leu Tyr Asp
    130                 135                 140

Gln Val Leu Lys Asp Ile Lys Asn Ala Lys Glu Tyr Ile His Leu Glu
145                 150                 155                 160

Tyr Tyr Thr Phe Ala Leu Asp Gly Leu Gly Lys Arg Ile Leu His Ala
                165                 170                 175

Leu Glu Glu Lys Leu Lys Gln Gly Leu Glu Val Lys Ile Leu Tyr Asp
            180                 185                 190

Asp Val Gly Ser Lys Asn Val Lys Met Ala Asn Phe Asp His Phe Lys
        195                 200                 205

Ser Leu Gly Gly Glu Val Glu Ala Phe Ala Ser Lys Leu Pro Leu
    210                 215                 220

Leu Asn Phe Arg Met Asn Asn Arg Asn His Arg Lys Ile Ile Val Ile
225                 230                 235                 240

Asp Gly Gln Leu Gly Tyr Val Gly Gly Phe Asn Ile Gly Asp Glu Tyr
                245                 250                 255

Leu Gly Leu Gly Lys Leu Gly Tyr Trp Arg Asp Thr His Leu Arg Ile
```

```
                260                 265                 270
Gln Gly Asp Ala Val Asp Ala Leu Gln Leu Arg Phe Ile Leu Asp Trp
            275                 280                 285

Asn Ser Gln Ala His Arg Pro Gln Phe Glu Tyr Asp Val Lys Tyr Phe
        290                 295                 300

Pro Lys Lys Asn Gly Pro Leu Gly Asn Ser Pro Ile Gln Ile Ala Ala
305                 310                 315                 320

Ser Gly Pro Ala Ser Asp Trp His Gln Ile Glu Tyr Gly Tyr Thr Lys
                325                 330                 335

Met Ile Met Ser Ala Lys Lys Ser Val Tyr Leu Gln Ser Pro Tyr Phe
            340                 345                 350

Ile Pro Asp Asn Ser Tyr Ile Asn Ala Ile Lys Ile Ala Ala Lys Ser
        355                 360                 365

Gly Val Asp Val His Leu Met Ile Pro Cys Lys Pro Asp His Pro Leu
    370                 375                 380

Val Tyr Trp Ala Thr Phe Ser Asn Ala Ser Asp Leu Leu Ser Ser Gly
385                 390                 395                 400

Val Lys Ile Tyr Thr Tyr Glu Asn Gly Phe Ile His Ser Lys Met Cys
                405                 410                 415

Leu Ile Asp Asp Glu Ile Val Ser Val Gly Thr Ala Asn Met Asp Phe
            420                 425                 430

Arg Ser Phe Glu Leu Asn Phe Glu Val Asn Ala Phe Val Tyr Asp Glu
        435                 440                 445

Asn Leu Ala Lys Asp Leu Arg Val Ala Tyr Glu His Asp Ile Thr Lys
    450                 455                 460

Ser Lys Gln Leu Thr Lys Glu Ser Tyr Ala Asn Arg Pro Leu Ser Val
465                 470                 475                 480

Lys Phe Lys Glu Ser Leu Ala Lys Leu Val Ser Pro Ile Leu Arg Ser
                485                 490                 495

His His His His His His
            500

<210> SEQ ID NO 91
<211> LENGTH: 34
<212> TYPE: DNA
<213> ORGANISM: Artificial Sequence
<220> FEATURE:
<223> OTHER INFORMATION: Oligonucleotide Primer.

<400> SEQUENCE: 91
ccatgggacg atttacattt tcaaacgatt tagg                              34

<210> SEQ ID NO 92
<211> LENGTH: 36
<212> TYPE: DNA
<213> ORGANISM: Artificial Sequence
<220> FEATURE:
<223> OTHER INFORMATION: Oligonucleotide Primer.

<400> SEQUENCE: 92
gagatcttaa aattggcgaa actaattttg ctaacg                            36

<210> SEQ ID NO 93
<211> LENGTH: 447
<212> TYPE: DNA
<213> ORGANISM: Artificial Sequence
<220> FEATURE:
<223> OTHER INFORMATION: Nucleotide sequence of S. aureus coding region
      cloned for expression in E. coli.
```

-continued

<400> SEQUENCE: 93

```
atgggaaaga ttttattcgt tgtacaggt aacacatgtc gtagcccatt agcggaaagt      60
attgcaaaag aggttatgcc aaatcatcaa tttgaatcaa gaggtatatt cgctgtgaac    120
aatcaaggtg tttcgaatta tgttgaagac ttagttgaag aacatcattt agctgaaacg    180
accttatcgc aacaatttac tgaagcagat ttgaaagcag atattatttt gacgatgtcg    240
tattcgcaca agaattaat agaggcacac tttggtttgc aaaatcatgt tttcacattg     300
catgaatatg taaagaagc aggagaagtt atagatccat acggtggaac aaaagaaatg     360
tatgtacata cctatgaaga acttgtaagt ttaatttaa aattaaaaga tattatttgc     420
agatctcatc accatcacca tcactaa                                        447
```

<210> SEQ ID NO 94
<211> LENGTH: 148
<212> TYPE: PRT
<213> ORGANISM: Artificial Sequence
<220> FEATURE:
<223> OTHER INFORMATION: Amino acid sequence encoded by S. aureus coding
    region cloned for expression in E. coli.

<400> SEQUENCE: 94

```
Met Gly Lys Ile Leu Phe Val Cys Thr Gly Asn Thr Cys Arg Ser Pro
  1               5                  10                  15
Leu Ala Glu Ser Ile Ala Lys Glu Val Met Pro Asn His Gln Phe Glu
             20                  25                  30
Ser Arg Gly Ile Phe Ala Val Asn Asn Gln Gly Val Ser Asn Tyr Val
         35                  40                  45
Glu Asp Leu Val Glu Glu His His Leu Ala Glu Thr Thr Leu Ser Gln
     50                  55                  60
Gln Phe Thr Glu Ala Asp Leu Lys Ala Asp Ile Ile Leu Thr Met Ser
 65                  70                  75                  80
Tyr Ser His Lys Glu Leu Ile Glu Ala His Phe Gly Leu Gln Asn His
                 85                  90                  95
Val Phe Thr Leu His Glu Tyr Val Lys Glu Ala Gly Glu Val Ile Asp
            100                 105                 110
Pro Tyr Gly Gly Thr Lys Glu Met Tyr Val His Thr Tyr Glu Glu Leu
        115                 120                 125
Val Ser Leu Ile Leu Lys Leu Lys Asp Ile Ile Cys Arg Ser His His
    130                 135                 140
His His His His
145
```

<210> SEQ ID NO 95
<211> LENGTH: 35
<212> TYPE: DNA
<213> ORGANISM: Artificial Sequence
<220> FEATURE:
<223> OTHER INFORMATION: Oligonucleotide Primer.

<400> SEQUENCE: 95

```
ccatgggaaa gattttattc gtttgtacag gtaac                               35
```

<210> SEQ ID NO 96
<211> LENGTH: 43
<212> TYPE: DNA
<213> ORGANISM: Artificial Sequence
<220> FEATURE:
<223> OTHER INFORMATION: Oligonucleotide Primer.

```
<400> SEQUENCE: 96
gagatctgca aataatatct tttaatttta aaattaaaga atg                    43

<210> SEQ ID NO 97
<211> LENGTH: 162
<212> TYPE: DNA
<213> ORGANISM: Artificial Sequence
<220> FEATURE:
<223> OTHER INFORMATION: DNA sequence of portion of pQE-60 vector.

<400> SEQUENCE: 97
ctcgagaaat cataaaaaat ttatttgctt tgtgagcgga taacaattat aatagattca    60
attgtgagcg gataacaatt tcacacagaa ttcattaaag aggagaaatt aaccatggga   120
ggatccagat ctcatcacca tcaccatcac taagcttaat ta                     162

<210> SEQ ID NO 98
<211> LENGTH: 143
<212> TYPE: PRT
<213> ORGANISM: Staphylococcus aureus
<220> FEATURE:
<221> NAME/KEY: MISC_FEATURE
<222> LOCATION: (142)..(142)
<223> OTHER INFORMATION: Corresponding codon encodes either asparagine
      or histidine.

<400> SEQUENCE: 98

Met Phe Met Gly Glu Tyr Asp His Gln Leu Asp Thr Lys Gly Arg Met
1               5                   10                  15

Ile Ile Pro Ser Lys Phe Arg Tyr Asp Leu Asn Glu Arg Phe Ile Ile
            20                  25                  30

Thr Arg Gly Leu Asp Lys Cys Leu Phe Gly Tyr Thr Leu Asp Glu Trp
        35                  40                  45

Gln Gln Ile Glu Glu Lys Met Lys Thr Leu Pro Met Thr Lys Lys Asp
    50                  55                  60

Ala Arg Lys Phe Met Arg Met Phe Phe Ser Gly Ala Val Glu Val Glu
65                  70                  75                  80

Leu Asp Lys Gln Gly Arg Ile Asn Ile Pro Gln Asn Leu Arg Lys Tyr
                85                  90                  95

Ala Asn Leu Thr Lys Glu Cys Thr Val Ile Gly Val Ser Asn Arg Ile
            100                 105                 110

Glu Ile Trp Asp Arg Glu Thr Trp Asn Asp Phe Tyr Glu Glu Ser Glu
        115                 120                 125

Glu Ser Phe Glu Asp Ile Ala Glu Asp Leu Ile Asp Phe Xaa Phe
    130                 135                 140

<210> SEQ ID NO 99
<211> LENGTH: 144
<212> TYPE: PRT
<213> ORGANISM: Staphylococcus aureus
<220> FEATURE:
<221> NAME/KEY: misc_feature
<222> LOCATION: (143)..(143)
<223> OTHER INFORMATION: Corresponding codon encodes either asparagine
      or histidine.

<400> SEQUENCE: 99

Met Gly Phe Met Gly Glu Tyr Asp His Gln Leu Asp Thr Lys Gly Arg
1               5                   10                  15

Met Ile Ile Pro Ser Lys Phe Arg Tyr Asp Leu Asn Glu Arg Phe Ile
            20                  25                  30
```

-continued

```
Ile Thr Arg Gly Leu Asp Lys Cys Leu Phe Gly Tyr Thr Leu Asp Glu
        35                  40                  45

Trp Gln Gln Ile Glu Glu Lys Met Lys Thr Leu Pro Met Thr Lys Lys
    50                  55                  60

Asp Ala Arg Lys Phe Met Arg Met Phe Phe Ser Gly Ala Val Glu Val
65                  70                  75                  80

Glu Leu Asp Lys Gln Gly Arg Ile Asn Ile Pro Gln Asn Leu Arg Lys
                85                  90                  95

Tyr Ala Asn Leu Thr Lys Glu Cys Thr Val Ile Gly Val Ser Asn Arg
            100                 105                 110

Ile Glu Ile Trp Asp Arg Glu Thr Trp Asn Asp Phe Tyr Glu Glu Ser
        115                 120                 125

Glu Glu Ser Phe Glu Asp Ile Ala Glu Asp Leu Ile Asp Phe Xaa Phe
    130                 135                 140
```

ANTIMICROBIAL METHODS AND MATERIALS

CONTINUING APPLICATION DATA

This application claims the benefit of U.S. application Ser. No. 09/544,372, filed Apr. 6, 2000, which was subsequently converted to a U.S. Provisional Application entitled "Antimicrobial Methods and Materials," Serial No. 60/266,327, filed Apr. 6, 2000 now abandoned, which is incorporated by reference herein.

BACKGROUND

The staphylococci, of which *Staphylococcus aureus* is the most important human pathogen, are hardy, gram-positive bacteria that colonize the skin of most humans. Staphylococcal strains that produce coagulase are designated *S. aureus*; other clinically important coagulase-negative staphylococci are *S. epidermidis* and *S. saprophyticus*. When the skin or mucous membrane barriers are disrupted, staphylococci can cause localized and superficial infections that are commonly harmless and self-limiting. However, when staphylococci invade the lymphatics and the blood, potentially serious complications may result, such as bacteremia, septic shock, and serious metastatic infections, including endocarditis, arthritis, osteomyelitis, pneumonia and abscesses in virtually any organ. Certain strains of *S. aureus* produce toxins that cause skin rashes, food poisoning, or multisystem dysfunction (as in toxic shock syndrome). *S. aureus* and *S. epidermidis* together have become the most common cause of nosocomial non-urinary tract infection in U.S. hospitals. They are the most frequently isolated pathogens in both primary and secondary bacteremias and in cutaneous and surgical wound infections. See generally *Harrison's Principles of Internal Medicine*, 13th ed., Isselbacher et al., eds., McGraw-Hill, New York (1994), particularly pages 611–617.

Transient colonization of the nose by *S. aureus* is seen in 70 to 90 percent of people, of which 20 to 30 percent carry the bacteria for relatively prolonged periods of time. Independent colonization of the perineal area occurs in 5 to 20 percent of people. Higher carriage rates of *S. aureus* have been documented in persons with atopic dermatitis, hospital employees, hospitalized patients, patients whose care requires frequent puncture of the skin, and intravenous drug abusers.

Infection by staphylococci usually results from a combination of bacterial virulence factors and a diminution in host defenses. Important microbial factors include the ability of the staphylococcus to survive under harsh conditions, its cell wall constituents, the production of enzymes and toxins that promote tissue invasion, its capacity to persist intracellularly in certain phagocytes, and its potential to acquire resistance to antimicrobial agents. Important host factors include an intact mucocutaneous barrier, an adequate number of functional neutrophils, and removal of foreign bodies or dead tissue.

Cell wall components of *S. aureus* include a large peptidoglycan complex that confers rigidity on the organism and enables it to survive under unfavorable osmotic conditions, a unique teichoic acid linked to peptidoglycan, and protein A, which is found both attached to peptidoglycan over the outermost parts of the cell and released in soluble form. Proteins designated femA and femB are involved in the formation of cell wall peptidoglycan pentaglycine cross-bridges and are factors in methicillin resistance (Berger-Bachi et al, *Mol. Gen. Genet.*, 219, 263–269 (1989)). *S. aureus* also has specific receptors for laminin and fibronectin that may mediate the organism's spread through the bloodstream to other tissues. Both peptidoglycan and teichoic acid are capable of activating the complement cascade via the alternative pathway. *S. aureus* also appears to activate tissue factor in the coagulation pathway.

Certain enzymes produced by *S. aureus* may play a role in virulence. Catalase degrades hydrogen peroxide and may protect the organism during phagocytosis. Coagulase is present in both soluble and cell-bound forms and causes plasma to clot by formation of thrombin-like material. The high correlation between coagulase production and virulence suggests that this substance is important in the pathogenesis of staphylococcal infections, but its precise role as a determinant of pathogenicity has not been determined. Many strains also produce hyaluronidase, an enzyme that degrades hyaluronic acid in the connective tissue matrix and that may promote spreading of infection. A trypsin-like protease from some strains enhances influenza virus infection by proteolytic cleavage of the viral precursor hemagglutinin into its active fragments and may contribute to the morbidity of such co-infections. *S. aureus* produces numerous extracellular exotoxins that have been implicated in disease processes. The exfoliatin toxins A and B, the staphylococcal enterotoxins, and the toxic shock syndrome toxin, TSST-1, belong to the growing family of microbial superantigens that activate T cells and monocytes/macrophages, resulting in the production of cytokines that mediate local or systemic effects depending on the amount of toxin formed, the immune status of the host, and the access of the toxin to the circulation. The exfoliatin toxins mediate the dermatologic manifestations of the staphylococcal scalded-skin syndrome and bullous impetigo. These toxins cause intraepidermal cleavage of the skin at the stratum granulosum, leading to bullae formation and denudation. Seven distinct enterotoxins (A, B, C1, C2, C3, D, and E) have been implicated in food poisoning due to *S. aureus*. These toxins enhance intestinal peristalsis and appear to induce vomiting by a direct effect on the central nervous system. Toxic shock syndrome (TSS) is most commonly mediated by TSST-1, which is present in 5 to 25 percent of clinical isolates of *S. aureus*. TSS is also mediated less frequently by enterotoxin B and, rarely, enterotoxin C1.

*S. aureus* produces other toxins whose role in virulence is incompletely understood. Four different red blood cell hemolysins, which are designated alpha, beta, gamma, and delta toxins, have been identified. Alpha toxin also causes necrosis of the skin when injected subcutaneously into animals, while delta toxin also inhibits water absorption in the intestines and may play a role in the acute watery diarrhea seen in some cases of staphylococcal infection. Leukocidin lyses granulocyte and macrophage membranes by producing membrane pores permeable to cations.

The agr, xpr, sae and sar coding sequences have been identified as being involved in the regulation of staphylococcal exotoxins. See U.S. Pat. No. 5,587,228 and International Patent Publication Nos. WO 96/10579 and WO 97/11690. Of interest is the report in WO 97/11690 of screening for inhibitors of these regulatory systems.

Staphylococci can invade the skin or mucosa through plugged hair follicles and sebaceous glands or areas traumatized by burns, wounds, abrasions, insect bites, or dermatitis. Staphylococci often colonize prosthetic devices and intravenous catheters; *S. aureus* infection of the vascular access site is a major cause of morbidity and death among patients on hemodialysis. Colonization and invasion of the lungs may occur with endotracheal intubation, or when the lungs' clearance mechanisms are depressed, e.g., after viral infections, after aspiration, or in patients with cystic fibrosis. Mucosal damage to the gastrointestinal tract following cytotoxic chemotherapy or radiotherapy predisposes to invasion from that site.

Once the skin or mucosa have been breached, local bacterial multiplication is accompanied by inflammation, neutrophil accumulation, tissue necrosis, thrombosis and fibrin deposition at the site of infection. Later, fibroblasts create a relatively avascular wall about the area. When host mechanisms fail to contain the cutaneous or submucosal infection, staphylococci may enter the lymphatics and the bloodstream. Common sites of metastatic spread include the lungs, kidneys, cardiac valves, myocardium, liver, spleen, bones and brain.

Bacteremia due to *S. aureus* may arise from any local infection, at either extravascular (cutaneous infections, burns, cellulitis, osteomyelitis, arthritis) or intravascular foci (intravenous catheters, dialysis access sites, intravenous drug abuse). Commonly, the disease progresses more slowly, with hectic fever and metastatic abscess formation. Rarely, patients with bacteremia die within 12 to 24 hours with high fever, tachycardia, cyanosis, and vascular collapse. Disseminated intravascular coagulation may produce a disease mimicking meningococcemia.

A major complication of *S. aureus* bactereria is endocarditis. *S. aureus* is the second most common cause of endocarditis and the most common cause among drug addicts. The disease is typically acute, with high fever, progressive anemia, and frequent embolic and extracardiac septic complications. Valve ring and myocardial abscesses are common. The mortality rate is 20 to 30 percent.

Staphylococcal scalded-skin syndrome (SSSS) is a generalized exfoliative dermatitis that is a complication of infection by exfoliatin toxin-producing strains of *S. aureus*. The disease typically occurs in newborns (Ritter's disease) and in children under the age of five. A scarlatiniform rash begins in the perioral area, becomes generalized over the trunk and extremities, and finally desquamates. The disease may consist of rash alone (staphylococcal scarlet fever), or large, flaccid bullae develop that may be localized (more common in adults) or generalized. The bullae burst, resulting in red, denuded skin resembling a burn. Most adults with SSSS are immunosuppressed or have renal insufficiency. Blood cultures are frequently positive, and mortality is significant.

Toxic shock syndrome (TSS) is a multisystem disease mediated by toxins (generally TSST-1, and less frequently enterotoxins B and C1) produced by certain strains of *S. aureus*. It was first described in children, but in 1980 became epidemic among young women, with onset during menstruation. The diagnosis of TSS is based on clinical criteria that include high fever, a diffuse rash that desquamates on the palms and soles over the subsequent one or two weeks, hypotension that may be orthostatic, and evidence of involvement in three or more organ systems. Such involvement commonly includes gastrointestinal dysfunction (vomiting or diarrhea), renal or hepatic insufficiency, mucous membrane hyperemia, thrombocytopenia, myalgias with elevated creatine phosphokinase (CK) levels, and disorientation with a normal cerebrospinal fluid examination. The mortality rate of TSS is three percent.

*S. aureus* causes approximately three percent of community-acquired bacterial pneumonias. This disease occurs sporadically except during influenza outbreaks, when staphylococcal pneumonia is relatively more common, although still less frequent than pneumococcal pneumonia. Primary staphylococcal pneumonia in infants and children frequently presents with high fever and cough. Multiple thin-walled abscesses are seen on the chest X-ray, and empyema formation is common. In older children and healthy adults, staphylococal pneumonia is generally preceded by an influenza-like respiratory infection. Onset of staphylococcal involvement is abrupt, with chills, high fever, progressive dyspnea, cyanosis, cough, pleural pain, and sometimes bloody sputum. Staphylococcal pneumonia is seen more frequently in patients with cystic fibrosis, in intubated patients in intensive care units and in debilitated patients who are prone to aspiration.

*S. aureus* is responsible for the majority of cases of acute osteomyelitis. Although the disease is most common in people under the age of 20, it is becoming increasingly prevalent in adults over 50, particularly with involvement of the spine. A primary portal of entry is frequently not identified, although many patients give a history of preceding trauma to the involved area. Once established, infection spreads through the bone to the periosteum or along the marrow cavity. Rarely, the joint capsule is penetrated, producing pyogenic arthritis. Osteomyelitis in children may present as an acute process beginning abruptly with chills, high fever, nausea, vomiting, and progressive pain at the site of bony involvement.

*S. aureus* causes 1 to 9 percent of cases of bacterial meningitis and 10 to 15 percent of brain abscesses. Most commonly, the bacteria are spread from a focus outside the central nervous system, typically from infective endocarditis, by extension from a paraspinal or pararneningeal abscess, or by nosocomial infection following neurosurgical procedures. Over 50 percent of epidural abscesses are due to *S. aureus*; up to half of these cases may be associated with vertebral osteomyelitis. Patients present with either acute or chronic back pain, usually with low-grade fever and malaise. The onset of radicular pain is an ominous sign that the disease may progress to neurologic dysfunction and ultimate paralysis.

Antimicrobial resistance by staphylococci favors their persistence in the hospital environment. Over 90 percent of both hospital and community strains of *S. aureus* causing infection are resistant to penicillin. This resistance is due to the production of β-lactamase enzymes; the nucleotides encoding these enzymes are usually carried by plasmids. Infections due to organisms with such acquired resistance can sometimes be treated with penicillinase-resistant β-lactam antimicrobial agents. However, the true penicillinase-resistant *S. aureus* organisms, called methicillin-resistant *S. aureus* (MILSA), are resistant to all the β-lactam antimicrobial agents as well as the cephalosporins. MRSA resistance is chromosomally mediated and involves production of an altered penicillin-binding protein (PBP 2a or PBP 2') with a low binding affinity for β-lactams. MRSA frequently also have acquired plasmids mediating resistance to erythromycin, tetracycline, chloramphenicol, clindamycin, and aminoglycosides. MRSA have become increasingly common worldwide, particularly in tertiary-care referral hospitals. In the United States, approximately 5 percent of hospital isolates of *S. aureus* are methicillin-resistant.

Thus, there continues to exist a need for new agents useful for treating bacterial infections, particularly those caused by antibiotic-resistant bacteria, and for methods of identifying such new agents. Such methods ideally would identify agents that are unrelated to existing antimicrobials and that target different aspects of staphylococcal invasion of and replication in the host, compared to existing antimicrobials.

SUMMARY OF THE INVENTION

The present invention provides a method for identifying an agent that binds a polypeptide. The method includes contacting a polypeptide and an agent to form a mixture, wherein the polypeptide is encoded by a coding sequence including a nucleotide sequence SEQ ID NO: 1, 3, 5, 7, 9, 11, 13, 15, 17, 19, 21, or 23, or wherein the polypeptide is encoded by an essential coding sequence having at least about 57% structural similarity to SEQ ID NO: 1, 3, 5, 7, 9, 11, 13, 15, 17, 19, 21, or 23. Whether the agent binds the polypeptide is then determined by using, for instance, an enzyme assay, a binding assay, or a ligand binding assay.

The method may further include determining whether the agent decreases the growth rate of a microbe, for instance *S. aureus*. Such a method includes contacting a microbe with the agent, incubating the microbe and the agent under conditions suitable for growth of the microbe that is not contacted with the agent, and determining the growth rate of the microbe, wherein a decrease in growth rate compared to the microbe that is not contacted with the agent indicates the agent decreases the growth rate of the microbe. The microbe may be in vitro or in vivo. The invention includes an agent identified these methods.

In another aspect, the invention provides a method for identifying an agent that decreases the growth rate of a microbe, for instance *S. aureus*. The method includes contacting a microbe with an agent, wherein the agent binds to a polypeptide encoded by a coding sequence comprising a nucleotide sequence selected from the group consisting of SEQ ID NOs: 1, 3, 5, 7, 9, 11, 13, 15, 17, 19, 21, and 23. Alternatively, the agent binds to a polypeptide encoded by an essential coding sequence including a nucleotide sequence having at least about 57 percent identity with a nucleotide sequence selected from the group consisting of SEQ ID NO: 1, 3, 5, 7, 9, 11, 13, 15, 17, 19, 21, or 23. The microbe and the agent are incubated under conditions suitable for growth of the microbe that is not contacted with the agent, and the growth rate of the microbe is determined, wherein a decrease in growth rate compared to the microbe that is not contacted with the agent indicates the agent decreases the growth rate of the microbe. The microbe may be in vitro or in vivo. The invention includes an agent identified these methods.

The present invention also provides a method for decreasing the growth rate of a microbe, for instance *S. aureus*. The method includes contacting a microbe with an agent that binds to a polypeptide encoded by a coding sequence that includes a nucleotide sequence SEQ ID NO: 1, 3, 5, 7, 9, 11, 13, 15, 17, 19, 21, or 23. Alternatively, the agent binds to a polypeptide encoded by an essential coding sequence including a nucleotide sequence having at least about 57 percent identity with a nucleotide sequence selected from the group consisting of SEQ ID NOs: 1, 3, 5, 7, 9, 11, 13, 15, 17, 19, 21, or 23. The microbe may be in vitro or in vivo.

In another aspect, the present invention provides a method for making a microbe, for instance an *S. aureus*, with reduced virulence. The method includes altering a coding sequence in an *S. aureus* to include a mutation, where the non-mutagenized coding sequence (i.e., the coding sequence before being mutagenized) includes a nucleotide sequence SEQ ID NOS: 1, 3, 5, 7, 9, 11, 13, 15, 17, 19, 21, or 23. Alternatively, the method includes altering an essential coding sequence in an *S. aureus* to include a mutation, wherein the non-mutagenized coding sequence includes a nucleotide sequence having at least about 57 percent identity to a nucleotide sequence SEQ ID NO: 1, 3, 5, 7, 9, 11, 13, 15, 17, 19, 21, or 23. Next, it is determined if the *S. arueus* that includes the mutation has reduced virulence compared to an *S. arueus* that does not include the mutation. The mutation may be, for example, a deletion mutation, an insertion mutation, a nonsense mutation, or a missense mutation. The present invention includes such an *S. aureus* having reduced virulence, and a vaccine composition that includes the *S. aureus*.

The present invention further provides an isolated polynucleotide that includes a nucleotide sequence SEQ ID NOS: 1, 3, 5, 7, 9, 11, 13, 15, 17, 19, 21, or 23, and an isolated polynucleotide that includes a nucleotide sequence having at least about 57 percent structural similarity with a nucleotide sequence SEQ ID NO: 1, 3, 5, 7, 9, 11, 13, 15, 17, 19, 21, or 23, wherein the isolated polynucleotide includes an essential coding sequence. In another aspect, the present invention provides an isolated polynucleotide consisting essentially of a nucleotide sequence SEQ ID NO: 1, 3, 5, 7, 9, 11, 13, 15, 17, 19, 21, or 23, wherein the polynucleotide optionally further includes from zero to up to about 5,000 nucleotides upstream and/or downstream of the nucleotide sequence SEQ ID NO: 1, 3, 5, 7, 9, 11, 13, 15, 17, 19, 21, or 23, and an n isolated polynucleotide consisting essentially of a nucleotide sequence having at least about 57 percent structural similarity with a nucleotide sequence SEQ ID NO: 1, 3, 5, 7, 9, 11, 13, 15, 17, 19, 21, or 23, wherein the isolated polynucleotide includes an essential coding sequence.

Definitions

As used herein, the term "agent" refers to chemical compounds, including, for instance, a peptidomimetic, an organic compound, an inorganic compound, or a polypeptide that binds to a particular polypeptide.

As used herein, the term "polypeptide" refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like.

The term "binds to a polypeptide" refers to a condition of proximity between an agent and a polypeptide. The association may be non-covalent, wherein the juxtaposition is energetically favored by hydrogen bonding, van der Waals forces, or electrostatic interactions, or it may be covalent.

As used herein, growth of a microbe "in vitro" refers to growth, for instance, in a test tube or on an agar plate. Growth of a microbe "in vivo" refers to growth, for instance, in a cultured cell or in an animal.

As used herein, the term "microbe" and "bacteria" are used interchangeably and include single celled prokaryotic and lower eukaryotic (e.g., fungi) organisms, preferably prokaryotic organisms.

BRIEF DESCRIPTION OF THE FIGURES

FIG. 1a-1. The nucleotide sequence of the coding sequences of 14 *S. aureus* coding sequences (SEQ ID NOS: 1, 3, 5, 7, 9, 11, 13, 15, 17, 19, 21, and 23), the predicted sequence of the peptide (SEQ ID NOS: 2, 4, 6, 8, 10, 12, 14, 16, 18, 20, 22, and 24, respectively) encoded by each coding sequence, and primer pairs used for preparing fragments for insertion into a temperature sensitive plasmid (SEQ ID NOS: 25–48). The two underlined sequences in each coding sequence correspond to the primers listed below the coding sequence.

FIG. 2a-1. The nucleotide sequence of each of the 14 *S. aureus* coding sequences cloned for expression in *E. coli*

(SEQ ID NOS: 49, 53, 57, 61, 65, 69, 73, 77, 81, 85, 89, and 93), the predicted sequence of the peptide (SEQ ID NOS: 50, 54, 58, 62, 66, 70, 74, 78, 82, 86, 90, and 94, respectively) encoded by each coding sequence after insertion into the appropriate expression plasmid, and the sequence of the primer pair (SEQ ID NOS: 51, 52, 55, 56, 59, 60, 63, 64, 67, 68, 71, 72, 75, 76, 79, 80, 83, 84, 87, 88, 91, 92, 95, and 96) used to clone the S. aureus coding sequences by amplification. The underlined ATGG in SEQ ID NOS: 49, 57, 61, 65, 69, 73, and 77 shows the location of a portion of the NcoI restriction site added to the coding sequence by the forward primer for cloning into the expression vector pQE-60. The coding sequence of FIG. 2b (SEQ ID NO: 53) is cloned into the expression vector pQE-70. The underlined AGATCT in SEQ ID NOS: 49, 53, 57, 61, 65, 69, 77, 81, 85, 89, and 93 shows the location of the BglII restriction site added to the coding sequence by the reverse primer. The underlined GGATCT in SEQ ID NO: 73 shows the location of the ligation the digested BamHI restriction site of the amplified fragment with the digested BglII restriction site of the vector.

DETAILED DESCRIPTION OF PREFERRED EMBODIMENTS OF THE INVENTION

The sequence of the S. aureus genome has been determined and includes about 3,500 coding sequences (see, for instance, Kunsch et al., EP 0 786 519 A2). As used herein, the terms "coding sequence," "coding region," and "open reading frame" are used interchangeably herein and refer to a nucleotide sequence that encodes a polypeptide and, when placed under the control of appropriate regulatory sequences, expresses the encoded polypeptide. The boundaries of a coding region are generally determined by a translation start codon at its 5' end and a translation stop codon at its 3' end. A regulatory sequence is a nucleotide sequence that regulates expression of a coding region to which it is operably linked. Nonlimiting examples of regulatory sequences include promoters, transcription initiation sites, translation start sites, translation stop sites, and terminators. "Operably linked" refers to a juxtaposition wherein the components so described are in a relationship permitting them to function in their intended manner. A regulatory sequence is "operably linked" to a coding region when it is joined in such a way that expression of the coding region is achieved under conditions compatible with the regulatory sequence.

At this time, it is not possible to predict the function of some of the polypeptides that the approximately 3,500 coding sequences of the S. aureus genome are predicted to encode. This subset of coding sequences are referred to herein as "unknown coding sequences." Among the large number of unknown coding sequences in the S. aureus genome, those that are essential for cell growth are potential novel targets for antimicrobial therapy. "Essential coding sequences," as used herein, are coding sequences that encode polypeptides having an unknown function but are essential for the bacterial cell to grow in vitro or in vivo, preferably in vitro. Such polypeptides are referred to herein as "essential polypeptides." Identification of these essential coding sequences provides a means for discovering new agents with different targets and mechanisms of action compared to existing agents that are used to inhibit bacteria, preferably S. epidermidis, S. saprophyticus, or S. aureus, more preferably S. aureus.

The identification of essential coding sequences of microbes, preferably S. epidermidis, S. saprophyticus, or S. aureus, more preferably S. aureus, that are useful in the present invention can begin by identifying coding sequences encoding a polypeptide having no known function. The coding sequences can be identified in databases, including, for instance, the S. aureus databases available from the University of Oklahoma, TIGR, NCBI, Sanger, the HGS contig database, and the HGS GSTS database. The identification of such coding sequences can include constructing contigs from data present in such databases.

As described herein, coding sequences are typically identified by analyzing publicly known polynucleotide sequences. The data obtained from the database contained the nucleotide sequence of genomic clones and predicted open reading frames. However, even though the putative coding sequences may have been known, there was no indication that the coding sequence were in fact expressed, or in fact essential. For instance, there is limited data known to the art regarding regulatory regions required for the transcription of a nucleotide sequence in S. aureus. Moreover, there is generally no evidence that the essential coding sequences identified herein are actually expressed. Thus, a person of ordinary skill, having the polynucleotide sequence of a genomic clone, would not be able to predict that an open reading frame would be transcribed, or that a coding sequence was essential.

Typically, whether an coding sequence is an essential coding sequence can be determined by inactivating the coding sequence in a bacterial cell and determining whether the bacterial cell is able to grow. Growth can be measured in vitro or in vivo, preferably in vitro. Inactivating a coding sequence is done by mutating a coding sequence present in a bacterial cell. Mutations include, for instance, a deletion mutation (i.e., the deletion of nucleotides from the coding sequence), an insertion mutation (i.e., the insertion of additional nucleotides into the coding sequence), a nonsense mutation (i.e., changing a nucleotide of a codon so the codon encodes a different amino acid), and a missense mutation (i.e., changing a nucleotide of a codon so the codon functions as a stop codon). Some insertion mutations and some deletion mutations result in frame-shift mutations. Preferably, a coding sequence in a bacterial cell is engineered to contain a deletion.

In general, an internal fragment of a selected essential coding sequence can be isolated or synthesized by methods known in the art, including, for instance, the polymerase chain reaction (PCR). Typically, the internal fragment is about 150 base pairs to about 350 base pairs in length, preferably about 300 base pairs. The internal fragment preferably corresponds to the 5' end of the coding sequence. Preferably, the primers used to amplify the internal fragment contain a restriction site to allow ligation of the amplified internal fragment into a vector. For instance, when the vector is pSPT246 (described herein), one primer may contain a PstI site and the other primer may contain a SacI site.

The internal fragment is typically ligated into a vector that can be used to inactivate the unknown coding sequence in the bacterial cell and determine if the unknown coding sequence is an essential coding sequence. Useful vectors include those that are unable to replicate under certain conditions in the bacterial cell that contains the unknown coding sequence to be inactivated Preferably, a vector is temperature sensitive, i.e., it is unable to replicate in S. aureus at higher temperatures of, for instance, greater than about 42° C. Preferably, a vector is a shuttle vector, i.e., it is able to replicate in E. coli and S. aureus under the appropriate conditions. Examples of temperature sensitive plasmids that can be used to inactivate an unknown coding sequence in S. aureus include pSPT181 (Janzon and Arvidson, *EMBO J.*, 9, 1391–1399 (1990), and pSPT246.

Using these methods, the following essential coding sequences have been identified: SEQ ID NOS: 1, 3, 5, 7, 9, 11, 13, 15, 17, 19, 21, and 23. The polypeptides encoded by the essential coding sequences are SEQ ID NOS: 2, 4, 6, 8, 10, 12, 14, 16, 18, 20, 22, and 24, respectively. The essential coding sequences of the present invention include essential coding sequences that are similar to the coding sequences present in SEQ ID NOS: 1, 3, 5, 7, 9, 11, 13, 15, 17, 19, 21, or 23. The similarity is referred to as structural similarity and is determined by aligning the residues of the two polynucleotides (i.e., the nucleotide sequence of the candidate coding sequence and the nucleotide sequence of the coding region of SEQ ID NO: 1, 3, 5, 7, 9, 11, 13, 15, 17, 19, 21, or 23,) to optimize the number of identical nucleotides along the lengths of their sequences; gaps in either or both sequences are permitted in making the alignment in order to optimize the number of shared nucleotides, although the nucleotides in each sequence must nonetheless remain in their proper order. A candidate coding region is the coding region being compared to a coding region present in SEQ ID NO: 1, 3, 5, 7, 9, 11, 13, 15, 17, 19, 21, or 23. A candidate nucleotide sequence can be isolated from a microbe, preferably S. aureus, or can be produced using recombinant techniques, or chemically or enzymatically synthesized. Preferably, two nucleotide sequences are compared using the Blastn program of the BLAST 2 search algorithm, as described by Tatusova, et al. (*FEMS Microbiol Lett* 1999, 174:247–250), and available on the world wide web at ncbi.nlm.nih.gov/gorf/bl2.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, a polynucleotide includes a nucleotide sequence having a structural similarity with the coding region of SEQ ID NO: 1, 3, 5, 7, 9, 11, 13, 15, 17, 19, 21, or 23 of, in increasing order of preference, at least about 57%, at least about 60%, at least about 70%, at least about 80%, most preferably at least about 90% identity.

The present invention includes isolated polynucleotides that include a nucleotide sequence SEQ ID NO: 1, 3, 5, 7, 9, 11, 13, 15, 17, 19, 21, or 23. As used herein, an "isolated" polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptides or polynucleotides and associated cellular products or other impurities. An isolated polynucleotide of the invention may include a nucleotide sequence having, in increasing order of preference, at least about 57%, at least about 60%, at least about 70%, at least about 80%, most preferably at least about 90% structural similarity with a nucleotide sequence SEQ ID NO: 1, 3, 5, 7, 9, 11, 13, 15, 17, 19, 21, or 23, where the isolated polynucleotide includes an essential coding sequence. The present invention also includes the polypeptides encoded by the coding sequences.

Another aspect of the invention includes isolated polynucleotides consisting essentially of a nucleotide sequence SEQ ID NO: 1, 3, 5, 7, 9, 11, 13, 15, 17, 19, 21, or 23. The polynucleotide optionally further includes from zero to up to about 5,000 nucleotides upstream and/or downstream of the nucleotide sequence SEQ ID NO: 1, 3, 5, 7, 9, 11, 13, 15, 17, 19, 21, or 23. An isolated polynucleotide of the invention may consist essentially of a nucleotide sequence having, in increasing order of preference, at least about 57%, at least about 60%, at least about 70%, at least about 80%, most preferably at least about 90% structural similarity with a nucleotide sequence SEQ ID NO: 1, 3, 5, 7, 9, 11, 13, 15, 17, 19, 21, or 23, where the isolated polynucleotide includes an essential coding sequence. The polynucleotide optionally further includes from zero to up to about 5,000 nucleotides upstream and/or downstream of the nucleotide sequence SEQ ID NO: 1, 3, 5, 7, 9, 11, 13, 15, 17, 19, 21, or 23. The present invention also includes the polypeptides encoded by the coding sequences.

Insertional inactivation of essential coding sequences allows different classes of essential coding sequences to be identified. Examples of different classes include, for instance, coding sequences encoding proteins involved in cell surface metabolism, enzymes involved in cellular biosynthetic pathways including cell wall biosynthesis and assembly, components of the TCA cycle, proteins similar to oligopeptide transport proteins of the ATP-binding cassette (ABC) transporter superfamily, and involved in cellular regulatory and repair processes, and coding sequences affecting morphogenesis and cell division, secretion and sorting of proteins, and signal transduction systems.

The essential coding sequences may be cloned by PCR, using microbial, preferably *S. epidermidis, S. saprophyticus*, or *S. aureus*, more preferably *S. aureus*, genomic DNA as the template. For ease of inserting the open reading frame into expression vectors, PCR primers may be chosen so that the PCR-amplified coding sequence has a restriction enzyme site at the 5' end preceding the initiation codon ATG, and a restriction enzyme site at the 3' end after the termination codon TAG, TGA or TAA. If desirable, the codons in the coding sequence may be changed, without changing the amino acids, to optimize expression of polypeptide encoded by an essential coding sequence. For instance, if an essential coding sequence is to be expressed in *E. coli*, the codons of the coding sequence can be changed to comply with the *E. coli* codon preference described by Grosjean et al. (Fiers, *Gene*, 18, 199–209 (1982)), and Konigsberg et al. (Proc. Natl. Acad. Sci. (USA), 80, 687–691 (1983)). Optimization of codon usage may lead to an increase in the expression of the encoded polypeptide when produced in a microbe other than the microbe from which the essential coding sequence was isolated. If the polypeptide is to be produced extracellularly, either in the periplasm of, for instance, *E. coli* or other bacteria, or into the cell culture medium, the coding sequence may be cloned without its initiation codon and placed into an expression vector behind a signal sequence.

Proteins may be produced in prokaryotic or eukaryotic expression systems using known promoters, vectors, and hosts. Such expression systems, promoters, vectors, and hosts are known to the art. A suitable host cell may be used for expression of the polypeptide, such as *E. coli*, other bacteria, including Bacillus and *S. aureus*, yeast, including *Pichia pastoris* and *Saccharomyces cerevisiae*, insect cells, or mammalian cells, including CHO cells, utilizing suitable vectors known in the art. Proteins may be produced directly or fused to a polypeptide, and either intracellularly or extracellularly by secretion into the periplasmic space of a bacterial cell or into the cell culture medium. Secretion of a protein typically requires a signal peptide (also known as pre-sequence); a number of signal sequences from prokaryotes and eukaryotes are known to function for the secretion of recombinant proteins. During the protein secretion process, the signal peptide is removed by signal peptidase to yield the mature protein.

The polypeptide encoded by an essential coding sequence may be isolated. To simplify the isolation process, a purification tag may be added either at the 5' or 3' end of the coding sequence. Commonly used purification tags include a stretch of six histidine residues (U.S. Pat. Nos. 5,284,933 and 5,310,663), a streptavidin-affinity tag described by Schmidt and Skerra, *Protein Engineering*, 6, 109–122 (1993), a FLAG peptide (Hopp et al, *Biotechnology*, 6, 1205–1210 (1988)), glutathione S-transferase (Smith and Johnson, *Gene*, 67, 31–40 (1988)), and thioredoxin (LaVallie et al., *Bio/Technology*, 11, 187–193 (1993)). To remove these peptide or polypeptides, a proteolytic cleavage recognition site may be inserted at the fusion junction. Commonly used proteases are factor Xa, thrombin, and enterokinase. Preferably, a polypeptide encoded by an essential coding sequence is isolated, more preferably, purified.

The identification of essential coding sequences renders them useful in methods of identifying new agents according to the present invention. Such methods include assaying potential agents for the ability to interfere with expression of an essential coding sequence, thereby preventing the expression and decreasing the concentration of a polypeptide encoded by the essential coding sequence. The essential coding sequences are represented by the DNA sequences set forth in any one of SEQ ID NOS: 1, 3, 5, 7, 9, 11, 13, 15, 17, 19, 21, or 23. The polypeptides encoded by the essential coding sequences are SEQ ID NOS: 2, 4, 6, 8, 10, 12, 14, 16, 18, 20, 22, and 24, respectively. Without intending to be limiting, it is anticipated that agents can act by, for instance, interacting with an essential coding region, with a nucleotide sequence that is adjacent to an essential coding sequence (e.g., a promoter sequence), or inhibiting expression of a polypeptide involved in regulating expression of an essential coding region. Agents that can be used to inhibit the expression of an essential coding region include, for instance, the use of anti-sense polynucleotides that are complementary to the mRNA molecules transcribed from an essential coding sequence, and double stranded RNA (Fire et al., *Nature*, 391, 806–11 (1998)).

Such methods also include assaying potential agents for the ability to interfere with the function of a polypeptide encoded in whole or in part by a DNA sequence set forth in any one of SEQ ID NOS: 1, 3, 5, 7, 9, 11, 13, 15, 17, 19, 21, or 23, or the complementary strand thereof, followed by identifying agents that are positive in such assays.

A polypeptide produced by the methods described herein may be used in assays including, for instance, high throughput assays, to screen for agents that inhibit the function of the polypeptide. The sources for potential agents to be screened include, for instance, chemical compound libraries, fermentation media of Streptomycetes, other bacteria and fungi, and cell extracts of plants and other vegetations. For proteins with known enzymatic activity, assays may be established based on the activity, and a large number of potential agents are screened for ability to inhibit the activity. Such assays are referred to herein as "enzyme assays." For proteins that interact with another protein or nucleic acid, assays may be established to measure such interaction directly, and the potential agents screened for ability to inhibit the binding interaction (referred to herein as "binding assays"). In another aspect of the invention, assays can be established allowing the identification of agents that bind to a polypeptide encoded by an essential coding sequence (referred to herein as "ligand binding assays"). Without intending to be limiting, an agent can be, for instance, an organic compound, an inorganic compound, a metal, a polypeptide, a non-ribosomal polypeptide, a polyketide, or a peptidomimetic.

For proteins that interact with another protein or nucleic acid, such binding interactions may be evaluated indirectly using the yeast two-hybrid system described in Fields and Song, *Nature*, 340, 245–246 (1989), and Fields and Sternglanz, *Trends in Genetics*, 10, 286–292 (1994). The two-hybrid system is a genetic assay for detecting interactions between two polypeptides. It can be used to identify proteins that bind to a known protein of interest, or to delineate domains or residues critical for an interaction. Variations on this methodology have been developed to clone coding sequences that encode DNA-binding proteins, to identify polypeptides that bind to a protein, and to screen for drugs. The two-hybrid system exploits the ability of a pair of interacting proteins to bring a transcription activation domain into close proximity with a DNA-binding domain that binds to an upstream activation sequence (UAS) of a reporter coding sequence, and is generally performed in yeast. The assay requires the construction of two hybrid coding sequences encoding (1) a DNA-binding domain that is fused to a protein X, and (2) an activation domain fused to a protein Y. The DNA-binding domain targets the first hybrid protein to the UAS of the reporter coding sequence; however, because most proteins lack an activation domain, this DNA-binding hybrid protein does not activate transcription of the reporter coding sequence. The second hybrid protein, which contains the activation domain, cannot by itself activate expression of the reporter because it does not bind the UAS. However, when both hybrid proteins are present, the noncovalent interaction of protein X and protein Y tethers the activation domain to the UAS, activating transcription of the reporter coding sequence. When the polypeptide encoded by an essential coding sequence (protein X, for example) is already known to interact with another protein or nucleic acid (protein Y, for example), this binding assay can be used to detect agents that interfere with the interaction of X and Y. Expression of the reporter coding sequence is monitored as different test agents are added to the system; the presence of an inhibitory agent inhibits binding and results in lack of a reporter signal.

When the function of a polypeptide encoded by an essential coding sequence is unknown and no ligands are known to bind the polypeptide, the yeast two-hybrid assay can also be used to identify proteins that bind to the polypeptide. In an assay to identify proteins that bind to protein X (the target protein), a large number of hybrid coding sequences, each containing a different protein Y, are produced and screened in the assay. Typically, Y is encoded by a pool of plasmids in which total cDNA or genomic DNA is ligated to the activation domain. This system is applicable to a wide variety of proteins, and it is not even necessary to know the identity or function of protein Y. The system is highly sensitive and can detect interactions not revealed by other methods; even transient interactions may trigger transcription to produce a stable mRNA that can be repeatedly translated to yield the reporter protein. When a protein is identified that binds to an essential polypeptide, the two-hybrid system can be used in a binding assay to identify agents that inhibit binding and result in lack of a reporter signal.

Ligand binding assays known to the art may be used to search for agents that bind to the target protein. Without intending to be limiting, one such screening method to identify direct binding of test ligands to a target protein is described in Bowie et al. (U.S. Pat. No. 5,585,277). This method relies on the principle that proteins generally exist as a mixture of folded and unfolded states, and continually alternate between the two states. When a test ligand binds to the folded form of a target protein (i.e., when the test ligand is a ligand of the target protein), the target protein molecule bound by the ligand remains in its folded state. Thus, the folded target protein is present to a greater extent in the presence of a test ligand which binds the target protein, than in the absence of a ligand. Binding of the ligand to the target protein can be determined by any method which distinguishes between the folded and unfolded state of the target protein. The function of the target protein need not be known in order for this assay to be performed.

Another method for identifying ligands for a target protein is described in Wieboldt et al., *Anal. Chem.,* 69, 1683–1691 (1997), incorporated herein by reference. This technique screens combinatorial libraries of 20–30 agents at a time in solution phase for binding to the target protein. Agents that bind to the target protein are separated from other library components by centrifugal ultrafiltration. The specifically selected molecules that are retained on the filter are subsequently liberated from the target protein and analyzed by HPLC and pneumatically assisted electrospray (ion spray) ionization mass spectroscopy. This procedure selects library components with the greatest affinity for the target protein, and is particularly useful for small molecule libraries.

Another method allows the identification of ligands present in a sample using capillary electrophoresis CE (Hughes et al., U.S. Pat. No. 5,783,397). The sample and the target protein are combined and resolved. The conditions of electrophoresis results in simultaneously fractionating the components present in the sample and screening for components that bind to the target molecule. This method is particularly useful for complex samples including, for instance, extracts of plants, animals, microbes, or portions thereof and chemical libraries produced by, for instance, combinatorial chemistry.

The agents identified by the initial screens are evaluated for their effect on survival of microbes, preferably *S. epidermidis, S. saprophyticus,* or *S. aureus,* more preferably *S. aureus.* Agents that interfere with bacterial survival are expected to be capable of preventing the establishment of an infection or reversing the outcome of an infection once it is established. Agents may be bacteriocidal (i.e., the agents kills the microbe and prevents the replication of the microbe) or bacteriostatic (i.e., the agents reversibly prevents replication of the microbe). Preferably, the agent is bacteriocidal. Such agents will be useful to treat a subject infected with *S. aureus* or at risk of being infected by *S. aureus.*

The identification of *S. aureus* essential coding sequences also provides for microorganisms exhibiting reduced virulence, which are useful in vaccines. The term "vaccine" refers to a composition that, upon administration to a subject, will provide protection against an *S. aureus.* Administration of a vaccine to subject will produces an immunological response to the *S. aureus* and result in immunity. A vaccine is administered in an amount effective to result in some therapeutic benefit or effect so as to result in an immune response that inhibits or prevents an infection by *S. aureus* in a subject, or so as to result in the production of antibodies to an *S. aureus.*

Such microorganisms that can be used in a vaccine include *S. aureus* mutants containing a mutation in a coding sequence represented by any one of SEQ ID NOS: 1, 3, 5, 7, 9, 11, 13, 15, 17, 19, 21, or 23, or a coding sequence having structural similarity thereto. Optionally, an *S. aureus* includes more than one mutation. The reduced virulence of these organisms and their immunogenicity may be confirmed by administration to a subject. Animal models useful for evaluating *S. aureus* virulence in a variety of conditions, including for example, pneumonia, peritonitis, endophthalmitis, endocarditis, septicemia, and arthritis, are known to the art.

While it is possible for an avirulent microorganism of the invention to be administered alone, one or more of such mutant microorganisms are preferably administered in a vaccine composition containing suitable adjuvant(s) and pharmaceutically acceptable diluent(s) or carrier(s). The carrier(s) must be "acceptable" in the sense of being compatible with the avirulent microorganism of the invention and not deleterious to the subject to be immunized. Typically, the carriers will be water or saline which will be sterile and pyrogen free. The subject to be immunized is a subject needing protection from a disease caused by a virulent form of *S. aureus.*

Any adjuvant known in the art may be used in the vaccine composition, including oil-based adjuvants such as Freund's Complete Adjuvant and Freund's Incomplete Adjuvant, mycolate-based adjuvants (e.g., trehalose dimycolate), bacteria lipopolysaccharide (LPS), peptidoglycans (i.e., mumins, mucopeptides, or glycoprotelns such as N-Opaca, muramyl dipeptide (MDP), or MDP analogs), proteoglycans (e.g, extracted from Klebsiellapnetanoniae), streptococcal preparations (e.g, OK432), the "Iscoms" of EP 109 942, EP 180 564 and EP 231 039, aluminum hydroxide, saponin, DEAE-dextran, neutral oils (such as miglyol), vegetable oils (such as arachis oil), liposomes, the Ribi adjuvant system (see, for example GB-A-2 189 141), or adjuvants available under the trade designation BIOSTIM (e.g., 01K2) and PLURONIC polyols. Recently, an alternative adjuvant consisting of extracts of Amycolata, a bacterial genus in the order Actinomycetales, has been described in U.S. Pat. No. 4,877,612. Additionally, proprietary adjuvant mixtures are commercially available. The adjuvant used will depend, in part, on the recipient organism. The amount of adjuvant to administer will depend on the type and size of animal. Optimal dosages may be readily determined by routine methods.

The vaccine compositions optionally may include pharmaceutically acceptable (i.e., sterile and non-toxic) liquid, semisolid, or solid diluents that serve as pharmaceutical vehicles, excipients, or media. Any diluent known in the art may be used. Exemplary diluents include, but are not limited to, polyoxyethylene sorbitan monolaurate, magnesium stearate, methyl-andpropylhydroxybenzoate, talc, alginates, starches, lactose, sucrose, dextrose, sorbitol, mannitol, gum acacia, calcium phosphate, mineral oil, cocoa butter, and oil of theobroma.

The vaccine compositions can be packaged in forms convenient for delivery. The compositions can be enclosed within a capsule, sachet, cachet, gelatin, paper or other container. These delivery forms are preferred when compatible with entry of the immunogenic composition into the recipient organism and, particularly, when the immunogenic composition is being delivered in unit dose form. The dosage units can be packaged, e.g., in tablets, capsules, suppositories or cachets.

The vaccine compositions may be introduced into the subject to be immunized by any conventional method including, e.g, by intravenous, intradermal, intramuscular, intramammary, intraperitoneal, or subcutaneous injection; by oral, sublingual, nasal, anal, vaginal, or transdermal delivery; or by surgical implantation, e.g., embedded under the splenic capsule or in the cornea. The treatment may consist of a single dose or a plurality of doses over a period of time.

It will be appreciated that the vaccine of the invention may be useful in the fields of human medicine and veterinary medicine. Thus, the subject to be immunized may be a human or an animal, for example, cows, sheep, pigs, horses, dogs, cats, and poultry such as chickens, turkeys, ducks and geese.

The present invention is illustrated by the following examples. It is to be understood that the particular examples, materials, amounts, and procedures are to be interpreted broadly in accordance with the scope and spirit of the invention as set forth herein.

EXAMPLE 1

Identification of Essential S. aureus Coding Sequences

Identification of Unknown Coding Sequences

There are about 3500 open reading frames in the HGS database of S. aureus nucleotide sequences. A Fast A homology search was conducted on these open reading frames. This homology search of those open reading frames indicated that 662 of the open reading frames were unknown coding sequences. The methods described herein typically require an open reading frame of about 300 base pairs; 492 of the 662 open reading frames were at least 300 base pairs. Of these 492, 60 had homology with unknown open reading frames from other bacterial species, 270 had no homology with any open reading frames, and 160 had homology with eukaryotic coding sequences.

The nucleotide sequences of the unknown coding sequences are shown in Table 1. Whether these coding sequences were essential was determined as described herein.

TABLE 1

Primers used to amplify unknown coding sequences from S. aureus

| Nucleotide sequence of unknown coding sequence | Primer pair used to amplify coding sequence | Predicted polypeptide |
| --- | --- | --- |
| SEQ ID NO: 1 | SEQ ID NOs: 25–26 | SEQ ID NO: 2 |
| SEQ ID NO: 3 | SEQ ID NOs: 27–28 | SEQ ID NO: 4 |
| SEQ ID NO: 5 | SEQ ID NOs: 29–30 | SEQ ID NO: 6 |
| SEQ ID NO: 7 | SEQ ID NOs: 31–32 | SEQ ID NO: 8 |
| SEQ ID NO: 9 | SEQ ID NOs: 33–34 | SEQ ID NO: 10 |
| SEQ ID NO: 11 | SEQ ID NOs: 35–36 | SEQ ID NO: 12 |
| SEQ ID NO: 13 | SEQ ID NOs: 37–38 | SEQ ID NO: 14 |
| SEQ ID NO: 15 | SEQ ID NOs: 39–40 | SEQ ID NO: 16 |
| SEQ ID NO: 17 | SEQ ID NOs: 41–42 | SEQ ID NO: 18 |
| SEQ ID NO: 19 | SEQ ID NOs: 43–44 | SEQ ID NO: 20 |
| SEQ ID NO: 21 | SEQ ID NOs: 45–46 | SEQ ID NO: 22 |
| SEQ ID NO: 23 | SEQ ID NOs: 47–48 | SEQ ID NO: 24 |

Insertion Inactivation of Unknown Coding Sequences

Inactivation was achieved by integration of a plasmid in the 5' half of the target coding sequence by homologous recombination. An internal fragment of the selected "unknown" coding sequence was synthesized by PCR. The length of the amplified fragment was between about 250 base pairs to about 350 base pairs, and included the 5' end of the coding sequence. The primers used for amplification included additional nucleotides such that a PstI restriction site was added to one end of the amplified fragment and a SacI restriction site was added to the other end of the amplified fragment. The primers are shown in Table 1. The added restriction sites allowed ligation of the amplified fragment to the temperature sensitive shuttle vector pSPT246. pSPT264 was constructed by ligating pRN8103 and pSP64-PolyA. The pRN8103 thermosensitive replication vector contains a unique EcoRI restriction site and the vector cannot replicate in E. coli. pRN8103 is described in Novick et al., (J. Mol. Biol., 192, 209–220 (1986)). The pSP64-PolyA vector, obtained from Promega Corp. (Madison, Wis.), replicates in E. coli, but not in S. aureus. pSP64-PolyA also contains a unique EcoRI restriction site. An E. coli/S. aureus shuttle vector was constructed by digesting each vector with EcoRI, ligating the two vecotrs together, and transforming the DNA into E. coli. The resulting shuttle vector was designated pSPT264.

The recombinant plasmid (i.e., pSPT246 containing an amplified fragment) was used to transform E. coli, isolated, and then transferred to S. aureus RN4220 (described in Kreiswirth et al., Nature, 305, 709–712 (1983)) by electroporation. Transformants were selected by incubation on Nutrient agar plates containing tetracycline (10 μg/ml) at the permissive temperature (30° C.). The presence of the correct plasmid was verified by PCR.

One clone with the correct plasmid was grown on Nutrient agar with tetracycline (10 μg/ml) at 32° C. overnight to allow recombination between the plasmid and the selected chromosomal allele. To select for recombinants the bacteria were then grown at the non-permissive temperature (43° C.) for 18 hours in Brain Heart Infusion (BHI) broth without tetracycline, followed by a 1:10 dilution into BHI broth containing 5 μg/ml tetracycline. The cells were incubated overnight at 43° C. The bacterial culture was then diluted, spread on Nutrient agar plates containing 5 μg/ml tetracycline and incubated at 43° C. overnight. As the plasmid cannot replicate at 43° C., only cells with the plasmid integrated into the chromosome are tetracycline resistant and form colonies. Micro-colonies that appear at the non-permissive temperature are also considered, as they may represent mutations in coding sequences that are important, but not essential, for growth.

The plasmid integrates at a low frequency at other sites in the chromosome, thus tetracycline resistant clones appeared even when the target coding sequence was essential. Therefore, ten colonies from each selection at 43° C. were tested for specific integration of the plasmid into the selected target coding sequence by PCR. A primer pair consisting of one promer that binds to the vector DNA, and a second promer that binds upstream of the target coding sequence in the chromosome was used for PCR amplification. The primer pair amplifies the intervening chromosomal-vector region, and an amplified DNA fragment is produced only if the vector integrated at the predicted location. The absence of a band suggests the vector cannot integrate, and that the coding sequence is essential. Typically, all or none out of the tested colonies were specific recombinants. In those cases where no recombinants are found the target coding sequence is considered essential. For a number of target coding sequences (both essential and non-essential) the same results have been obtained when the whole selection procedure was repeated.

This protocol has successfully been used to analyze 60 out of the of 492 unknown complete or partial coding sequences identified. Out of the 60 analyzed coding sequences, 12 appeared to be essential and were further analyzed as described below.

EXAMPLE 2

Cloning of Essential S. aureus Coding Sequences and Expression in E. coli

Overview of the Expression System and Cloning Procedure

The overexpression of S. aureus proteins is accomplished using the Qiagen Type ATG expression system (Qiagen Gmbh, Santa Clara, Calif.). This system utilizes E. coli strain "M15" whose genotype has been described by Qiagen as Nal$^s$, Str$^s$, rif$^s$, lac$^-$, ara$^-$, gal$^-$, mtl$^-$, F$^-$, recA$^+$, uvr$^+$. Two replication compatible vectors, pREP4 and pQE-60 (each obtained from Qiagen), are introduced into the M15 strain during the procedure. Alternatively, pQE-70 can be used instead of pQE-60. The pREP4 vector is a pACYC-derived vector that contains the lacI gene encoding for the Lactose (LacI) repressor protein, and the vector contains kanamycin drug resistance. The expression vector pQE-60 is a pBR322-derived vector that contains a modified T5 phage promoter, a strong ribosme binding site (RBS), and the coding sequence of the specific S. aureus coding sequence to be expressed. The T5 promoter modifications include the placement of operator sites for binding and regulation of the promoter by the LacI repressor. Induction of expression is performed by the addition of IPTG (isopropylthio-β-D-galactoside) to a log phase culture.

The general cloning strategy is to first amplify the specific coding sequence from S. aureus genomic DNA using PCR primers to the 5' and 3' ends of the coding sequence. The PCR primers is designed to add a NcoI and a BglII restriction sites at the 5' and 3' ends of the coding sequence respectively. The coding sequence should be free of any NcoI or BglII restriction sites. If such sites are present, they were eliminated using site-directed PCR mutagenesis procedures known to the art. Alternatively, a different restriction site, for instance a BamHI restriction site, is used instead of a BglII restriction site. The amplified S. aureus coding sequence is ligated into pCR-2.1 (Invitrogen, Carlsbad, Calif.) and transformed into E. coli using techniques known to the art. Colonies are screened for the presence of the coding sequence by PCR amplification or vector restriction analysis. Clones are randomly selected and the nucleotide sequence of the insert DNA, i.e., the S. aureus coding sequence, is determined to confirm authenticity of the insert.

The pCR-2.1 vector containing the desired coding sequence is digested with NcoI/BglII and the coding sequence is isolated and ligated into the corresponding NcoI/BglII restriction sites of pQE-60. The ligation mixture is used to electroporate the vector DNA into the M15 strain that contains the pREP4 vector. The resulting transformants are screened by PCR or restriction analysis. Candidates are grown in a shake-flask and screened for the over-expression of a protein band having the appropriate size as analyzed by SDS-PAGE or Western analysis. Anti-His antibody (Invitrogen) is used in the Western analysis. A single candidate is selected for the overexpresion and isolation of the protein encoded by each coding sequence.

Culture and Media

The medium for cloning and maintenance of cells containing recombinant plasmids in E. coli is LB supplemented with the appropriate antibiotic (100 µg/ml ampicillin, 25 µg/ml kanamycin). S. aureus is grown in Mueller-Hinton medium. Competent INVF'α cells (Invitrogen, Carlsbad, Calif.) are used according to the manufacturer's direction. The M15 pREP-4 strain is purchased from Qiagen. SOC medium is used in the electroporation of cells. LB and SOC media are described in Sambrook et al. (*Molecular Cloning: A Laboratory Manual.*, Cold Spring Harbor Laboratory Press, pp. A1–A4 (1989)). Mueller-Hinton medium is described in Atlas et al., Handbook of Microbiological Media, CRC Press.

Design of the pQE60 Expression Vector

The portion of the pQE-60 DNA sequence containing the T5 promoter, the RBS, the ATG start codon (in bold), the NcoI restriction site (underlined), the BglII restriction site (underlined), 6 His tag (double underline), and the TAA stop codon (in bold) is shown (SEQ ID NO: 97):

```
CTCGAGAAAT CATAAAAAAT TTATTTGCTT TGTGAGCGGA

TAACAATTAT AATAGATTCA ATTGTGAGCG GATAACAATT

TCACACAGAA TTCATTAAAG AGGAGAAATT AACCATGGGA

GGATCCAGAT CTCATCACCA TCACCATCAC TAAGCTTAAT TA
NcoI
      BglII
```

The S. aureus coding sequences are modified by PCR to contain compatible in-frame NcoI and BglII restriction sites.

Primer Design

The general formula for the design of the primer to the 5' portion of the S. aureus coding sequence is usually 5'-CCATGGGAN$_{20-30}$. The formula for the 3' primer is usually 5'-AGATCTN$_{20-30}$. These primers added the NcoI and BglII restriction sequences. The first "N" nucleotide of the 5, sequence correspond to the codon of the second amino acid of the S. aureus coding sequence after its ATG start. The first "N" nucleotide of the 3, primer corresponds to the third nucleotide in the codon preceding the stop codon of the S. aureus coding sequence. The number of nucleotides to include in the primer varied depending on the specific DNA sequence, but was typically in a range of 20 to 30 bases. The primers are-phosphorylated.

TABLE 2

Primers used to amplify essential coding sequences from S. aureus

| Essential coding sequence | Primer pair used to clone coding sequence | Resulting sequence in pQE-60 | Predicted polypeptide |
| --- | --- | --- | --- |
| SEQ ID NO: 1 | SEQ ID NOs: 51–52 | SEQ ID NO: 49 | SEQ ID NO: 50 |
| SEQ ID NO: 3 | SEQ ID NOs: 55–56 | SEQ ID NO: 53 | SEQ ID NO: 54 |
| SEQ ID NO: 5 | SEQ ID NOs: 59–60 | SEQ ID NO: 57 | SEQ ID NO: 58 |
| SEQ ID NO: 7 | SEQ ID NOs: 63–64 | SEQ ID NO: 61 | SEQ ID NO: 62 |
| SEQ ID NO: 9 | SEQ ID NOs: 67–68 | SEQ ID NO: 65 | SEQ ID NO: 66 |
| SEQ ID NO: 11 | SEQ ID NOs: 71–72 | SEQ ID NO: 69 | SEQ ID NO: 70 |
| SEQ ID NO: 13 | SEQ ID NOs: 75–76 | SEQ ID NO: 73 | SEQ ID NO: 74 |
| SEQ ID NO: 15 | SEQ ID NOs: 79–80 | SEQ ID NO: 77 | SEQ ID NO: 78 |
| SEQ ID NO: 17 | SEQ ID NOs: 83–84 | SEQ ID NO: 81 | SEQ ID NO: 82 |
| SEQ ID NO: 19 | SEQ ID NOs: 87–88 | SEQ ID NO: 85 | SEQ ID NO: 86 |
| SEQ ID NO: 21 | SEQ ID NOs: 91–92 | SEQ ID NO: 89 | SEQ ID NO: 90 |
| SEQ ID NO: 23 | SEQ ID NOs: 95–96 | SEQ ID NO: 93 | SEQ ID NO: 94 |

Preparation of the S. aureus Genomic DNA

Strain ISP3 (obtained from S. Arvidson, Karolinska Institute) is used to inoculate 10 mls of Mueller-Hinton broth. After overnight growth at 37° C., 1.5 mls of culture are pelleted in an eppendorf tube and then resuspended in 400 µl of TE, pH 8.0 (Sambrook et al. (*Molecular Cloning: A Laboratory Manual.*, Cold Spring Harbor Laboratory Press, p. B.20 (1989). Following the addition of 50 µl lysostaphin solution (10 mg/ml), the cells are incubated at 37° C. for 1 hour. Seventy microliters of 10% SDS and 10 µl of proteinase K (20 mg/ml) are added and the incubation continued at 37° C. for another hour. After the addition of 100 µl of 5 M NaCl, the cell suspension is vortexed and 80 µl of a solution containing 10% hexadecyltrimethyl amn-nonium bromide, 0.7 M NaCl (CTAB/NaCl) is added. The cells are vortexed and then incubated at 65° C. for 10 minutes. Following the addition of an equal volume of 25:24:1 phenol:chloroform:isoamyl alcohol, the cells are vortexed and centrifuged for 5 minutes. The aqueous phase is then transferred to a fresh tube, leaving behind the white CTAB/NaCl interface. The extraction is repeated, and the aqueous layer is again transferred to a fresh tube. Following the addition of an equal volume of isopropanol, the tube is gently mixed causing a stringy precipitate to form. A Pasteur pipette fashioned into a small hook is used to gently remove the precipitate and to transfer it into another tube containing 1 ml of 70% ethanol. The tube is centrifuged, and the resulting pellet is washed once with 70% ethanol. After drying, the DNA pellet is resuspended in 100 µl of water and the concentration of the recovered DNA is determined using techniques known in the art.

PCR Amplification

PCR reactions are performed using either the Perkin-Elmer Cetus GeneAmp 9600 or 2400 thermal cyclers (Perkin-Elmer, Norwalk, Conn.). The deoxynucleotide mix and the Pfu DNA polymerase are purchased from Stratagene (La Jolla, Calif.). The AmpliTaq Gold kit is purchased from Perkin Elmer. The PCR synthesis protocol for long template amplification is as follows: 1 µg of S. aureus genomic DNA, 10 µl of 10× reaction buffer (with 15 mM $MgCl_2$), 500 ng of each primer, 16 µl of 1.25 mM dNTP's, 1 µl of AmpliTaq Gold, and water to 100 µl are added per PCR microtube. The DNA is amplified for 35 cycles using Cycle Program of 95° C. for 5 minutes followed by 35 cycles of 94° C. for 30 seconds, 50° C. for 1 minute and 72° C. for 3 minutes, an extension at 72° C. for 5 minutes, and finally 40° C. on hold. A 10 µl aliquot of the synthesis reaction is loaded onto a 1.2% agarose gel to confirm the presence and size of the synthesized fragment. The PCR product is produced by combining multiple PCR reaction, EtOH precipitating the DNA, and cutting the desired fragment out of a 1.2% agarose gel. The DNA is isolated from the agarose using Amicon Ultrafree-DA extraction filters (Millipore Corp., Bedford, Mass.). The filters are used according to manufacturer's directions.

Ligation and Transformation

The pQE-60 vector and the pCR2.1 vector containing the *S. aureus* coding sequence are digested with NcoI and BglII restriction enzymes. The pQE-60 vector fragment and the *S. aureus* coding sequence are isolated from an agarose gel. The two DNAs are ligated and transformed into electrocompetent M15 cells containing pREP-4, and plated on LB agar with ampicillin and kanamycin supplementation. Ligase is purchase from BioLab (Beverley, Mass.), and used in accordance with the manufacturer's instructions. Electroporation of the ligated DNA into M15 pREP-4 cells is performed using a Bio-Rad Gene Pulser (Hercules, Calif.). Competent cells are prepared from 1 liter of cells with an optical density of 1 at $A_{550}$. The cells are chilled and washed successively with 1 liter and 0.5 liters of ice cold sterile water. The cells are resuspended in 20 mls of ice cold sterile 10% glycerol, re-centrifuged and placed into a final suspension of 2 to 3 mls of cold sterile 10% glycerol. Fifty microliters of cells are mixed with 5 µls or less of ligated DNA. The cell/DNA mixture is transferred to an electroporation cuvette and pulsed with the settings at 25 µF, 2.5 kV, and the Pulse Controller set to 200 Ω. One ml of SOC media is then added. The cells are incubated at 30° C. for one hour and plated on selective media.

Several resultant colonies from the transformation are selected at random and vector DNA is isolated using the Miniprep or Maxiprep kits purchased from Qiagen. The vector DNA is isolated according to the manufacturer's instructions. The candidates are screened by restriction enzyme digestions. Restriction enzymes are purchased from New England BioLab (Beverly, Mass.). Restriction enzymes are used according to the manufacturer's instructions.

Expression Conditions

The expression culture is streaked on an LB plate containing ampicillin and kanamycin. A single colony isolate is used to inoculate 50 mls of LB medium supplemented with ampicillin and kanamycin and grown overnight at the desired temperature. Following sub-culture into the suitable volume of the identical media at 0.50 $A_{550}$/ml, the culture is grown at the same temperature with vigorous aeration until an $A_{550}$ of 3.0 was reached. The culture is induced by the addition of IPTG to a final concentration of 1 mM. Culture aliquots are removed at 0, 2, and 4 hours post-induction for SDS-PAGE or Western analysis. Cells are harvested for protein isolation between 4 and 6 hours. Proteins are isolated using a metal-chelate affinity chromatography purification system (QIAEXPRESS, Qiagen).

EXAMPLE 3

Use of Essential Coding Sequence Products in Screen for Antimicrobial Agents

Individual purified proteins (i.e., target proteins) are combined with samples and screened for ligands that would bind the target protein. The method used to screen is described in Hughes et al., U.S. Pat. No. 5,783,397. The screening is conducted by Cetek Corporation, Marlborough, Mass.

The complete disclosures of all patents, patent applications, publications, and nucleic acid and protein database entries, including for example GenBank accession numbers and EMBL accession numbers, that are cited herein are hereby incorporated by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

Sequence Listing Free Text

SEQ ID NOs: 25–48, 51, 52, 55, 56, 59, 60, 63, 64, 67, 68, 71, 72, 75, 76, 79, 80, 83, 84, 87, 88, 91, 92, 95, 96; Oligonucleotide primer SEQ ID NOs: 49, 53, 57, 61, 65, 69, 73, 77, 81, 85, 89, 93; Cloned essential coding sequence SEQ ID NOs: 50, 54, 58, 62, 66, 70, 74, 78, 82, 86, 90, 94; Polypeptide encoded by cloned essential coding sequence SEQ ID NO: 97; Portion of the pQE-60 DNA sequence

What is claimed is:

1. A method for determining whether an agent binds a polypeptide, the method comprising:

contacting the polypeptide and an agent to form a mixture, wherein the polypcptide is encoded by the nucleotide sequence SEQ ID NO:1; and determining whether the agent binds the polypeptide.

2. The meted of claim 1 wherein determining comprises an enzyme assay.

3. The method of claim 1 wherein determining comprises a binding assay.

4. The method of claim 1 wherein determining comprises a ligand binding assay.

5. The method of claim 1 further comprising detenning whether the agent decreases the growth rate of a microbe, comprising:

contacting a microbe with the agent in vitro, wherein the microbe is selected from the group consisting of *Staphylococcus epidennidis, Staphylococcus saprophyticus,* or *Staphylococcus aureus;* incubating the microbe and the agent under conditions suitable for growth of the microbe in the absence of the agent; and determining the growth rate of the microbe, wherein a decrease in growth rate compared to the growth rate of the microbe in the absence of the agent indicates the agent decreases the growth rate of the microbe.

6. The method of claim 1 further comprising determining whether the agent decreases the growth rate of an *S. auraus,* comprising:

contacting an *S. aureus* with the agent in vitro;

incubating the *S. aureus* and the agent under conditions suitable for growth of the *S. aureus* in the absence of the agent; and determining the growth rate of the *S. aureus,* wherein a. decrease in growth rate compared to the growth rate of the *S. aureus* in the absence of the agent indicates the agent decreases the growth rate of the *S. aureus.*

7. An agent determined to bind a polypeptide according to the method of claim 1.

8. An in vitro method for determining whether an agent binds a polypeptide, the method comprising:

contacting the polypeptide and an agent in vitro to form a mixture, wherein the polypeptide is encoded by the nucleotide sequence SEQ ID NO:1; and determining whether the agent binds the polypeptide.

9. The method of claim 8 further comprising determining whether the agent decreases the growth rate of a microbe, comprising:

contacting a microbe with the agent in vitro, wherein the microbe is selected from the group consisting of *Staphylococcus epidermidis, Staphylococcus saprophyticus,* or *Staphylococcus aureus;* incubating the microbe and the agent under conditions suitable for growth of the microbe in tbe absence of the agent; and determining the growth rate of the microbe, wherein a decrease in growth rate compared to the growth rate of the microbe in the absence of the agent indicates the agent decreases the growth rate of the microbe.

10. The method of claim 8 further comprising determining whether the agent decreases the growth rate of an *S. aureus,* comprising:

contacting an *S. aureus* with the agent in vitro;

incubating the *S. aureus* and the agent under conditions suitable for growth of the *S. aureus* in the absence of the agent; and determining the growth rate of the *S. aureus,* wherein a decrease in growth rate compared to the growth rate of the *S. aureus* in the absence of the agent indicates the agent decreases the growth rate of the *S. aureus.*

* * * * *